(12) United States Patent
Brown et al.

(10) Patent No.: US 11,987,648 B2
(45) Date of Patent: May 21, 2024

(54) CYCLOHEXAPEPTIDES AS SELECTIVE SOMATOSTATIN SST5 RECEPTOR AGONISTS

(71) Applicant: Heptares Therapeutics Limited, Cambridge (GB)

(72) Inventors: Giles Albert Brown, Cambridge (GB); Miles Stuart Congreve, Cambridge (GB); Conor Scully, Cambridge (GB); Rebecca Paul, Cambridge (GB); Andrea Bortolato, Cambridge (GB)

(73) Assignee: Heptares Therapeutics Limited, Cambridge (GB)

( * ) Notice: Subject to any disclaimer, the term of this patent is extended or adjusted under 35 U.S.C. 154(b) by 513 days.

(21) Appl. No.: 17/284,399

(22) PCT Filed: Oct. 14, 2019

(86) PCT No.: PCT/GB2019/052911
§ 371 (c)(1),
(2) Date: Apr. 9, 2021

(87) PCT Pub. No.: WO2020/074926
PCT Pub. Date: Apr. 16, 2020

(65) Prior Publication Data
US 2021/0363188 A1    Nov. 25, 2021

(30) Foreign Application Priority Data
Oct. 12, 2018   (GB) .................................... 1816637

(51) Int. Cl.
| | | |
|---|---|---|
| *C07K 7/64* | (2006.01) | |
| *A61K 38/00* | (2006.01) | |
| *A61P 5/02* | (2006.01) | |
| *A61P 35/00* | (2006.01) | |

(52) U.S. Cl.
CPC .................. *C07K 7/64* (2013.01); *A61P 5/02* (2018.01); *A61P 35/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 6,001,960 A | 12/1999 | Hirschmann et al. | |
| 6,268,342 B1 * | 7/2001 | Culler | A61P 31/18 514/3.8 |
| 2016/0184388 A1 | 6/2016 | Schmid | |

FOREIGN PATENT DOCUMENTS

| | | |
|---|---|---|
| CN | 101298472 A | 11/2008 |
| EP | 1648934 A2 | 4/2006 |
| EP | 1758553 A1 | 3/2007 |
| EP | 2225271 A2 | 9/2010 |
| GB | 2203337 A | 10/1988 |
| JP | 2007-536195 A | 12/2007 |
| JP | 2008-501757 A | 1/2008 |
| JP | 2011-505345 A | 2/2011 |

OTHER PUBLICATIONS

Bruns et al., SOM230: a novel somatostatin peptidomimetic with broad somatotropin release inhibiting factor (SRIF) receptor binding and a unique antisecretory profile. Eur J Endocrinol. May 2002; 146(5):707-16.
Lewis et al., A novel somatostatin mimic with broad somatotropin release inhibitory factor receptor binding and superior therapeutic potential. J Med Chem. Jun. 5, 2003;46(12):2334-44.
Rai et al., Therapeutic uses of somatostatin and its analogues: Current view and potential applications. Pharmacol Ther. Aug. 2015; 152:98-110.
Sun et al., Somatostatin and its Analogs. Curr Drug Targets. 2016;17(5):529-37.
Great Britain Search Report for Application No. GB1816637.1, dated May 31, 2019, 4 pages.
International Search Report and Written Opinion for Application No. PCT/GB2019/052911, dated Dec. 5, 2019, 8 pages.
Yunlin et al., Quantitative analysis of pasireotide (SOM230), a cyclic peptide, in monkey plasma using liquid chromatography in combination with tandem mass spectrometry. J Chromatogr B Analyt Technol Biomed Life Sci. Jan. 1, 2016;1008:242-249.

* cited by examiner

*Primary Examiner* — Christina Bradley
(74) *Attorney, Agent, or Firm* — Barnes & Thornburg LLP

(57) ABSTRACT

The disclosures herein relate to novel compounds of formula (1):(1) and salts thereof, wherein W, X, Y, Z, m, n, q, $R^1$, $R^2$, $R^3$, $R^4$, $R^5$ and $R^6$ are defined herein, and their use in treating, preventing, ameliorating, controlling or reducing the risk of disorders associated with somatostatin receptors.

21 Claims, 11 Drawing Sheets

(1)

CYCLOHEXAPEPTIDES AS SELECTIVE SOMATOSTATIN SST5 RECEPTOR AGONISTS

CROSS-REFERENCE TO RELATED APPLICATIONS

This application is a 35 U.S.C. § 371 national stage filing of International Application No. PCT/GB2019/052911, filed on Oct. 14, 2019, which claims priority to United Kingdom Application No. 1816637.1, filed on Oct. 12, 2018, the entire contents of each of which are incorporated herein by reference.

This invention relates to a class of novel cyclic peptide compounds, their salts, pharmaceutical compositions containing them and their use in therapy of the human body. In particular, the invention is directed to a class of compounds which are agonists of the somatostatin receptor (SST). More particularly, the invention is directed to compounds that are selective agonists of the somatostatin receptor type 5 ($SST_5$). The invention also relates to the manufacture and use of these compounds and compositions in the prevention or treatment of such diseases in which somatostatin receptors are involved.

BACKGROUND OF THE INVENTION

Somatostatin is a ubiquitously distributed cyclic polypeptide hormone that exerts its physiological function by acting as an agonist of somatostatin receptor subtypes 1-5 ($SST_{1-5}$). The two biologically active forms of somatostatin, referred to as somatostatin-14 and -28 based on their amino acid chain length, are derived from a 92-amino acid precursor protein and show different SST selectivity profiles. Whilst somatostatin-14 has a higher binding affinity for $SST_{1-4}$, somatostatin-28 is more selective for $SST_5$. The hypothalamus is the primary site of somatostatin production in the central nervous system and the hypophyseal portal system allows direct access the pituitary gland in which expression of $SST_1$, $SST_2$, $SST_3$ and $SST_5$ has been demonstrated. Somatostatin-14 can act on different pituitary cell types including somatotrophs and corticotrophs and regulate secretion of hormones such as growth hormone (GH) and adrenocorticotropic hormone (ACTH), respectively. Furthermore, somatostatin is also synthesised in peripheral regions such as the mucosa of the gastrointestinal tract and pancreatic islets, where it can modulate secretion of local hormones in an autocrine and/or paracrine manner.

The five SST subtypes belong to the G protein-coupled receptor (GPCR) superfamily and were cloned in independent studies in 1992 as mediators of somatostatin-dependent effects. Two splice variants of $SST_2$, $SST_{2A}$ and $SST_{2B}$, have been identified in murine brain regions including cortex, hippocampus, striatum and hypothalamus and a transcript encoding $SST_{2B}$ has also been found in tissue isolated from human somatotroph adenomas. $SST_5$ also exists in several expression isoforms in humans, which are functional despite either two or three transmembrane domains being deleted due to cryptic splice sites. Expression of SSTs has been demonstrated in a variety of tissues that coincide with functional activity of somatostatin. Anatomical profiling of GPCR expression in mice highlighted expression of all SST subtypes in multiple brain regions including hippocampus, hypothalamus and the pituitary gland; however, in the periphery $SST_2$ appears to be the predominantly expressed SST subtype. In healthy human tissues SSTs are similarly distributed with expression of all subtypes in the brain and selected subtype expression in peripheral organs, such as $SST_{1-3}$ in the eye, $SST_1$ in the stomach and kidneys, $SST_{1-3}$ and $SST_5$ in the pancreas and $SST_5$ in the pituitary gland. Multiple independent studies have also identified SST mRNA and protein expression in several human tumours, including pituitary tumours, neuroendocrine tumours, renal cell cancer, breast cancer, meningioma, glioma, neuroblastoma and colorectal cancer. The ability of SSTs to attenuate hormonal secretion provides a potential strategy for therapeutically managing the enhanced secretory activity of tumours. Furthermore, extensive evidence has highlighted that SST signalling also has an antiproliferative effect on tumour cells.

The main molecular mechanism of SST activity is based on their ability to couple to the Gi subtype of G proteins, which has an inhibitory effect on adenylate cyclase and thereby results in suppression in cAMP production. Furthermore, SSTs also have the capacity to affect ion channel signalling; SST activation has been linked to activation of $K^+$ channels and inhibition of $Ca^{2+}$ channels. These signalling cascades triggered by SST agonists result in inhibition of exocytosis, which forms the basis of their inhibitory effect on hormone secretion. Another signalling output of SST activation, specifically of those receptors present on tumour cells, is suppression of proliferation, which is primarily mediated by Gi-dependent coupling to protein tyrosine phosphatases such as SHP-1 and -2. Multiple SSTs have been shown to attenuate growth factor receptor signalling) and downregulate synthesis of growth factors such as growth hormone (GH) and insulin-like growth factor 1 (IGF-1), block cell cycle progression, inhibit angiogenesis, likely by blocking nitric oxide synthase activity, and activate apoptosis-inducing pathways such as inhibition of the $Na^+$/$H^+$ exchanger, which is also involved in regulating cell adhesion and motility.

SST agonists have therapeutic potential in a range of pituitary disorders, as there is substantial evidence supporting the hypothesis that SST agonists could be beneficial in the treatment of pituitary tumours. SST expression has been demonstrated in pituitary tumours and although the up- and/or downregulation of specific SST subtypes appears to be variable and dependent on tumour subtype and individual patients, SSTR2 and SSTR5 appear to be present in the majority of cases. Furthermore, SST agonists have an antisecretory effect on both healthy and cancerous pituitary gland tissue including somatotroph and corticotroph adenomas. The efficacy of available somatostatin analogues, first-generation $SST_2$-selective agonists octreotide and lanreotide and second-generation multi-receptor agonist pasireotide, has been demonstrated in treatment of multiple disorders arising from of pituitary adenomas. Long-acting release (LAR) formulations of octreotide and lanreotide have been successfully employed for treatment of acromegaly, whose symptoms are associated with GH-secreting adenomas of the pituitary gland. A meta-analysis of 44 clinical studies demonstrated that up to two-thirds of patients achieved biochemical control following octreotide LAR treatment, as defined by normalisation of circulating GH and IGF-1 levels, and tumour shrinkage was observed in half of the cases. Treatment of acromegaly patients naïve to medical therapy or inadequately controlled by octreotide LAR with multi-receptor agonist pasireotide, which has a significantly higher affinity for $SST_5$, $SST_1$ and $SST_3$ compared with octreotide, showed positive results with improved biochemical control compared to octreotide and efficacy in patients resistant to $SST_2$-selective agonist treatment.

Somatostatin analogues are efficacious in the treatment of Cushing's Disease, which is characterised by ACTH hypersecretion. In line with the predominant expression of SSTR5 on corticotroph adenomas, pasireotide treatment of Cushing's Disease patients in a Phase II trial resulted in significant reduction of cortisol levels and tumour shrinkage. Furthermore, pasireotide treatment of Cushing's Disease patients in a Phase Ill trial resulted in significant reduction of urine free cortisol levels. This was associated with significant improvement of disease-specific signs and symptoms such as decrease in blood pressure, reductions in total cholesterol and low-density lipoprotein-cholesterol, and reductions in body mass index, weight and waist circumference. Moreover, pasireotide has been shown to lower plasma ACTH levels in patients with Nelson's syndrome.

Selected cases have reported the ability of octreotide to inhibit thyroid-stimulating hormone (TSH) secretion from pituitary thyrotropinomas. The extent of octreotide efficacy appears to be dependent on expression levels of SSTR2 versus SSTR5. In several pre-clinical studies SST agonists have shown an antisecretory effect on in vitro cultures of prolactin-secreting prolactinomas and expression analysis of gonadotropin-releasing adenomas suggests that somatostatin analogues targeting $SST_3$ rather than $SST_2$ are likely to be more efficacious than $SST_2$-selective agonists.

In addition to pituitary adenomas that show clinical symptoms associated with hormonal hypersecretion, SST agonists also have potential application in treatment of non-functioning pituitary adenomas. Pasireotide administration reduced cell viability of non-functioning adenoma cultures in vitro by inhibiting vascular endothelial growth factor release and pasireotide LAR is being evaluated in a Phase II study assessing its efficacy and safety in the treatment of patients with clinically non-functioning pituitary adenoma.

Selective SST agonists therefore have potential utility to treat disorders associated with functional pituitary adenomas and altered levels of pituitary hormones such as GH and associated excess of IGF-1 (including but not limited to treatment of acromegaly as well as type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. morbid obesity, hypothalamic or hyperinsulinemic obesity), excessive ACTH and cortisol (including but not limited to treatment of Cushing's Syndrome or Disease and associated conditions e.g. Nelson's Syndrome), excessive prolactin-associated disorders (including but not limited to treatment of Hyperprolactinemia), LH/FSH-secreting gonadotroph pituitary adenomas, TSH-secreting thyrotroph adenomas (including but not limited to thyrotropinoma and associated conditions e.g. hyperthyroidism) and clinically non-functioning pituitary adenomas.

The therapeutic benefit of the antisecretory and antiproliferative effect of SST agonists has also been demonstrated in other classes of cancer, such as neuroendocrine tumours (NETs), which arise from neuroendocrine cells present in a broad range of tissues and are characterised by excessive hormone secretion. Assessment of SST expression across NETs of different tissue origin across independent studies suggests that SSTR2 and SSTR5 are the most broadly expressed subtypes, while SSTR1, SSTR3 and SSTR4 appear to be more selectively expressed in specific tissues (Vitale et al. 2018). However, it is likely that similarly to pancreatic tumours, expression of respective SST subtypes will differ between individuals. The first-line therapy for NETs is surgical intervention with the aim of complete resection, however SST agonists have demonstrated efficacy in therapeutic management of unresectable NETs in independent pre-clinical and clinical studies. Treatment with first-generation SST agonist lanreotide and second-generation SST agonist pasireotide has been shown to alleviate symptoms of carcinoid syndrome, which is caused by carcinoid tumours, a type of slow-growing NET that occurs most commonly in the gastrointestinal tract. Furthermore, pasireotide LAR treatment alone or in combination with everolimus showed evidence of antitumour activity and potential for improvement of progression-free survival in Phase II trials in medullary thyroid cancer and in carcinoid tumours of lung and thymic origin. In addition to NETs, pasireotide also demonstrated clinical benefit in the treatment of non-neuroendocrine tumours, resulting in limitation of disease progression in 45% of patients in a Phase II trial in hepatocellular carcinoma and achieving a disease control rate of 68% in a Phase I trial in pancreatic cancer using a combination treatment with gemcitabine.

Selective SST agonists used alone or in combination with other therapeutic agents therefore have potential utility to treat tumours and related disorders, including but not limited to cancers of skin (e.g. metastatic melanoma and Merkel cell carcinoma), lung (e.g. small cell lung cancer and non-small cell lung cancer, including adenocarcinoma and squamous cell cancer), liver (e.g. hepatocellular carcinoma), pancreatic, gastrointestinal, prostate (including prevention of post-operative pancreatic fistula development following elective pancreatic resection), thymic (e.g. thymoma and thymic carcinoma) and adrenal origin; neuroendocrine tumours; carcinoid tumours and associated carcinoid syndrome.

Substantial evidence suggests that SST agonists would have therapeutic benefit in conditions related to dysregulation of glucose homeostasis. Expression of SSTs has been demonstrated in endocrine cells of the pancreas, including glucagon-secreting alpha, insulin-secreting beta and somatostatin-secreting delta cells. SSTR1, SSTR3, and SSTR4 expression was demonstrated in all endocrine cell types of the human pancreas, while SSTR2 was more frequently expressed in alpha and beta cells, and SSTR5 expressed mostly in beta and delta cells. Multiple independent pre-clinical studies have suggested that either $SST_5$ or $SST_2$ are the primary SSTR to contribute to inhibition of insulin secretion and the target molecular mechanism to achieve an optimal balance between inhibition of insulin and glucagon secretion is not fully understood. However, clinical evidence suggests that SSTR agonists are efficacious in the treatment of conditions associated with increased levels of insulin and/or decreased blood glucose levels.

LARs of octreotide and lanreotide have been successfully employed to treat congenital hyperinsulinism (CHI), especially in cases where patients were not responsive to diazoxide. Pan-selective SST agonist pasireotide is also currently being evaluated in the treatment of CHI. The long-acting nature of these formulations allows treatment to be reduced to once-monthly injections, which also significantly contributes to improving quality of life. Another condition resulting in hyperinsulinemic hypoglycaemia in which SST agonists have shown therapeutic potential is post-gastric bypass hypoglycaemia, which can be caused by Dumping syndrome, nesidioblastosis and/or insulinoma. Octreotide and pasireotide treatment were able to control hypoglycaemia in independent case studies. Furthermore, pasireotide was able to significantly reduce incidence of hypoglycaemia in a Phase II trial in Dumping syndrome, one of the main causes of post-gastric bypass hypoglycaemia.

Selective SST agonists therefore have potential utility to treat disorders associated with hyperinsulinemic hypoglycaemia, including but not limited to congenital hyperinsulinism, post-gastric bypass hypoglycaemia and conditions that can lead to hypoglycaemia, e.g. Dumping syndrome, nesidioblastosis and insulinoma.

Somatostatin also plays an important role in the retina, as it is one of the key neuroprotective factors produced by the retinal pigment epithelium and multiple SSTs are expressed in the retina with SSTR1 and SSTR2 being the most prevalent. Multiple mechanisms of somatostatin action contribute to its neuroprotective properties, such as its ability to inhibit glutamate release, which is thought to majorly contribute to neurodegeneration through over-excitation of retinal glutamate receptors, and to attenuate secretion of vascular endothelial growth factor that can contribute to ischemic damage. Somatostatin analogues have shown efficacy in different eye conditions; octreotide treatment over 3 years was able to reduce vitreous haemorrhage and resulted in improvement of visual acuity in patients with proliferative diabetic retinopathy; a meta-analysis of clinical studies demonstrated that octreotide showed efficacy in treatment of different stages of diabetic retinopathy and thyroid eye disease; and an improvement of visual acuity in some cases of cystoid macular edema after treatment with octreotide). Although pasireotide has not yet been tested in a clinical setting to assess its efficacy in eye-related disorders, pre-clinical studies have shown that pasireotide also has a neuroprotective effect in retinopathies.

Selective SST agonists therefore have potential utility to treat eye-related disorders that would benefit from neuroprotective agents, including but not limited to different types of diabetic retinopathy (e.g. early and proliferative); macular edema; and thyroid eye disease.

There is emerging pre-clinical evidence that SST agonists many have a therapeutic benefit in the treatment of polycystic kidney disease (PKD) and PKD-associated development of cysts in other organs, most commonly the liver. As increased levels of cAMP in renal tubular epithelia has been linked to acceleration of PKD progression, the activation of Gi-dependent signalling pathways by SST agonists should have a beneficial effect. Indeed, in a rat model of PKD combined treatment with octreotide and pasireotide resulted in a reduction in kidney weight and renal cyst area, while combination of pasireotide treatment with a histone deacetylase 6 inhibitor achieved a reduction in hepato-renal cyst growth in the same model system. There is also evidence of octreotide being beneficial in the treatment of polycystic ovary syndrome. Selective SST agonists therefore have potential utility to treat PKD and associated cyst development in other organs, included but not limited to polycystic liver disease and polycystic ovary syndrome.

Pre-clinical and clinical evidence suggests that treatment with SST agonists results in reduction of portal hypertension, a common complication of cirrhosis. Combination treatment in a rat model of cirrhosis with celecoxib and octreotide resulted in reduction of portal hypertension through inhibition of angiogenesis, and in a clinical study comparing octreotide LAR treatment to the placement of transjugular intrahepatic portosystemic shunts (TIPS) in patients with portal hypertension, administration of octreotide was similarly efficacious in reducing hepatic pressure as TIPS placement. Selective SST agonists therefore have potential utility to treat portal hypertension and conditions that can be caused by portal hypertension (e.g. ascites).

SST agonists may have therapeutic potential in the treatment of gastrointestinal disorders, as they have the capacity to inhibit gastric acid secretion, exocrine and endocrine pancreatic secretion and gastrointestinal peptide secretion. Selective SST agonists therefore have potential utility to treat gastrointestinal disorders including but not limited to treatment of peptic ulcers, enterocutaneous and pancreatic fistula, irritable bowel syndrome and disease, watery diarrhea syndrome, AIDS-related diarrhea, chemotherapy-induced diarrhea, acute or chronic pancreatitis and gastrointestinal bleeding.

Some pain disorders may be amenable to treatment with selective SST agonists; octreotide has been successfully employed to relief pain in cancer patients for whom opiate analgesics did not provide sufficient pain control and acute treatment of cluster headaches with octreotide resulted in significantly superior pain relief compared to placebo. Selective SST agonists may therefore be useful in the treatment of pain disorders, including but not limited to headache disorders (e.g. migraine, cluster headache and tension-type headache), neuropathic pain, hyperalgesia, causalgia, acute pain, burn pain, atypical facial pain, back pain, complex regional pain syndrome I and II, post-chemotherapy pain, post-stroke pain, post-operative pain and other conditions associated with pain.

BRIEF SUMMARY OF THE INVENTION

The present invention provides compounds having activity as somatostatin receptor agonists. More particularly, the invention provides compounds that exhibit selectivity for the somatostatin receptor type 5 ($SST_5$) relative to other somatostatin receptor subtypes including the somatostatin receptor type 2 ($SST_2$).

Accordingly, in one embodiment the invention provides a compound of the formula (1):

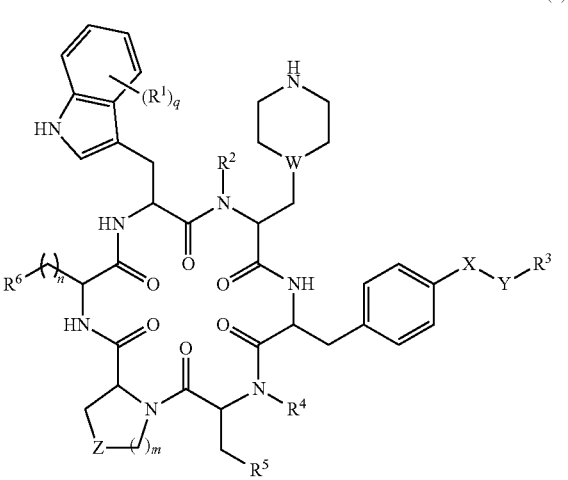

or a salt thereof, wherein;
W is CH or N;
X and Y are $CH_2$ or O, wherein one of X and Y is $CH_2$ and the other of X and Y is O;
Z is $CHR^7$, $NR^8$ or O;
m is 1 or 2;
n is 0 to 3;

each $R^1$ is independently selected from halo, $C_1$-$C_3$ alkyl and $C_1$-$C_3$ alkoxy, wherein the $C_1$-$C_3$ alkyl and alkoxy groups are optionally substituted with up to 6 fluorine atoms;

q is 0 to 2;

$R^2$ is selected from H and $C_1$-$C_3$ alkyl optionally substituted with up to 6 fluorine atoms;

$R^3$ is selected from optionally substituted $C_1$-$C_6$ alkyl, optionally substituted $C_3$-$C_6$ cycloalkyl, optionally substituted aryl and optionally substituted heteroaryl;

$R^4$ is H or optionally substituted $C_1$-$C_3$ alkyl, where the $C_1$-$C_3$ alkyl group is optionally joined to $R^5$ to form a ring;

$R^5$ is selected from optionally substituted $C_1$-$C_6$ alkyl, optionally substituted aryl and optionally substituted heteroaryl, where $R^5$ is optionally joined to $R^4$ to form a ring;

$R^6$ is selected from optionally substituted aryl, optionally substituted heteroaryl, optionally substituted O-aryl or optionally substituted O-heteroaryl;

$R^7$ is selected from H, optionally substituted $C_1$—C alkyl, $CONR^{10}R^{11}$, $OCONR^{10}R^{11}$, $OCOR^{10}$, $OCOOR^{10}$, $COOR^{10}$ or $OR^{12}$;

$R^8$ is selected from H, $CONR^{10}R^{11}$ or $COOR^{10}$;

$R^{10}$ and $R^{11}$ are independently selected from H, optionally substituted $C_1$-$C_6$ alkyl and optionally substituted $C_2$-$C_6$ alkyl where any one atom in the $C_2$-$C_6$ alkyl group is replaced by a heteroatom selected from N, O and S, or wherein $R^{10}$ and $R^{11}$ are optionally joined to form a ring; and $R^{12}$ is optionally substituted aryl or optionally substituted heteroaryl.

Particular compounds also include compounds of formula (1a):

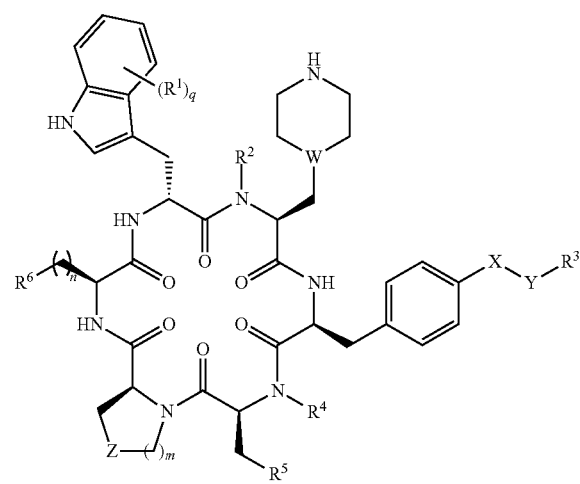

(1a)

or a salt thereof, wherein W, X, Y, Z, m, n, q, $R^1$, $R^2$, $R^3$, $R^4$, $R^5$ and $R^6$ are as defined above.

Particular compounds also include compounds of formula (1b):

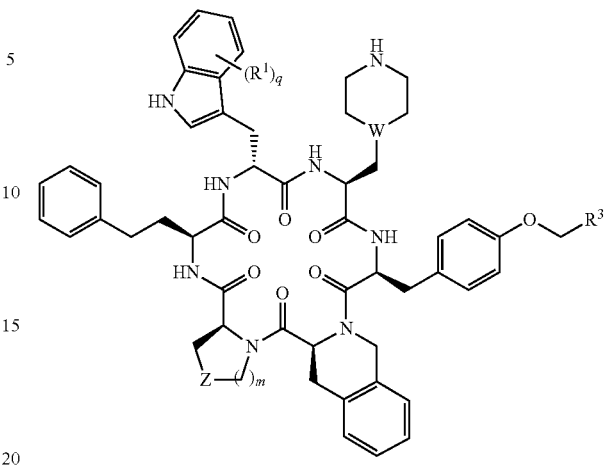

(1b)

or a salt thereof, wherein W, Z, m, q, $R^1$ and $R^3$ are as defined above.

The compounds herein may be used as agonists of the somatostatin receptor type 5 ($SST_5$). The compounds may be used in the manufacture of medicaments. The compounds or medicaments may be for use in treating, preventing, ameliorating, controlling or reducing the risk of disorders associated with somatostatin receptors including Cushing's Disease, Cushing's Syndrome, Acromegaly, Neuroendocrine tumours (inc. Carcinoid tumours), Thyrotropinomas, Prolactinomas, Non-functioning pituitary adenomas, Nelson's syndrome, Congenital hyperinsulinism, Post-gastric bypass hypoglycaemia, Dumping syndrome, Hyperinsulinemic obesity, Insulinoma, Polycystic kidney disease, Polycystic liver disease, Portal hypertension, Ascites, Pancreatic cancer, Pancreatic fistula, Acute or chronic pancreatitis, Hepatocellular carcinoma, Irritable bowel syndrome/disease, Headache disorders (inc. migraine, cluster headache, tension-type headache), Nesidioblastosis, Neuropathic pain, Hyperalgesia, Causalgia, Acute pain, Burn pain, Atypical facial pain, Back pain, Complex regional pain syndrome I and II, Post-chemotherapy pain, Post-stroke pain, Post-operative pain, Type I diabetes mellitus, Type II diabetes mellitus, Diabetic retinopathy, Diabetic macular edema, Thyroid eye disease, Cystoid macular edema, Diabetic nephropathy, Diabetic neuropathy, Peptic ulcers, Enterocutaneous, Watery diarrhea syndrome, AIDS-related diarrhea, Chemotherapy-induced diarrhea and Gastrointestinal bleeding.

DETAILED DESCRIPTION OF THE INVENTION

Figure 1:
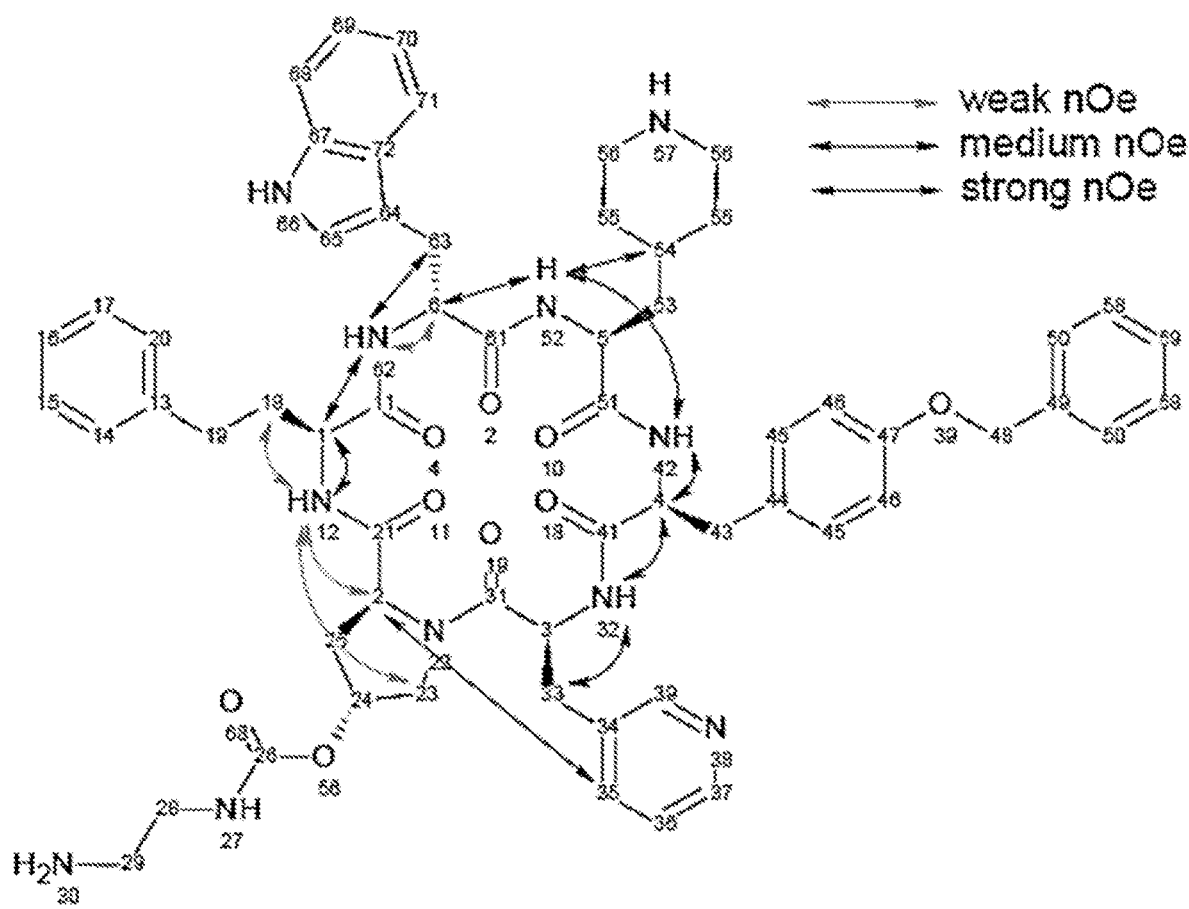
FIGS. 1-11 illustrate compounds of the present disclosure and, with reference to Table 3 hereinbelow, provide representative exemplification for $^1$H NMR and $^{13}$C NMR characterization.

The invention relates to novel compounds. The invention also relates to the use of novel compounds as agonists of the $SST_5$ receptor. The invention further relates to the use of novel compounds in the manufacture of medicaments for use as $SST_5$ receptor agonists or for the treatment of disorders associated with somatostatin receptors. The invention further relates to compounds, compositions and medicaments which are selective $SST_5$ receptor agonists.

The invention further relates to compounds, compositions and medicaments useful for the treatment of Cushing's Disease, Cushing's Syndrome, Acromegaly, Neuroendocrine tumours (inc. Carcinoid tumours), Thyrotropinomas, Prolactinomas, Non-functioning pituitary adenomas, Nelson's syndrome, Congenital hyperinsulinism, Post-gastric bypass hypoglycaemia, Dumping syndrome, Hyperinsulinemic obesity, Insulinoma, Polycystic kidney disease, Polycystic liver disease, Portal hypertension, Ascites, Pancreatic cancer, Pancreatic fistula, Acute or chronic pancreatitis, Hepatocellular carcinoma, Irritable bowel syndrome/disease, Headache disorders (inc. migraine, cluster headache, tension-type headache), Nesidioblastosis, Neuropathic pain, Hyperalgesia, Causalgia, Acute pain, Burn pain, Atypical facial pain, Back pain, Complex regional pain syndrome I and II, Post-chemotherapy pain, Post-stroke pain, Post-operative pain, Type I diabetes mellitus, Type II diabetes mellitus, Diabetic retinopathy, Diabetic macular edema, Thyroid eye disease, Cystoid macular edema, Diabetic nephropathy, Diabetic neuropathy, Peptic ulcers, Enterocutaneous, Watery diarrhea syndrome, AIDS-related diarrhea, Chemotherapy-induced diarrhea and Gastrointestinal bleeding.

Compounds of the invention include compounds of the formula (1):

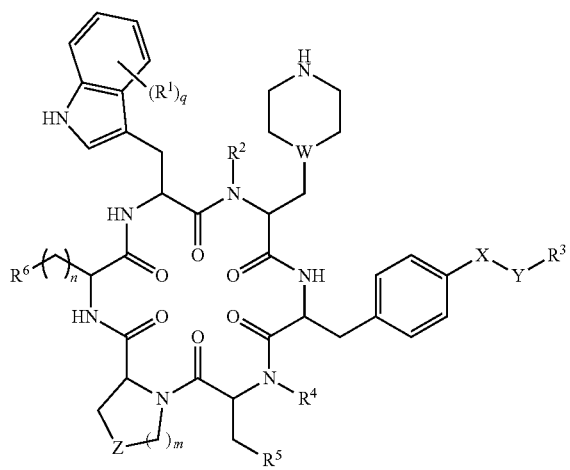

(1)

or a salt thereof, wherein;
W is CH or N;
X and Y are $CH_2$ or O, wherein one of X and Y is $CH_2$ and the other of X and Y is O;
Z is $CHR^7$, $NR^8$ or O;
m is 1 or 2;
n is 0 to 3;
each $R^1$ is independently selected from halo, $C_1$-$C_3$ alkyl and $C_1$-$C_3$ alkoxy, wherein the $C_1$-$C_3$ alkyl and alkoxy groups are optionally substituted with up to 6 fluorine atoms;
q is 0 to 2;
$R^2$ is selected from H and $C_1$-$C_3$ alkyl optionally substituted with up to 6 fluorine atoms;
$R^3$ is selected from optionally substituted $C_1$-$C_6$ alkyl, optionally substituted $C_3$-$C_6$ cycloalkyl, optionally substituted aryl and optionally substituted heteroaryl;

$R^4$ is H or optionally substituted $C_1$-$C_3$ alkyl, where the $C_1$-$C_3$ alkyl group is optionally joined to $R^5$ to form a ring;
$R^5$ is selected from optionally substituted $C_1$-$C_6$ alkyl, optionally substituted aryl and optionally substituted heteroaryl, where $R^5$ is optionally joined to $R^4$ to form a ring;
$R^6$ is selected from optionally substituted aryl, optionally substituted heteroaryl, optionally substituted O-aryl or optionally substituted O-heteroaryl;
$R^7$ is selected from H, optionally substituted $C_1$-$C_6$ alkyl, $CONR^{10}R^{11}$, $OCONR^{10}R^{11}$, $OCOR^{10}$, $OCOOR^{10}$, $COOR^{10}$ or $OR^{12}$;
$R^8$ is selected from H, $CONR^{10}R^{11}$ or $COOR^{10}$;
$R^{10}$ and $R^{11}$ are independently selected from H, optionally substituted $C_1$-$C_6$ alkyl and optionally substituted $C_2$—C alkyl where any one atom in the $C_2$-$C_6$ alkyl group is replaced by a heteroatom selected from N, O and S, or wherein $R^{10}$ and $R^{11}$ are optionally joined to form a ring; and
$R^{12}$ is optionally substituted aryl or optionally substituted heteroaryl.

W can be CH or N. W can be CH. W can be N.
X and Y can be $CH_2$ or O, wherein one of X and Y is $CH_2$ and one of X and Y is O.
X can be $CH_2$. X can be O.
Y can be $CH_2$. Y can be O.
Z can be $CHR^7$, $NR^8$ or O. Z can be $CHR^7$. Z can be $NR^8$. Z can be O.
m can be 1 or 2. m can be 1. m can be 2.
n can be 0 to 3. n can be 0. n can be 1. n can be 2. n can be 3.

Each occurrence of $R^1$ can be halo, $C_1$-$C_3$ alkyl or $C_1$-$C_3$ alkoxy, wherein the $C_1$-$C_3$ alkyl and alkoxy groups are optionally substituted with up to 6 fluorine atoms. $R^1$ can be methoxy or methyl. $R^1$ can be methoxy. $R^1$ can be methyl. $R^1$ can be OMe or Me. $R^1$ can be OMe. $R^1$ can be Me.
q can be 0 to 2. q can be 0. q can be 1. q can be 2.
$R^2$ can be H or $C_1$-$C_3$ alkyl optionally substituted with up to 6 fluorine atoms. $R^2$ can be hydrogen. $R^2$ can be H. $R^2$ can be methyl. $R^2$ can be Me.
$R^3$ can be optionally substituted $C_1$-$C_6$ alkyl, optionally substituted $C_3$-$C_6$ cycloalkyl, optionally substituted aryl or optionally substituted heteroaryl. $R^3$ can be optionally substituted $C_1$-$C_6$ alkyl, optionally substituted $C_3$-$C_6$ cycloalkyl or optionally substituted aryl, wherein the optional substituents are selected from halo, $C_1$-$C_3$ alkyl and $C_1$-$C_3$ alkoxy, wherein the $C_1$-$C_3$ alkyl and alkoxy groups are themselves optionally substituted with up to 6 fluorine atoms. $R^3$ can be optionally substituted phenyl, optionally substituted cyclohexyl, optionally substituted cyclopentyl or optionally substituted cyclobutyl, wherein the optional substituents are selected from chloro, bromo and fluoro. $R^3$ can be phenyl, optionally substituted with chloro, bromo or fluoro. $R^3$ can be phenyl.
$R^4$ can be H or optionally substituted $C_1$-$C_3$ alkyl, where the $C_1$-$C_3$ alkyl group is optionally joined to $R^5$ to form a ring. $R^4$ can be hydrogen. $R^4$ can be H. $R^4$ can be optionally substituted $C_1$-$C_3$ alkyl. $R^4$ can be $C_1$-$C_3$ alkyl. $R^4$ can be joined to $R^5$ to form a ring.
$R^5$ can be optionally substituted $C_1$—C alkyl, optionally substituted aryl or optionally substituted heteroaryl, where $R^5$ is optionally joined to $R^4$ to form a ring. $R^5$ can be optionally substituted aryl or optionally substituted heteroaryl, wherein the optional substituents are selected from halo, $C_1$-$C_3$ alkyl and $C_1$-$C_3$ alkoxy, wherein the $C_1$-$C_3$ alkyl and alkoxy groups are themselves optionally substituted with up to 6 fluorine atoms. $R^5$ can be optionally substituted phenyl or optionally substituted pyridyl, wherein the optional substituents are selected from chloro, bromo, fluoro and OMe. $R^5$ can be phenyl. $R^5$ can be pyridyl.

$R^5$ can be joined to $R^4$ to form a ring. $R^4$ and $R^5$ can be joined to form a ring selected from the group consisting of:

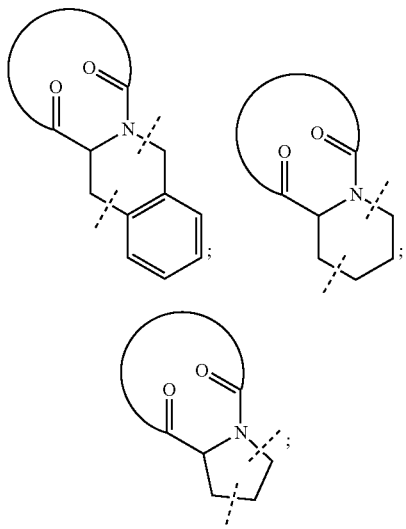

wherein said ring moieties are optionally substituted with a group or groups selected from halo, $C_1$-$C_3$ alkyl and $C_1$-$C_3$ alkoxy, wherein the $C_1$-$C_3$ alkyl and alkoxy groups are themselves optionally substituted with up to 6 fluorine atoms.

$R^6$ can be optionally substituted aryl, optionally substituted heteroaryl, optionally substituted O-aryl or optionally substituted O-heteroaryl. $R^6$ can be phenyl.

$R^7$ can be H, optionally substituted $C_1$-$C_6$ alkyl, $CONR^{10}R^{11}$, $OCONR^{10}R^{11}$, $OCOR^{10}$, $OCOOR^{10}$, $COOR^{10}$ or $OR^{12}$. $R^7$ can be $OCONR^{10}R^{11}$, $COOR^{10}$ or $OR^{12}$; wherein $R^{10}$ and $R^{11}$ are $C_2$-$C_6$ alkyl where any one atom in the $C_2$-$C_6$ alkyl group is replaced by a heteroatom selected from N, O and S, where $R^{10}$ and $R^{11}$ are optionally via $CH_2$ to form a ring.

$R^7$ can be 0

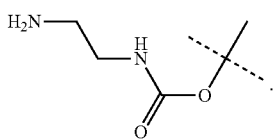

$R^7$ can be

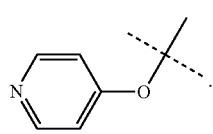

$R^7$ can be

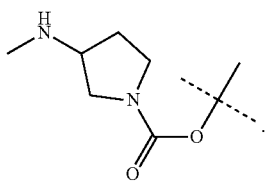

$R^8$ can be H, $CONR^{10}R^{11}$ or $COOR^{10}$. $R^8$ can be hydrogen. $R^8$ can be H.

$R^8$ can be

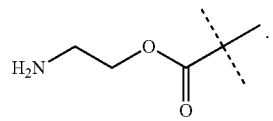

$R^{10}$ can be H, optionally substituted $C_1$-$C_6$ alkyl or optionally substituted $C_2$-$C_6$ alkyl where any one atom in the $C_2$-$C_6$ alkyl group is replaced by a heteroatom selected from N, O and S. $R^{10}$ can be hydrogen. $R^{10}$ can be H. $R^{10}$ can be —$CH_2CH_2NH_2$.

$R^{11}$ can be H, optionally substituted $C_1$—C alkyl or optionally substituted $C_2$-$C_6$ alkyl where any one atom in the $C_2$-$C_6$ alkyl group is replaced by a heteroatom selected from N, O and S. $R^{11}$ can be hydrogen. $R^{11}$ can be H. $R^{11}$ can be —$CH_2CH_2NH_2$.

$R^{10}$ and $R^{11}$ can be joined to form a ring.

$R^{12}$ can be optionally substituted aryl or optionally substituted heteroaryl. $R^{12}$ can be pyridyl.

The moiety formed by Z and m can be selected from:

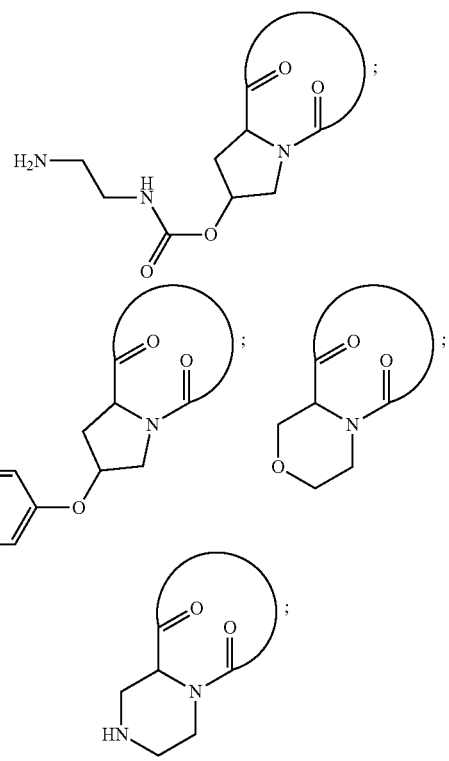

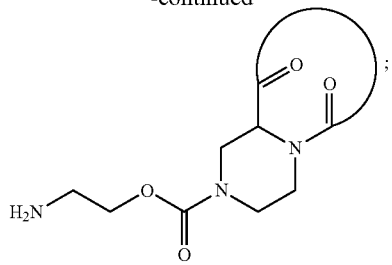

The moiety formed by Z and m can be

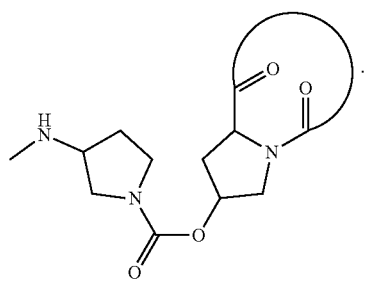

The moiety formed by Z and m can be

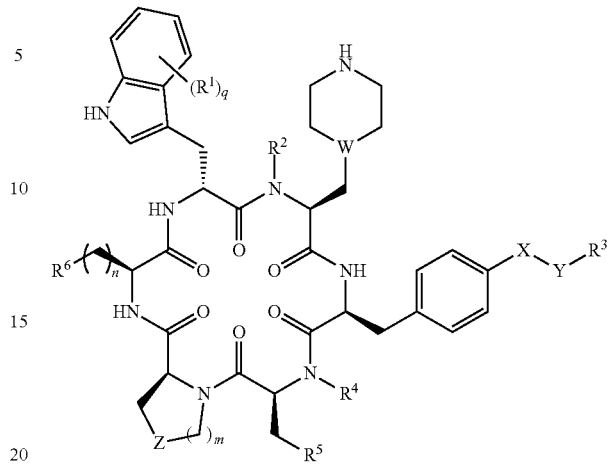

(1a)

or a salt thereof, wherein W, X, Y, Z, m, n, q, $R^1$, $R^2$, $R^3$, $R^4$, $R^5$ and $R^6$ are as defined above.

Particular compounds of the invention also include compounds of formula (1b):

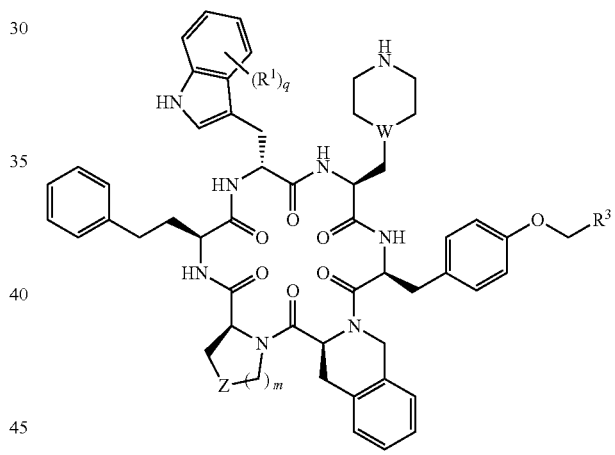

(1b)

or a salt thereof, wherein W, Z, m, q, $R^1$ and $R^3$ are as defined above.

The compound can be selected from any one of Examples 1 to 79 shown in Table 1.

Specific examples of compounds include compounds having somatostatin receptor agonist activity.

Specific examples of compounds include compounds having $SST_5$ receptor agonist activity.

Specific examples of compounds include compounds that exhibit selectivity towards the $SST_5$ receptor compared to the $SST_2$ receptor.

The compounds of the invention may be used in a pharmaceutical composition comprising a compound of the invention and a pharmaceutically acceptable excipient.

The compounds of the invention may be used in medicine.

The compounds of the invention may be used in the treatment of disorders associated with somatostatin receptors.

The compounds of the invention may be used in the treatment of disorders associated with the $SST_5$ receptor.

Particular compounds of the invention also include compounds of formula (1a):

The compounds of the invention may be used in the treatment of Cushing's Disease, Cushing's Syndrome, Acromegaly, Neuroendocrine tumours (inc. Carcinoid tumours), Thyrotropinomas, Prolactinomas, Non-functioning pituitary adenomas, Nelson's syndrome, Congenital hyperinsulinism, Post-gastric bypass hypoglycaemia, Dumping syndrome, Hyperinsulinemic obesity, Insulinoma, Polycystic kidney disease, Polycystic liver disease, Portal hypertension, Ascites, Pancreatic cancer, Pancreatic fistula, Acute or chronic pancreatitis, Hepatocellular carcinoma, Irritable bowel syndrome/disease, Headache disorders (inc. migraine, cluster headache, tension-type headache).

Definitions

In this application, the following definitions apply, unless indicated otherwise.

The term "alkyl", "aryl", "halo", "alkoxy", "cycloalkyl" and "heteroaryl" are used in their conventional sense (e.g. as defined in the IUPAC Gold Book) unless indicated otherwise.

The term "treatment", in relation to the uses of any of the compounds described herein, including those of the formula (1), formula (1a) or formula (1b), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disorder, disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of the formula (1) as defined above together with at least one pharmaceutically acceptable excipient.

The composition may be a composition suitable for injection. The injection may be intra-venous (IV) or subcutaneous. The composition may be supplied in a sterile buffer solution or as a solid which can be suspended or dissolved in sterile buffer for injection.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

Suitable formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the formula (1) will generally be presented in unit dosage form and, as such, will typically contain sufficient compound to provide a desired level of biological activity.

For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1 to 79

The compounds of Examples 1 to 79 shown in Table 1 below have been prepared. Their NMR and LCMS properties and the methods used to prepare them are set out in Table 2 and 3. The starting materials for each of the Examples are commercial unless indicated.

TABLE 1
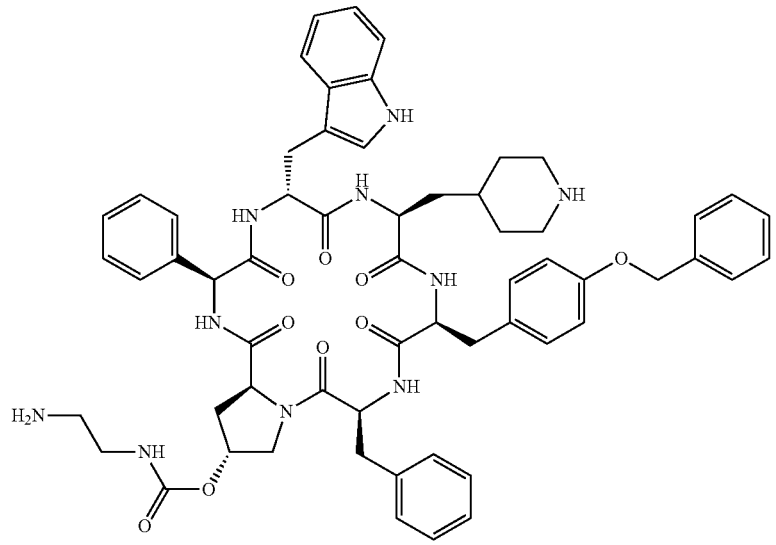
Example 1
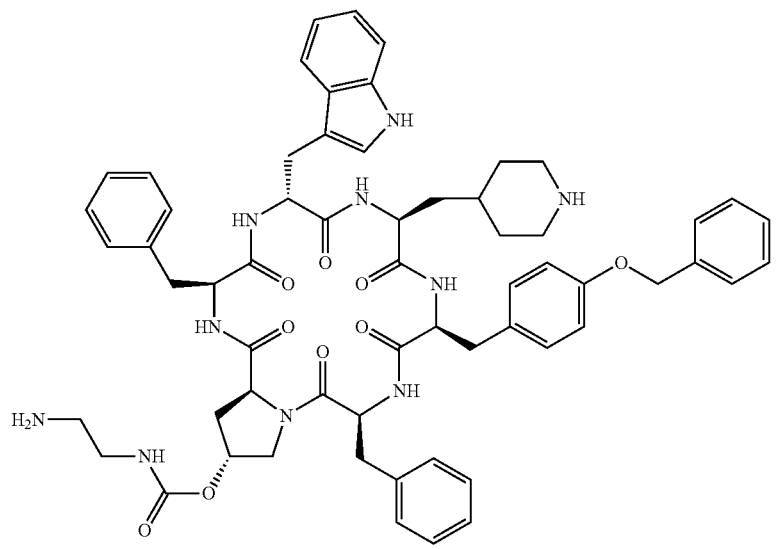
Example 2

TABLE 1-continued
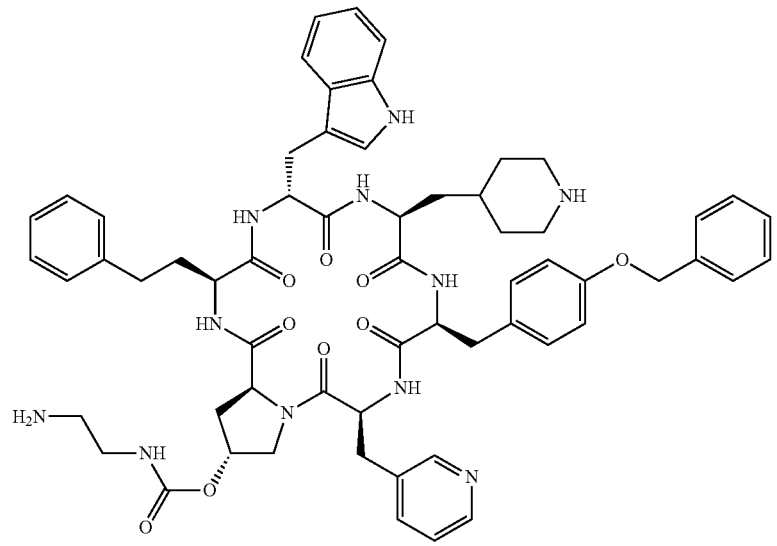
Example 3
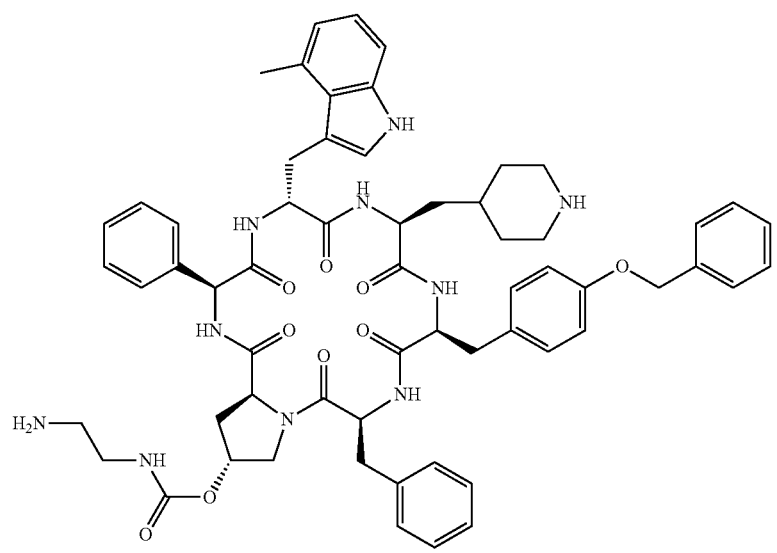
Example 4

TABLE 1-continued
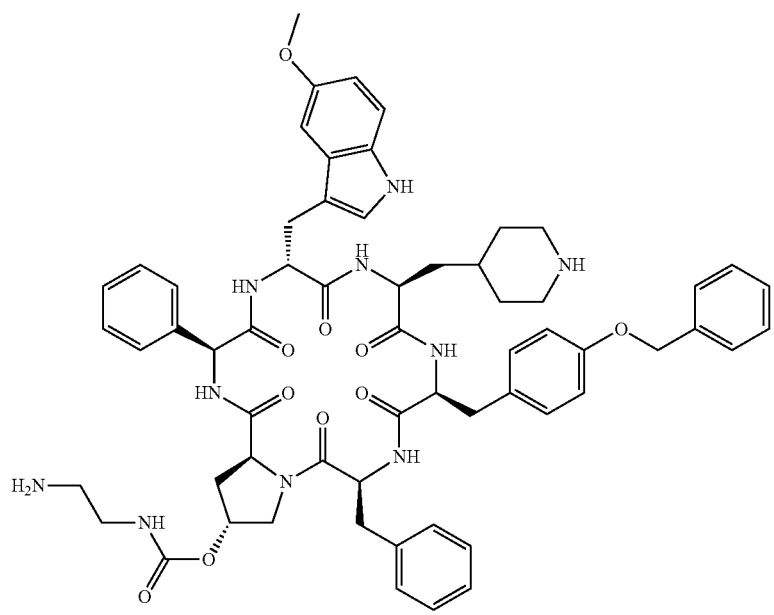
Example 5
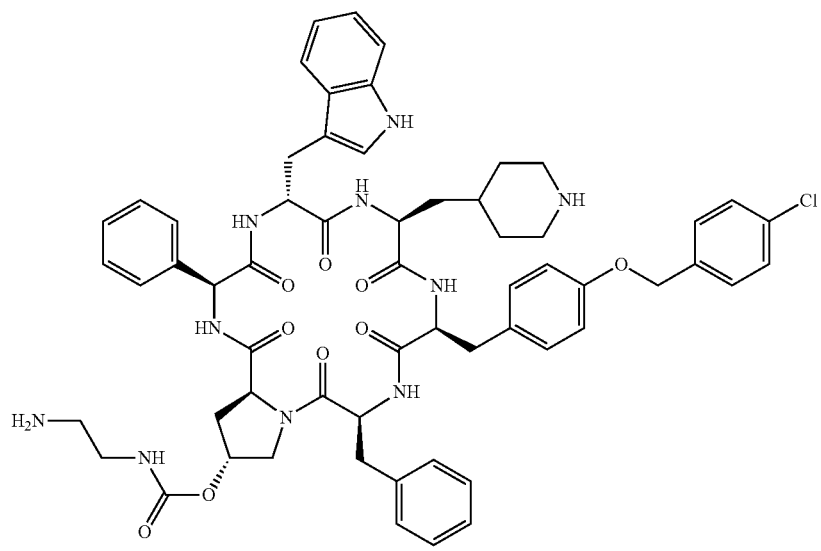
Example 6

TABLE 1-continued
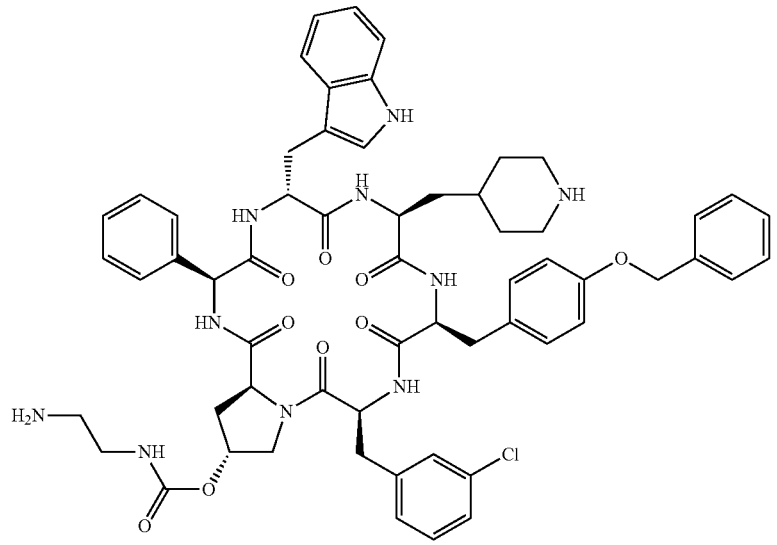
Example 7
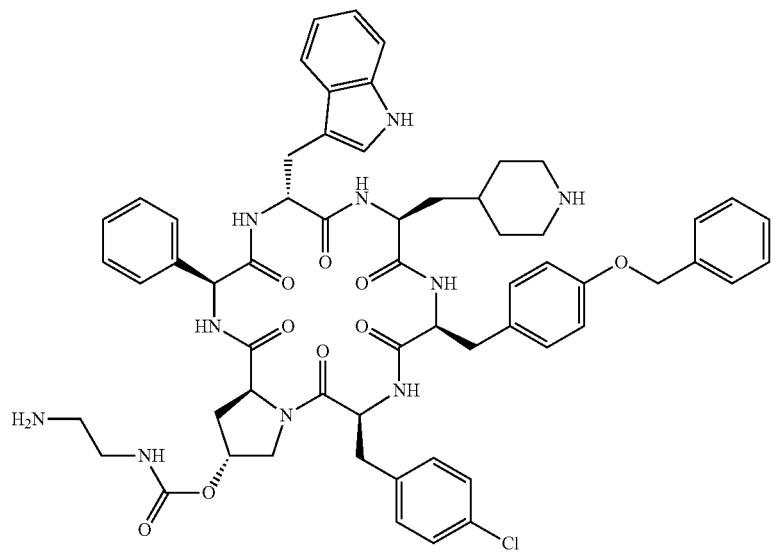
Example 8

TABLE 1-continued
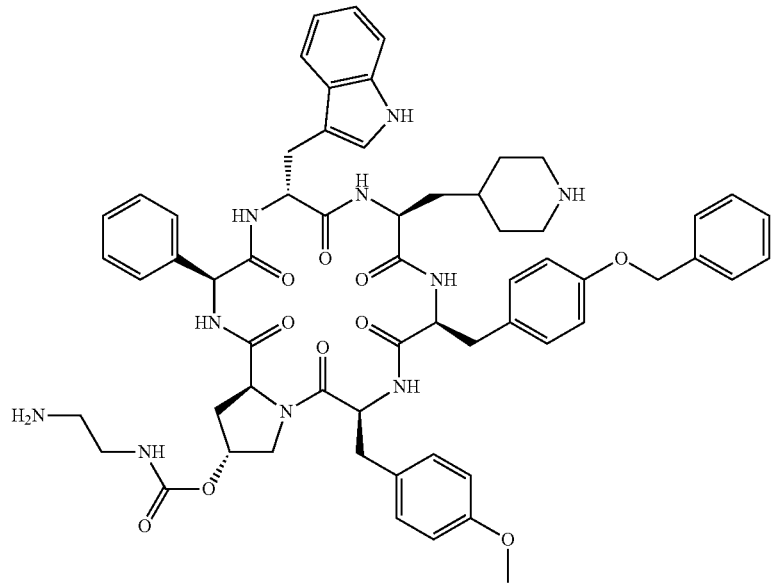 [SMILES: NCCNC(=O)O[C@@H]1C[C@H]2C(=O)N[C@@H](c3ccccc3)C(=O)N[C@H](Cc3c[nH]c4ccccc34)C(=O)N[C@@H](CC3CCNCC3)C(=O)N[C@@H](Cc3ccc(OCc4ccccc4)cc3)C(=O)N[C@@H](Cc3ccccc3)C(=O)N2C1]
Example 9
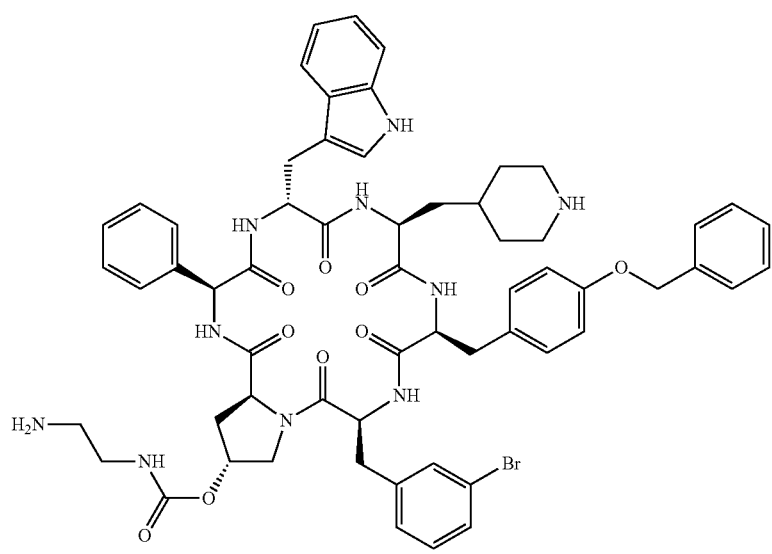
Example 10

TABLE 1-continued
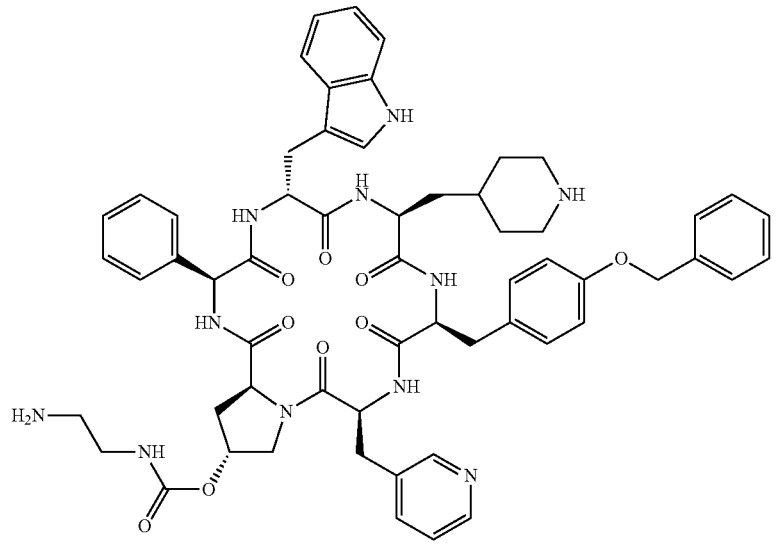
Example 11
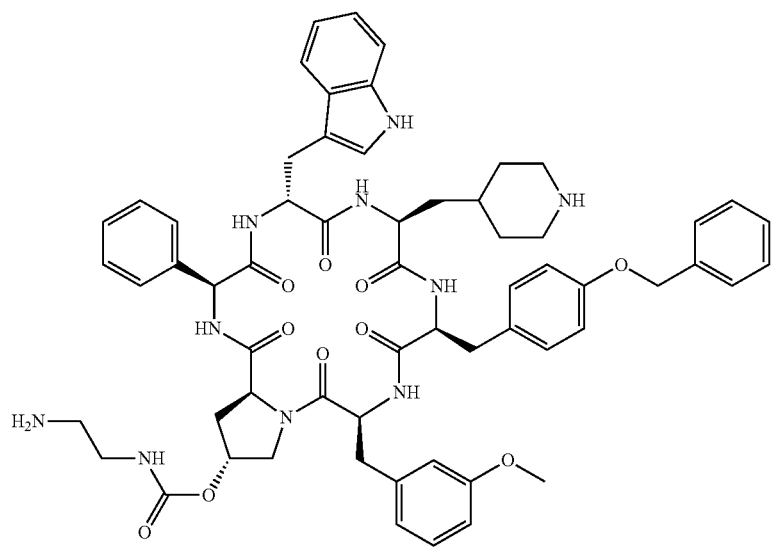
Example 12

TABLE 1-continued
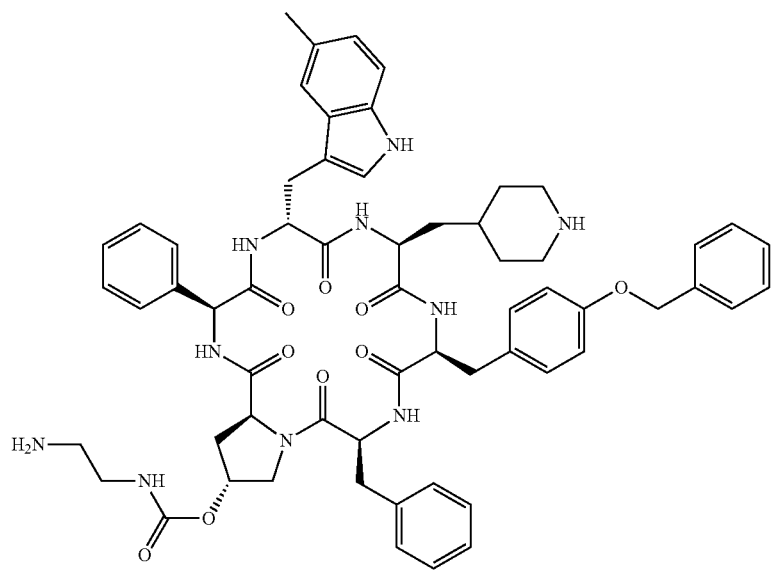
Example 13
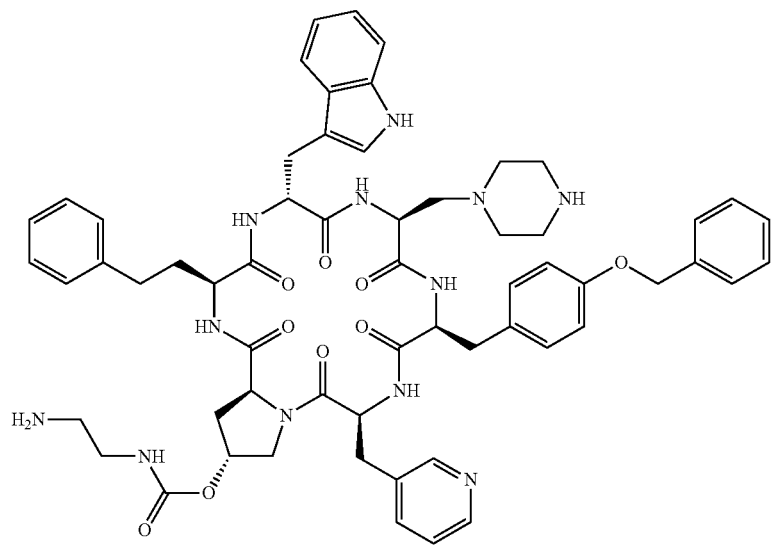
Example 14

TABLE 1-continued
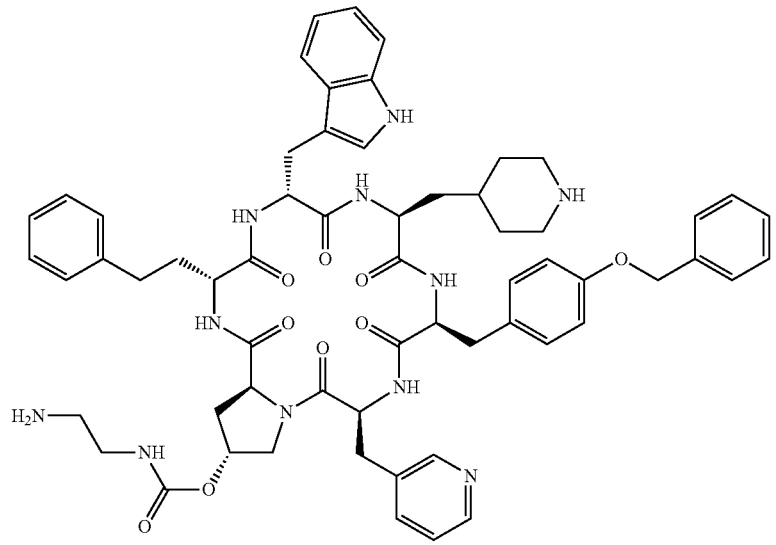
Example 15
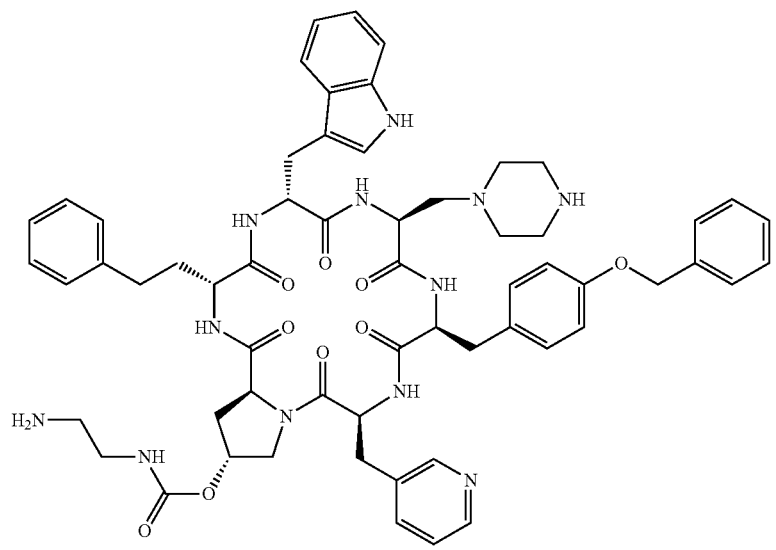
Example 16

TABLE 1-continued
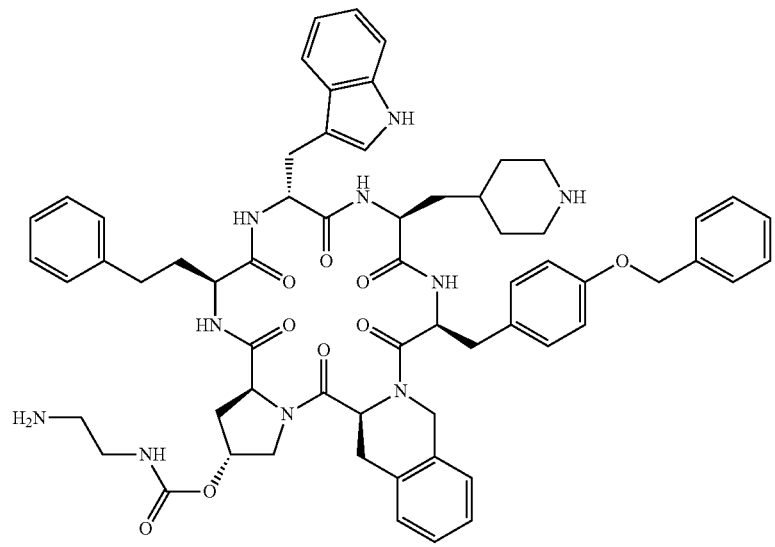
Example 17
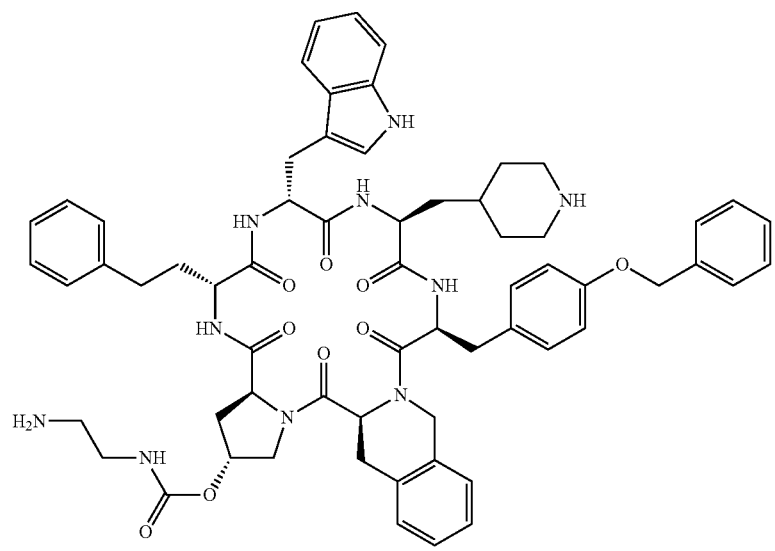
Example 18

TABLE 1-continued
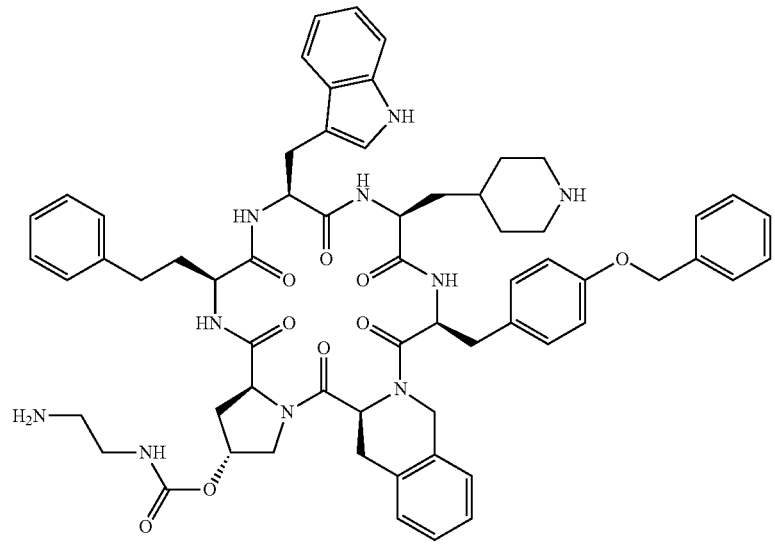
Example 19
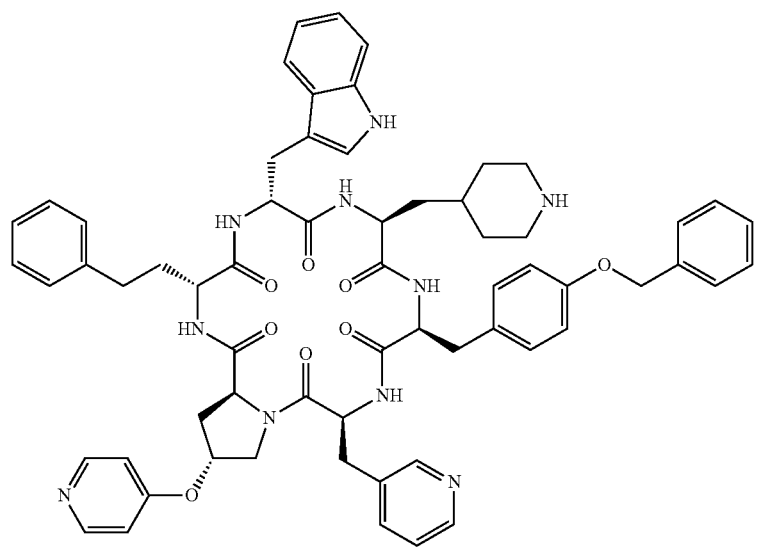
Example 20

TABLE 1-continued
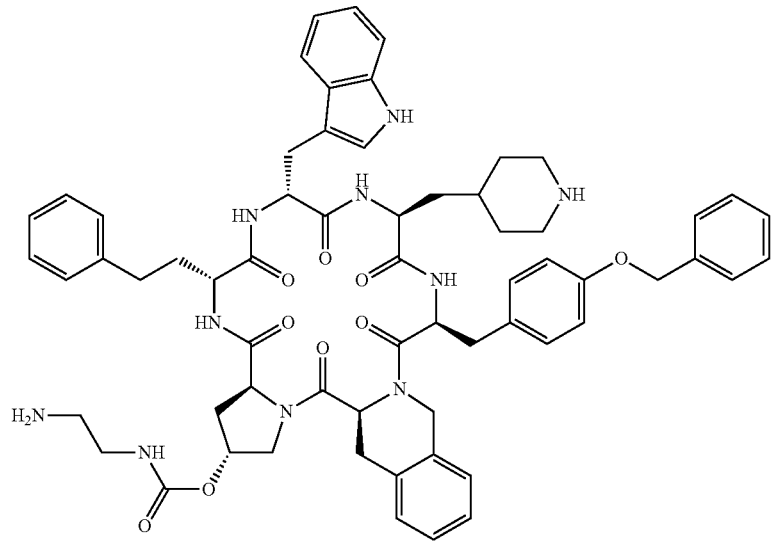
Example 21
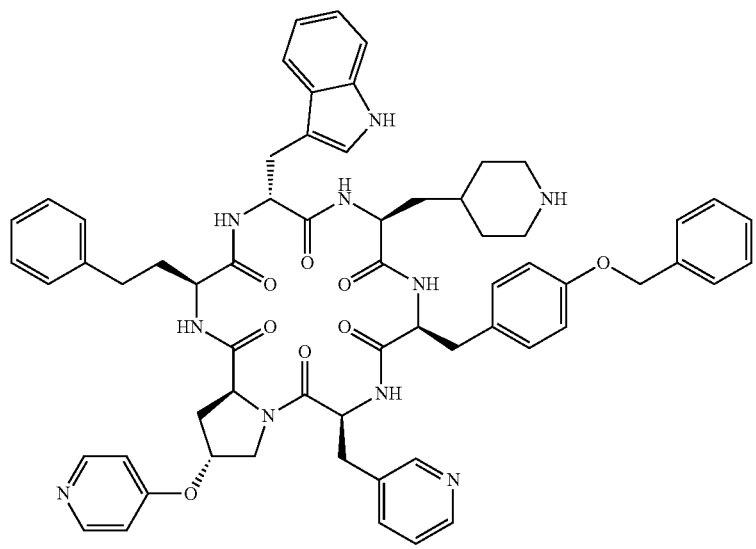
Example 22

TABLE 1-continued
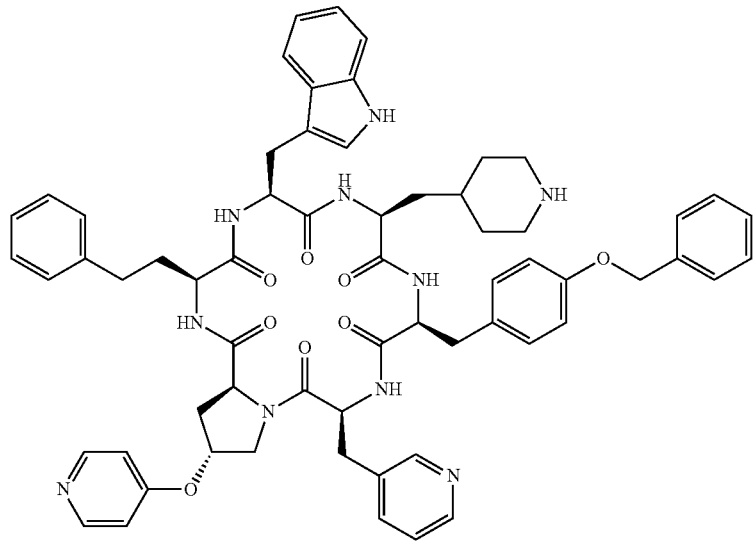
Example 23
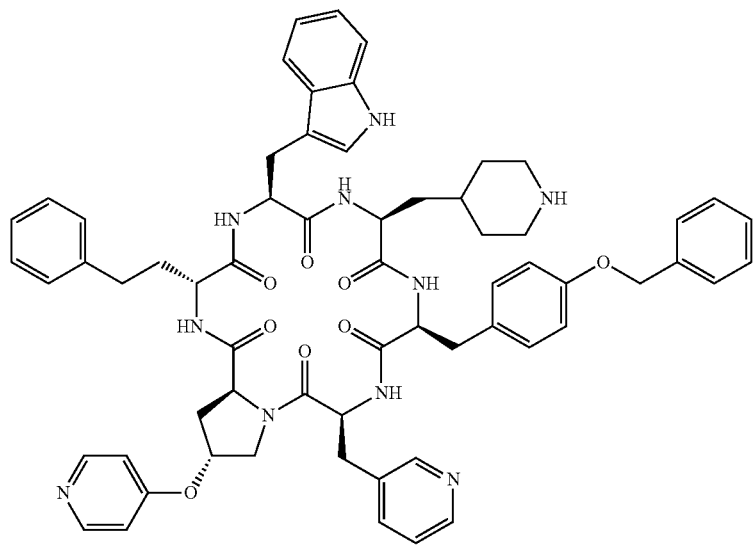
Example 24

TABLE 1-continued
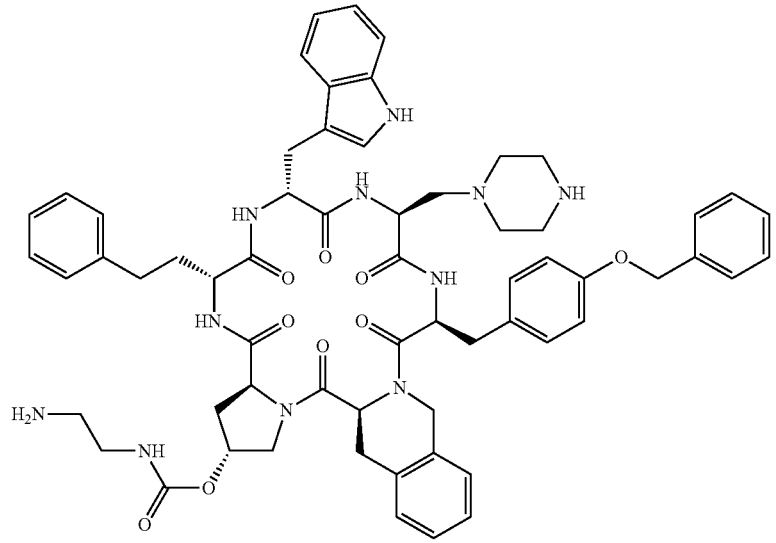
Example 25
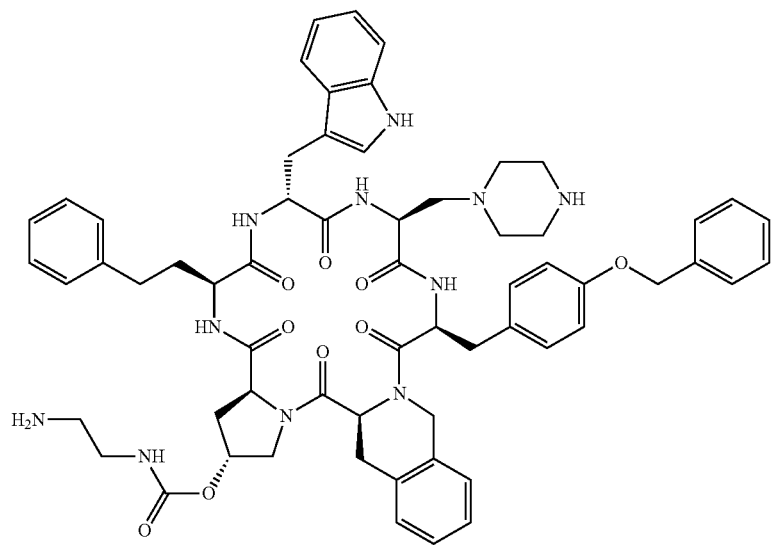
Example 26

TABLE 1-continued
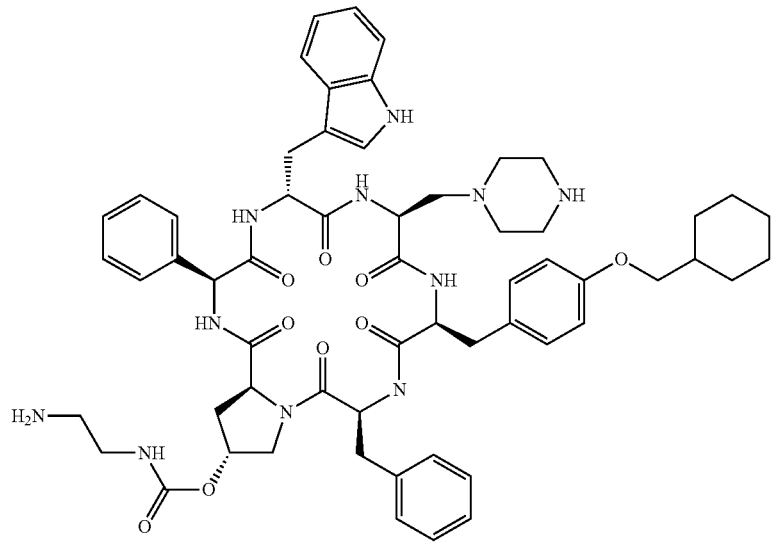
Example 27
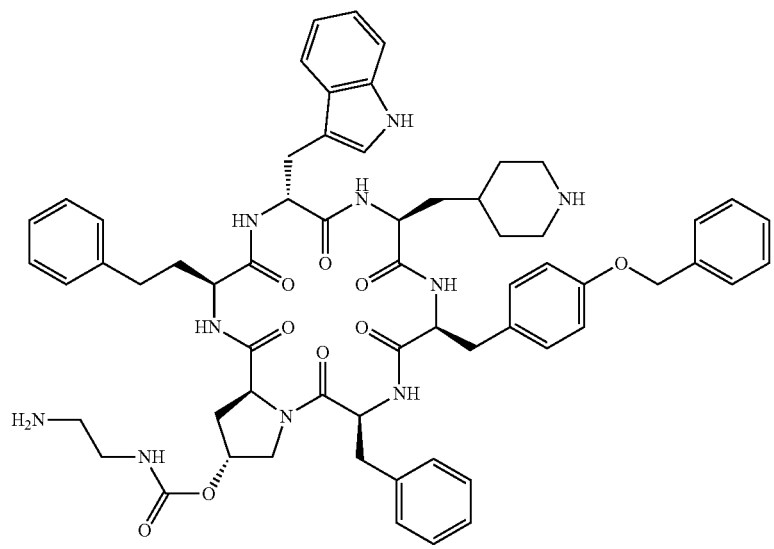
Example 28

TABLE 1-continued
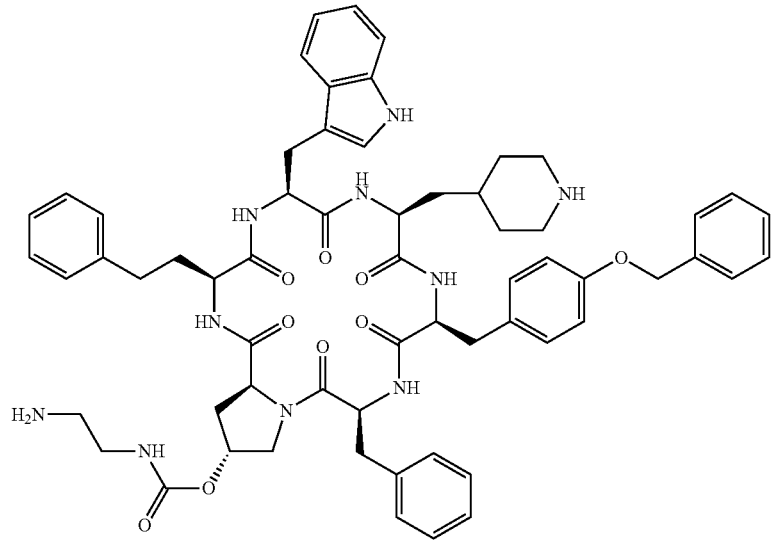
Example 29
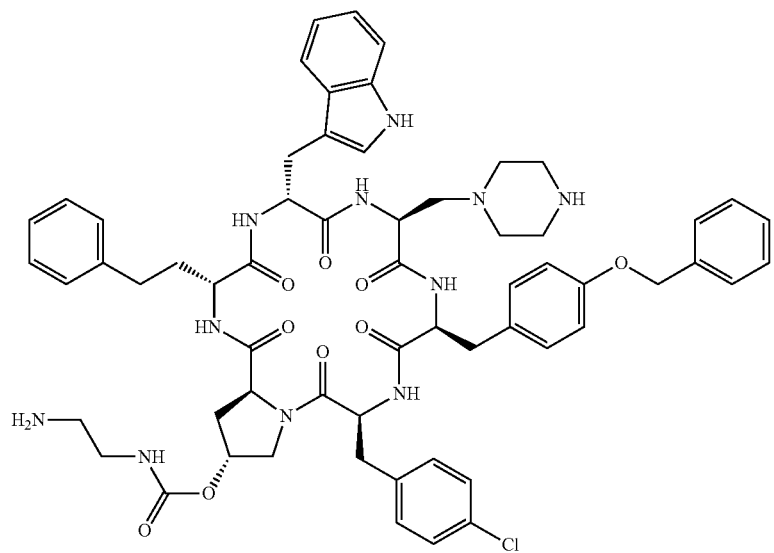
Example 30

TABLE 1-continued
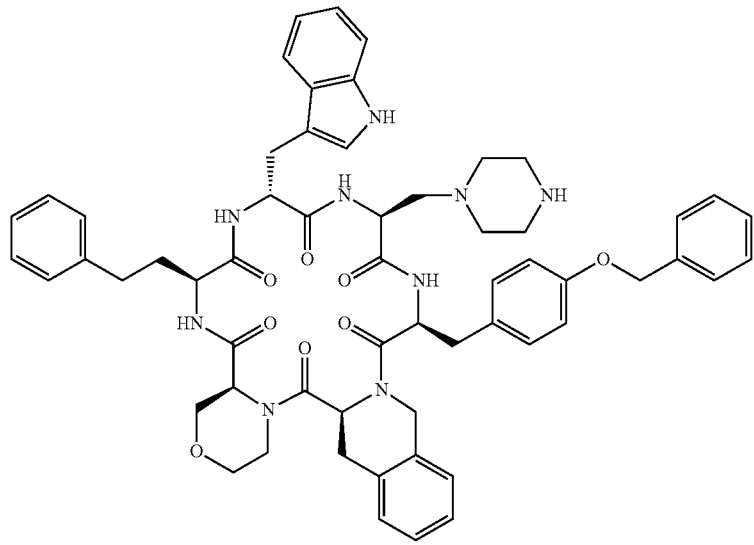
Example 31
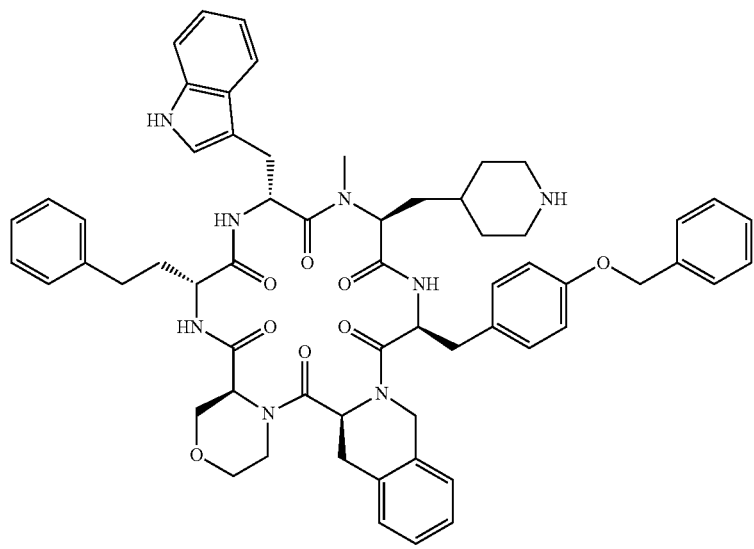
Example 32

TABLE 1-continued
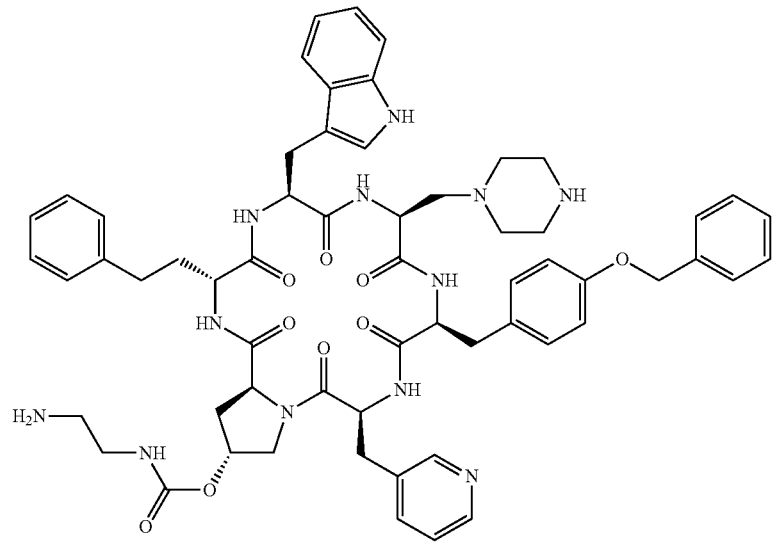
Example 33
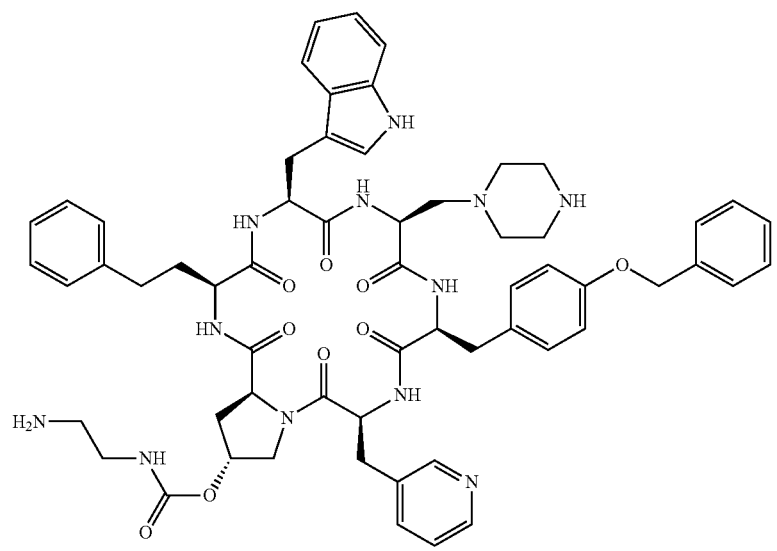
Example 34

TABLE 1-continued
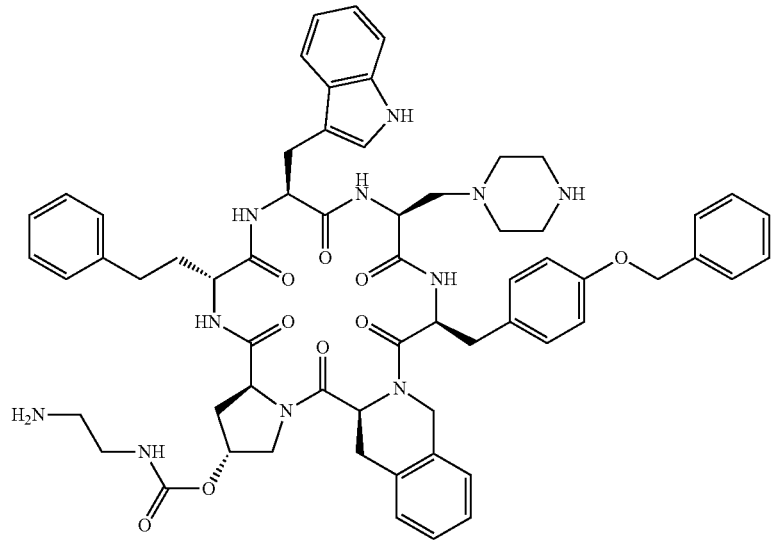
Example 35
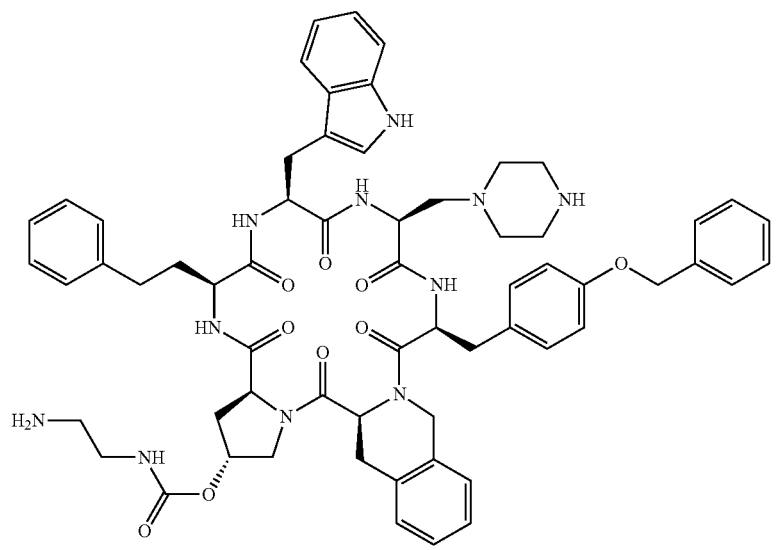
Example 36

TABLE 1-continued
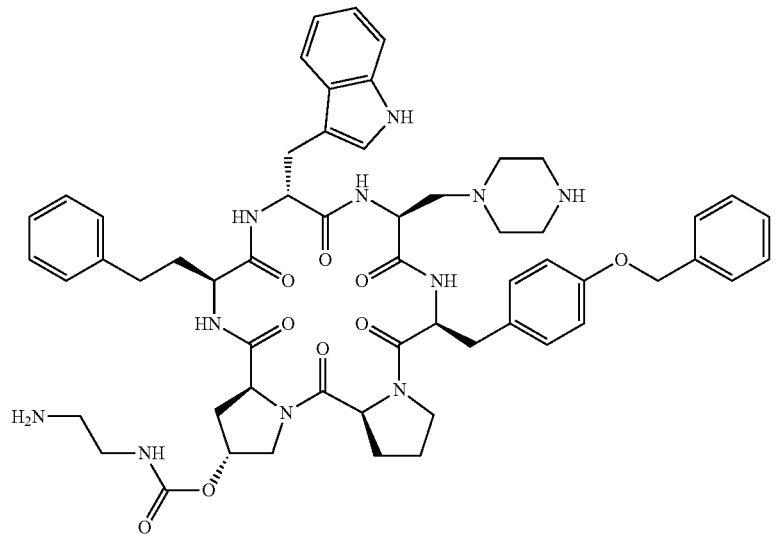
Example 37
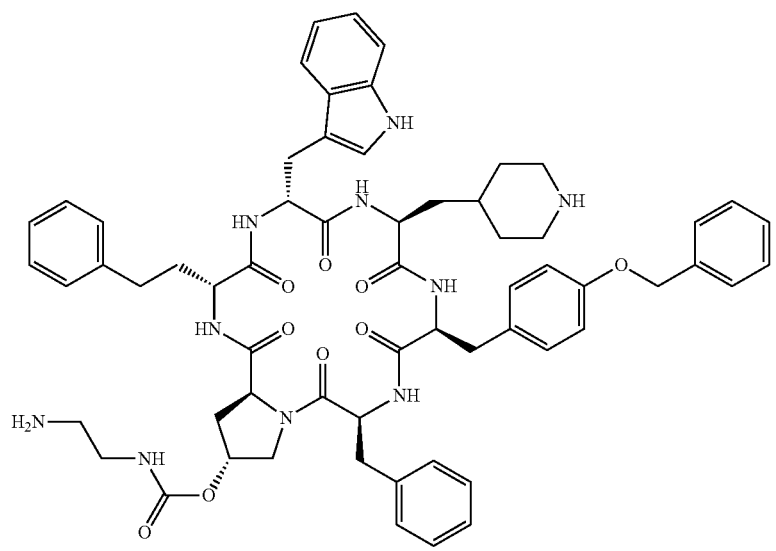
Example 38

TABLE 1-continued
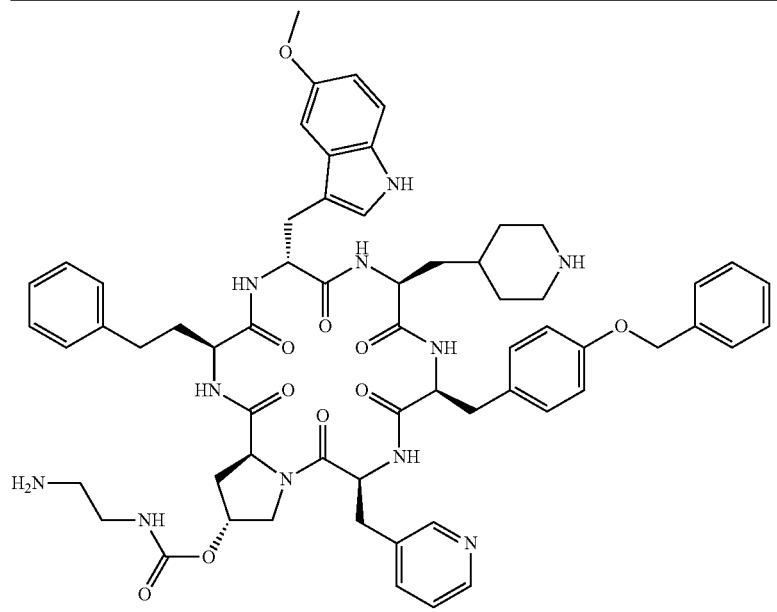
Example 39
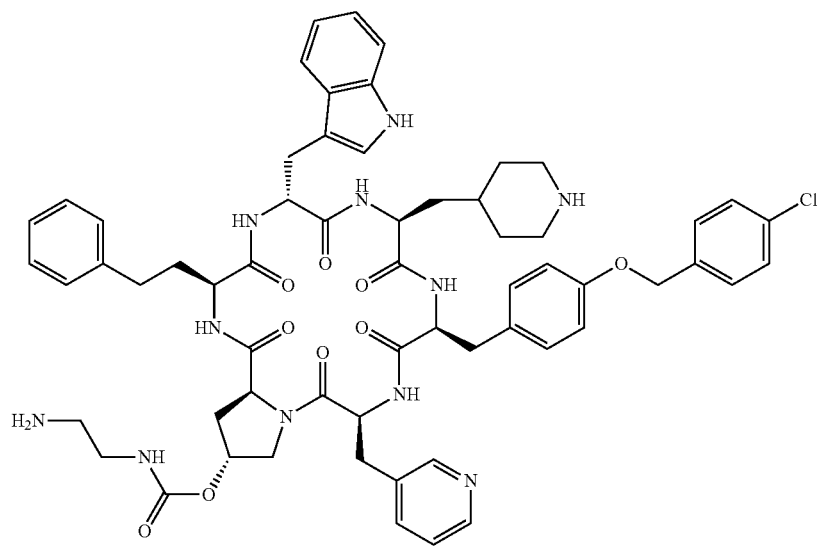
Example 40

TABLE 1-continued
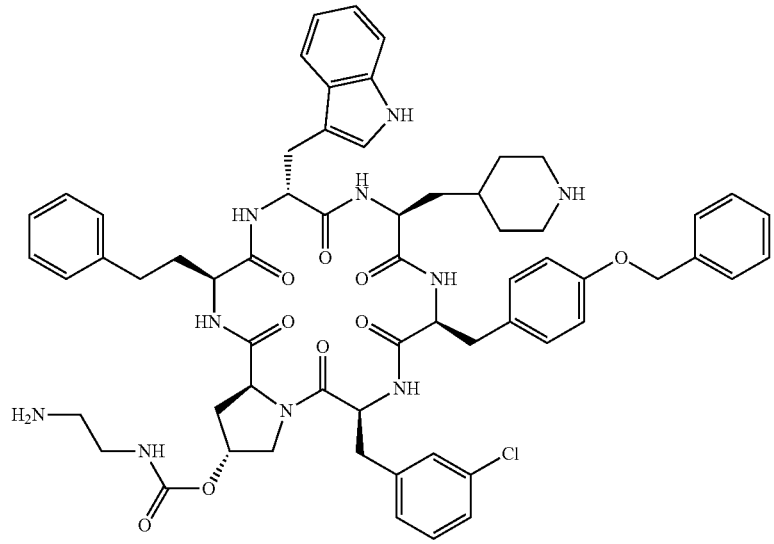
Example 41
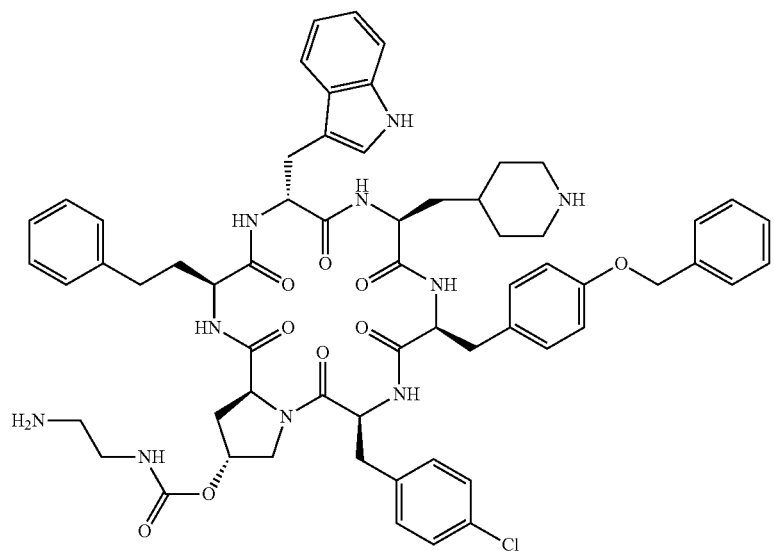
Example 42

TABLE 1-continued
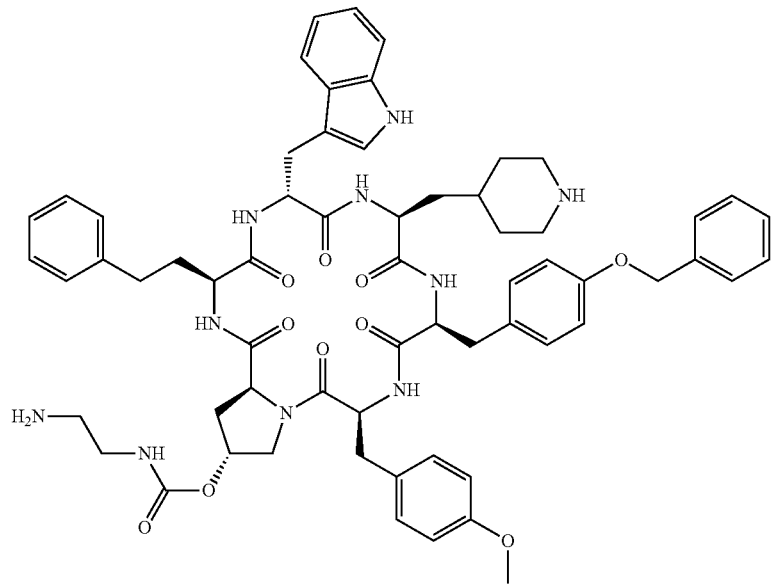
Example 43
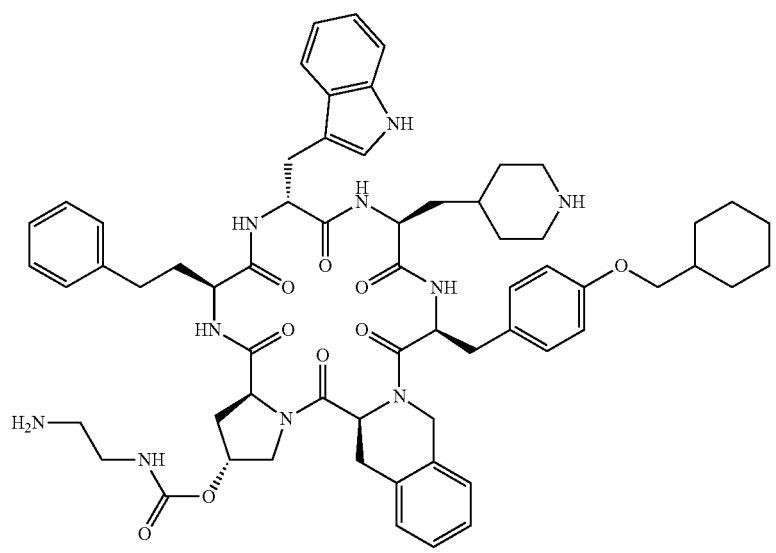
Example 44

TABLE 1-continued
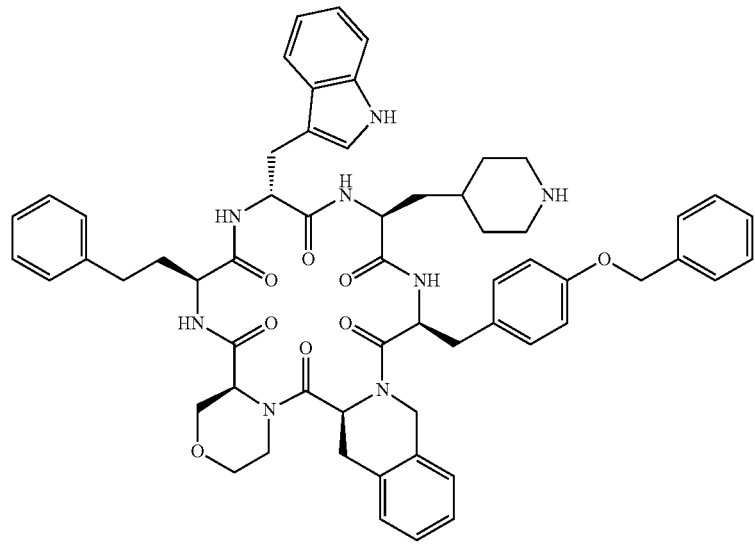
Example 45
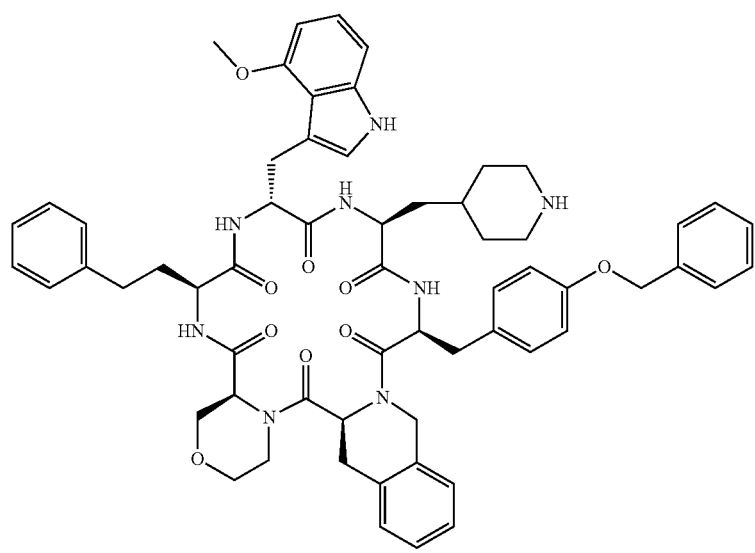
Example 46

TABLE 1-continued
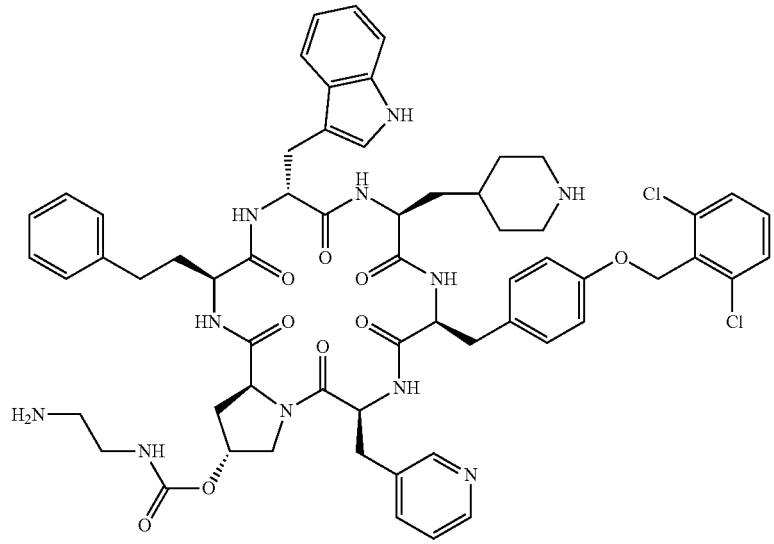
Example 47
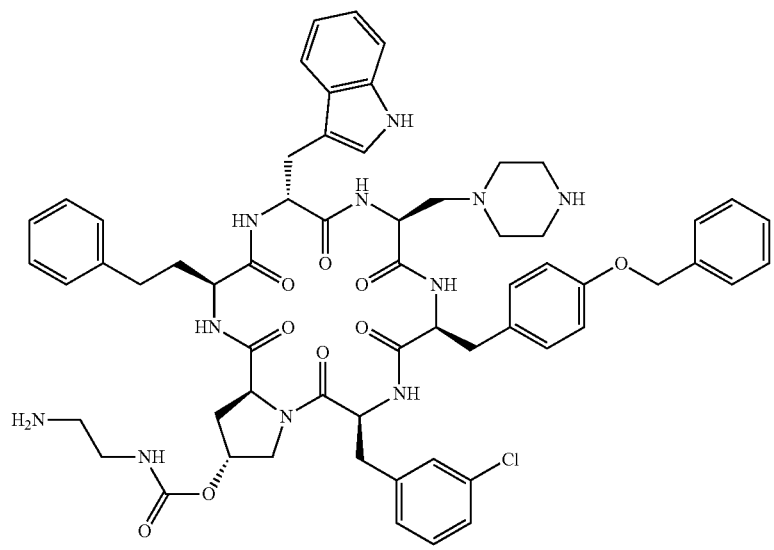
Example 48

TABLE 1-continued
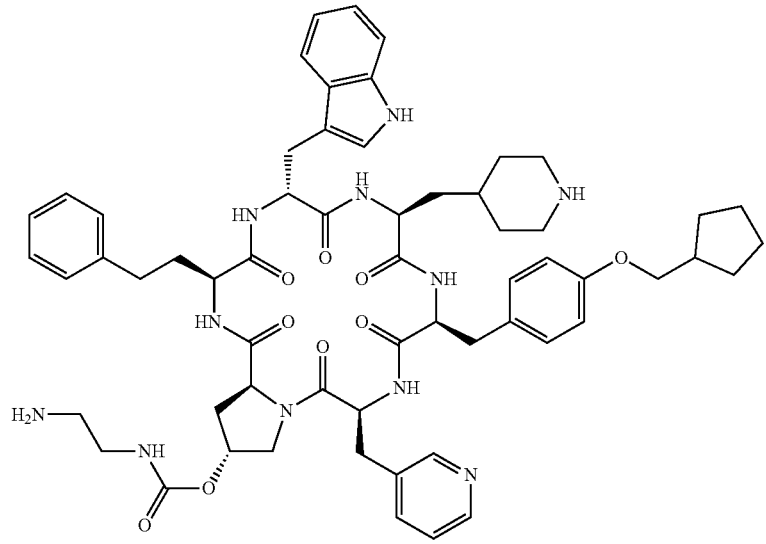
Example 49
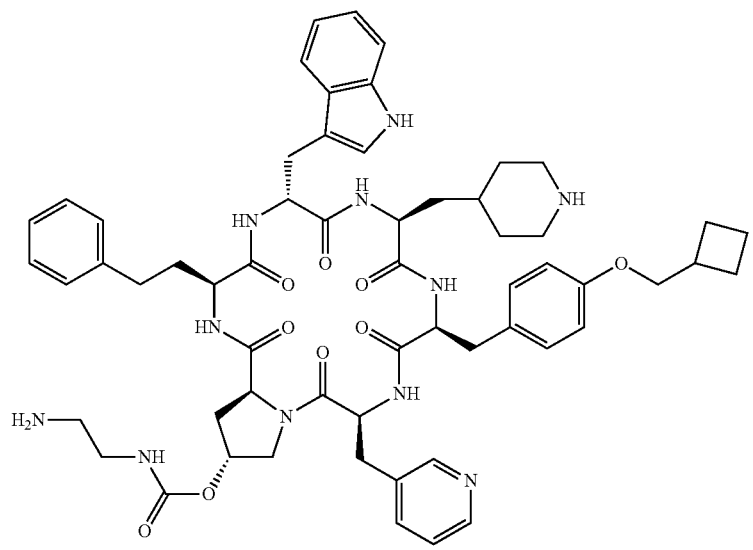
Example 50

TABLE 1-continued
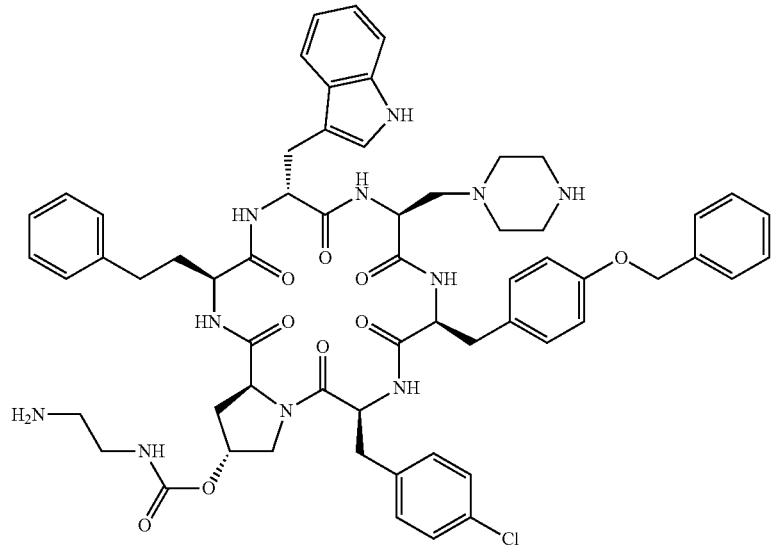
Example 51
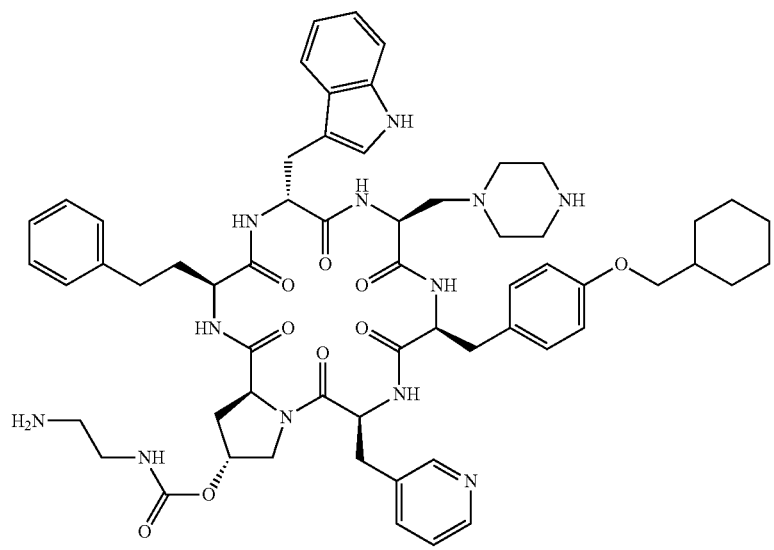
Example 52

TABLE 1-continued
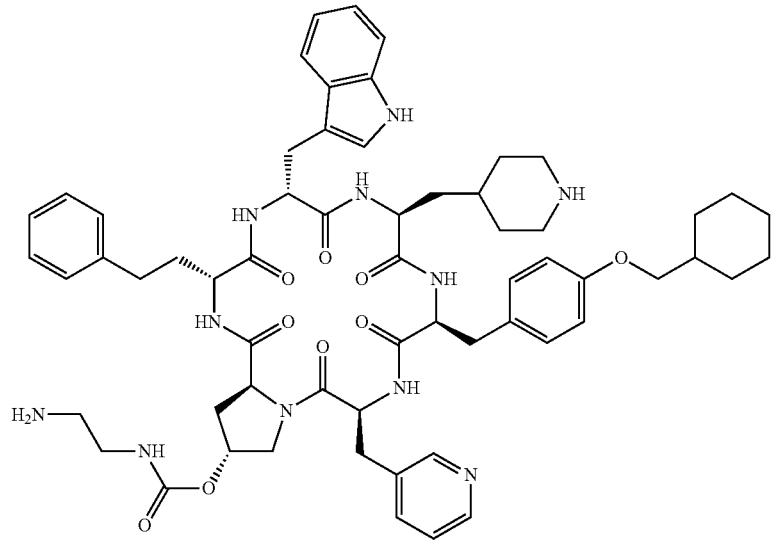
Example 53
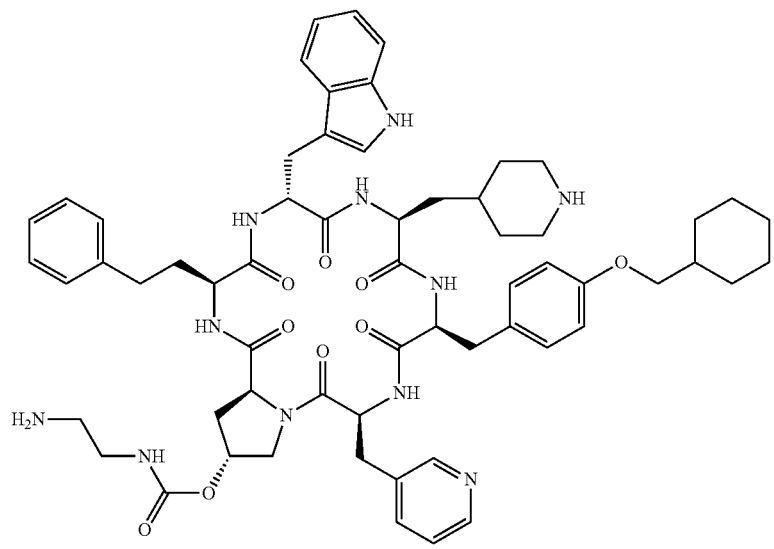
Example 54

TABLE 1-continued
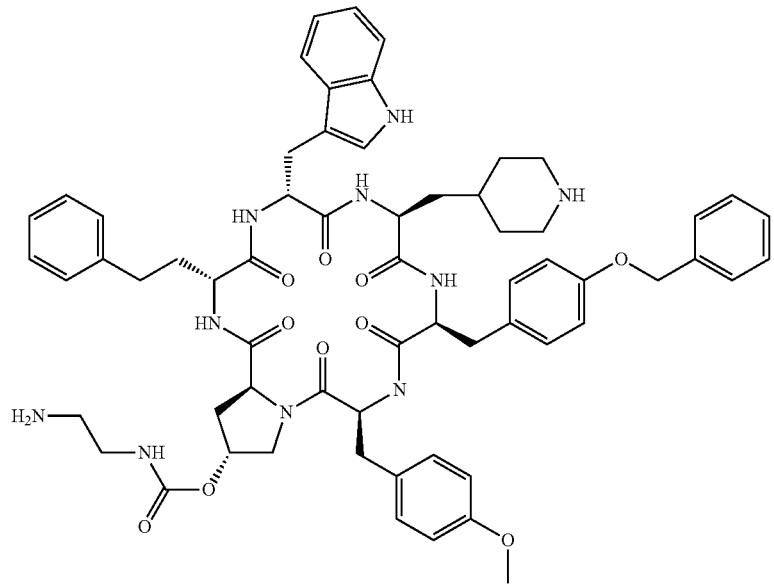 [SMILES: NCCNC(=O)O[C@@H]1C[C@H]2C(=O)N[C@H](CCc3ccccc3)C(=O)N[C@H](Cc3c[nH]c4ccccc34)C(=O)N[C@@H](CN3CCNCC3)C(=O)N[C@@H](Cc3ccc(OCc4ccccc4)cc3)C(=O)N[C@@H](Cc3ccc(Cl)cc3)C(=O)N2C1]
Example 55
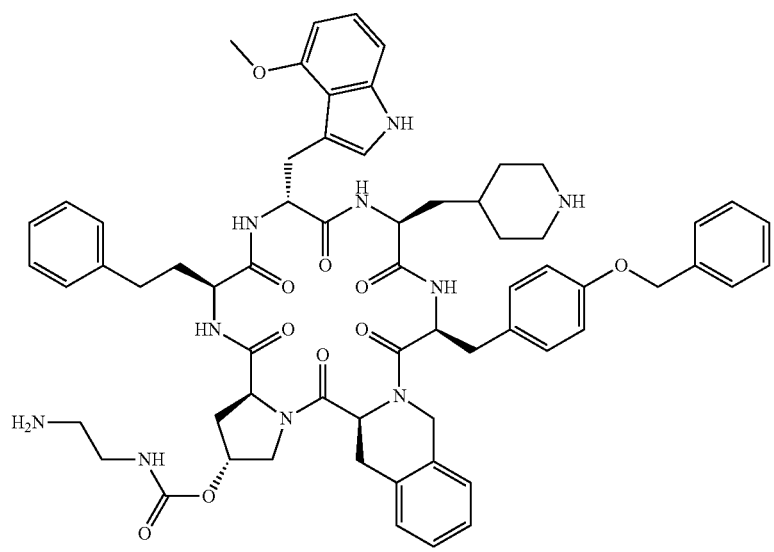
Example 56

TABLE 1-continued
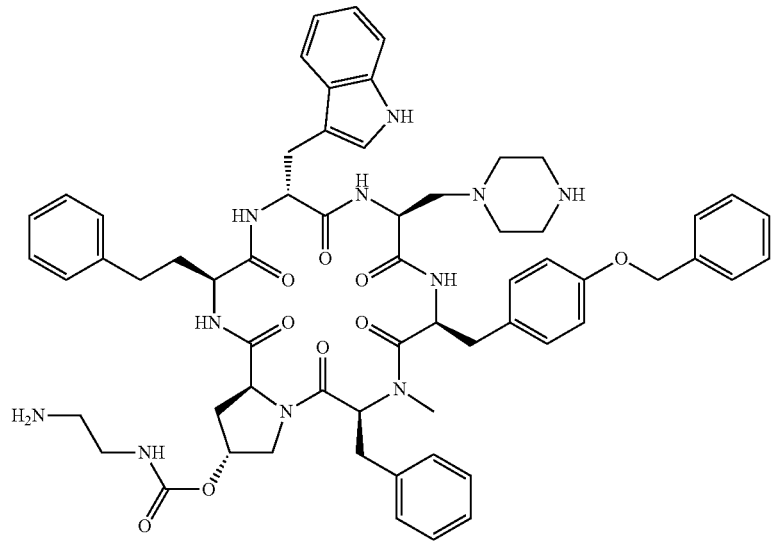
Example 57
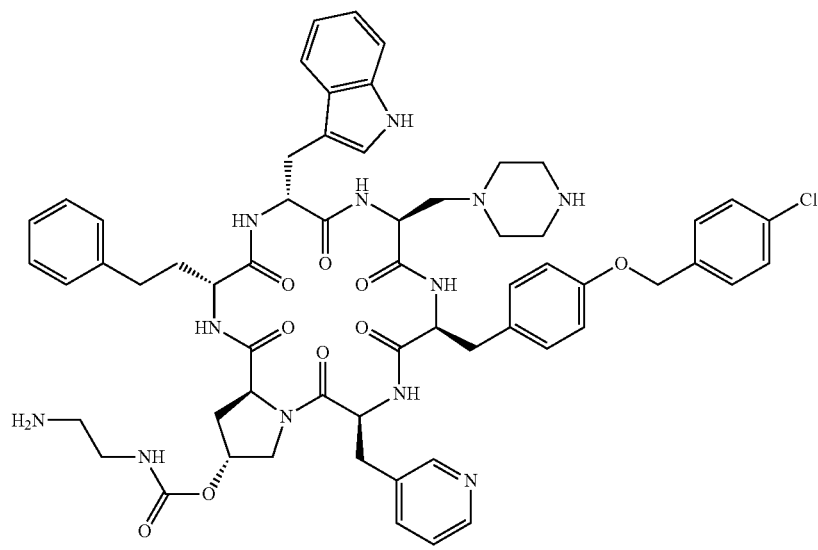
Example 58

TABLE 1-continued
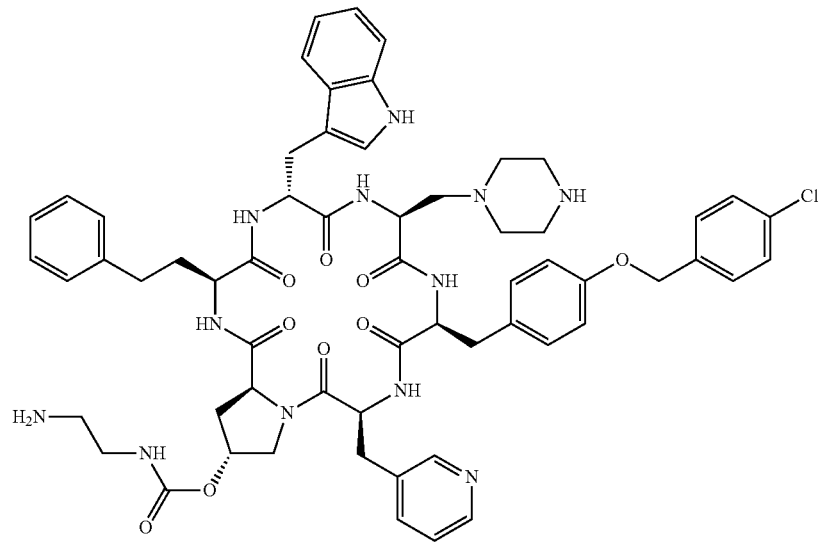
Example 59
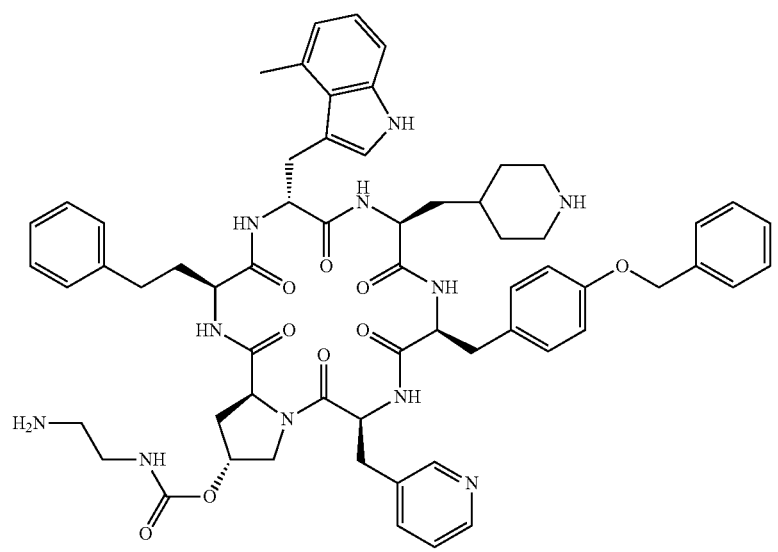
Example 60

TABLE 1-continued
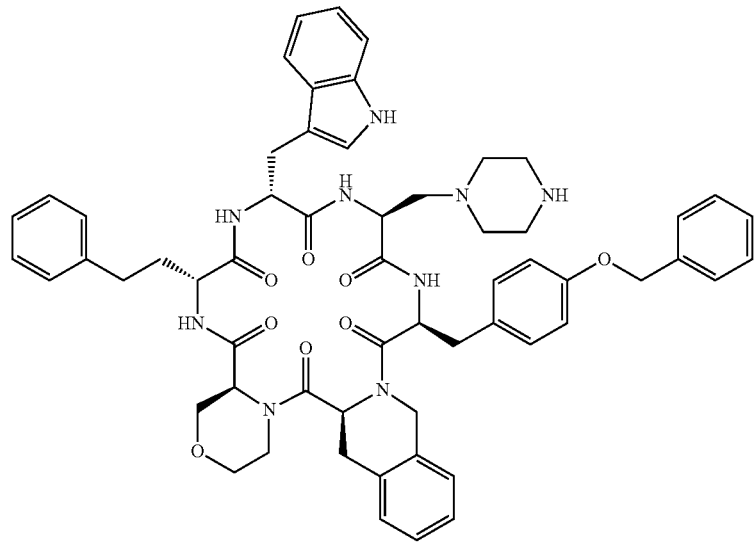
Example 61
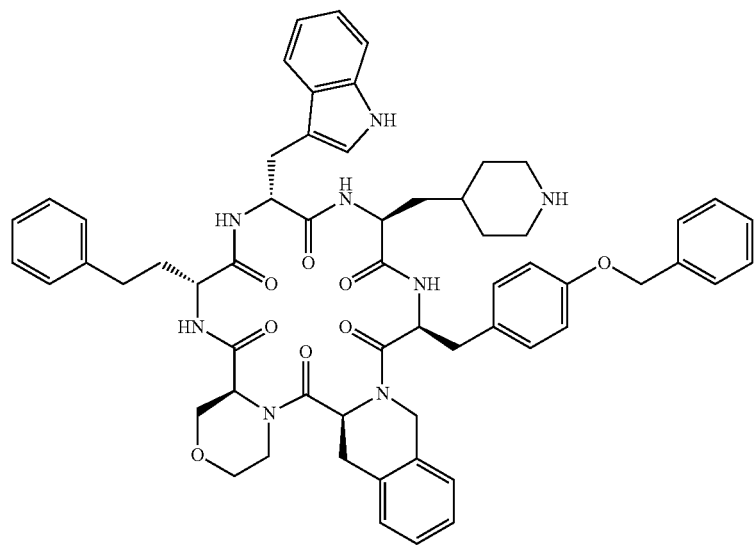
Example 62

TABLE 1-continued
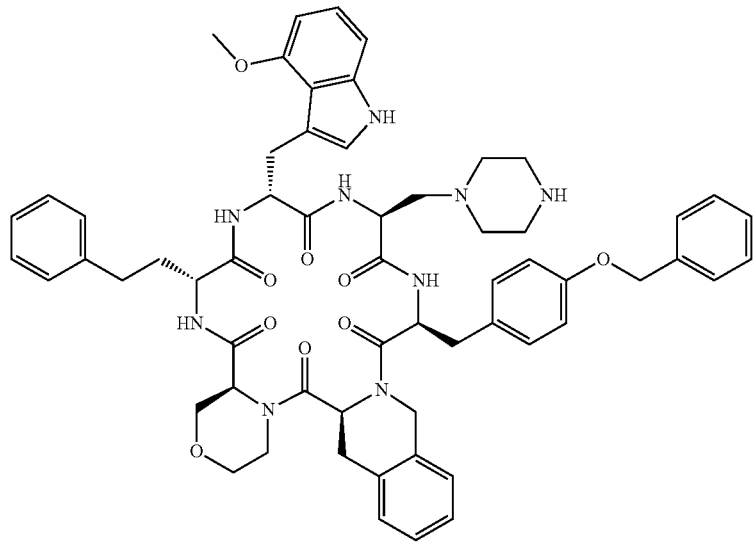
Example 63
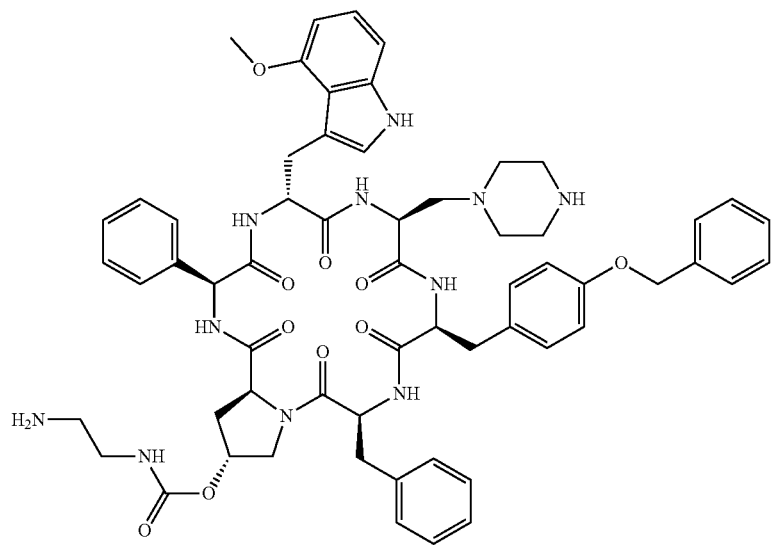
Example 64

TABLE 1-continued
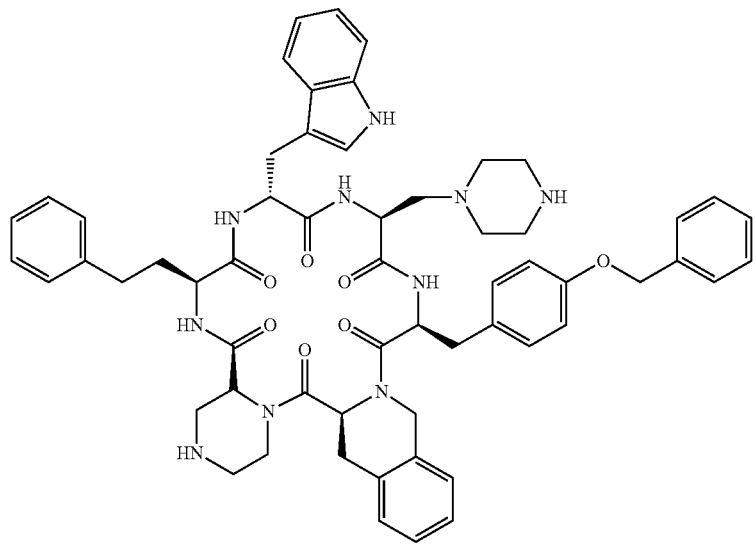
Example 65
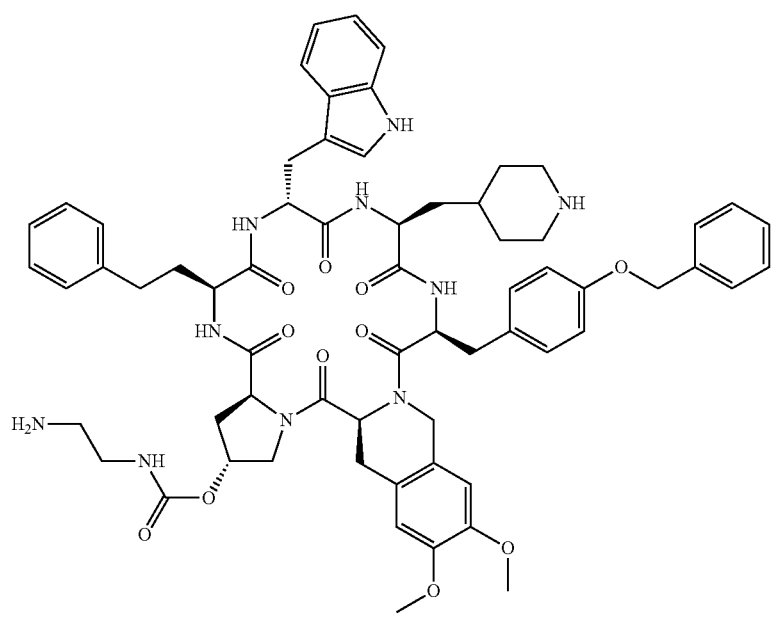
Example 66

TABLE 1-continued
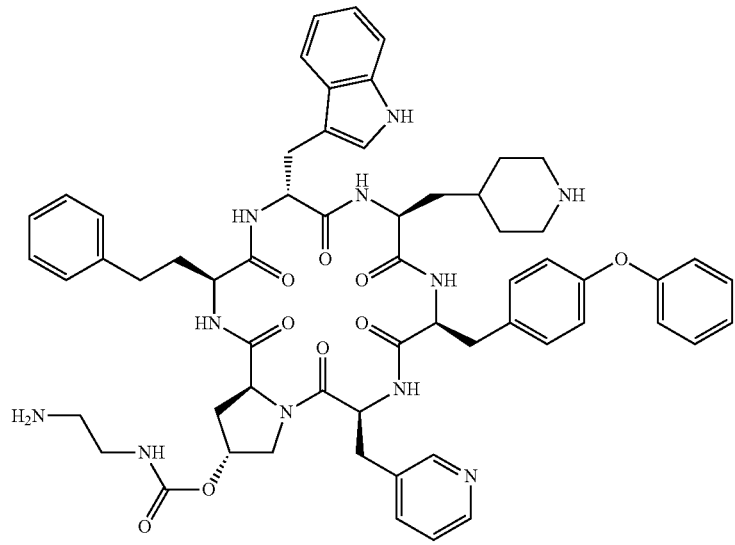
Example 67
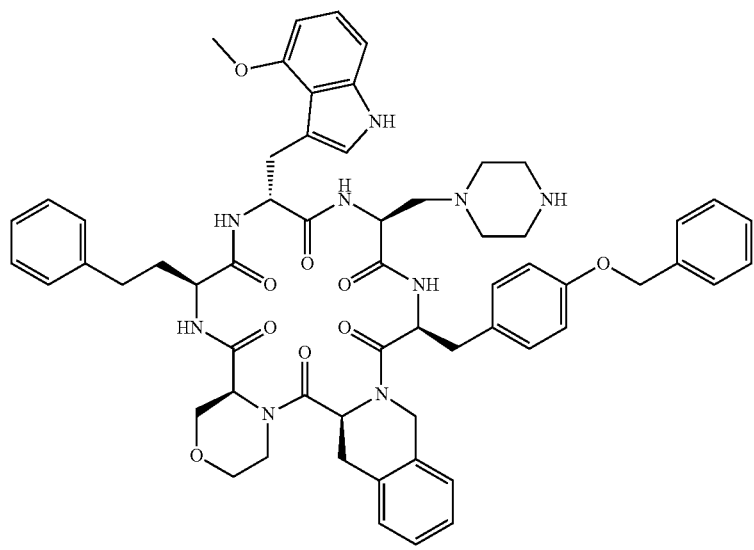
Example 68

TABLE 1-continued
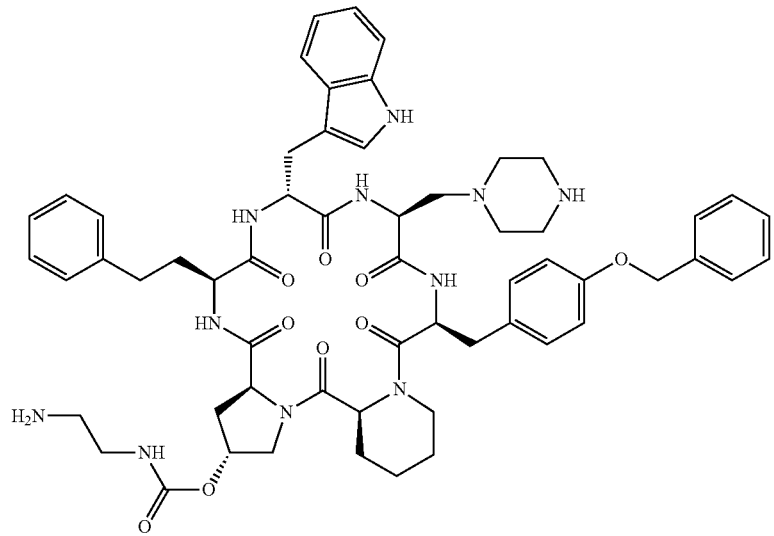
Example 69
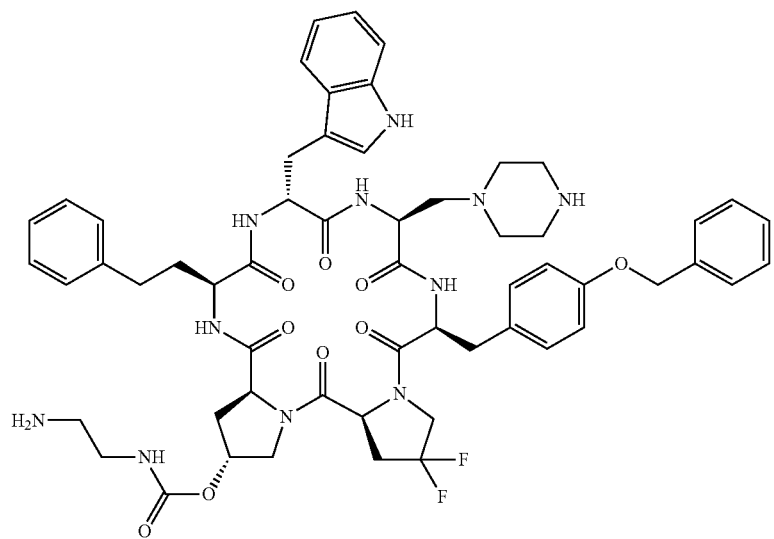
Example 70

TABLE 1-continued
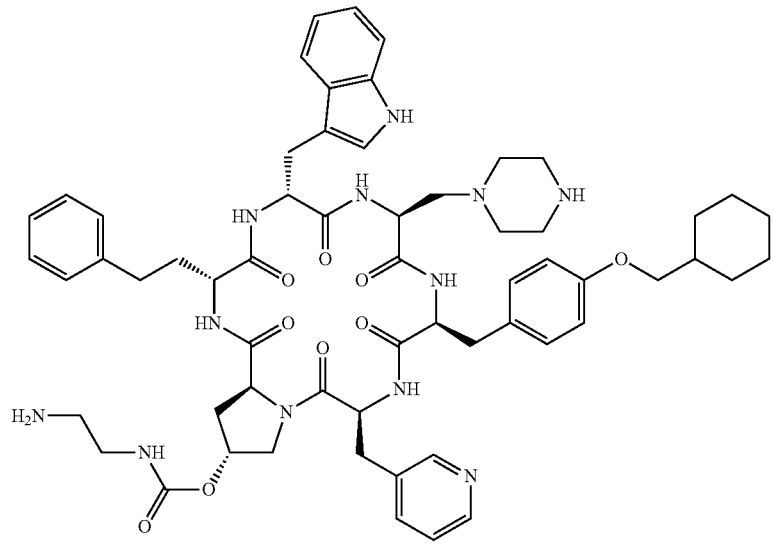
Example 71
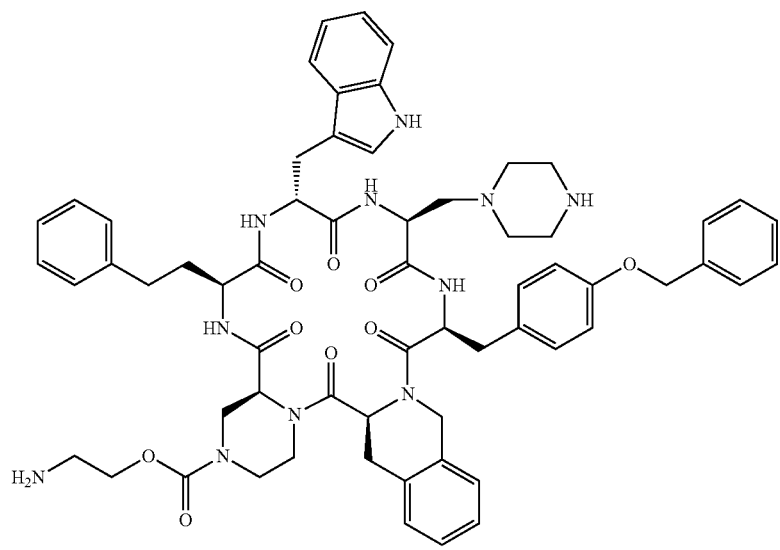
Example 72

TABLE 1-continued
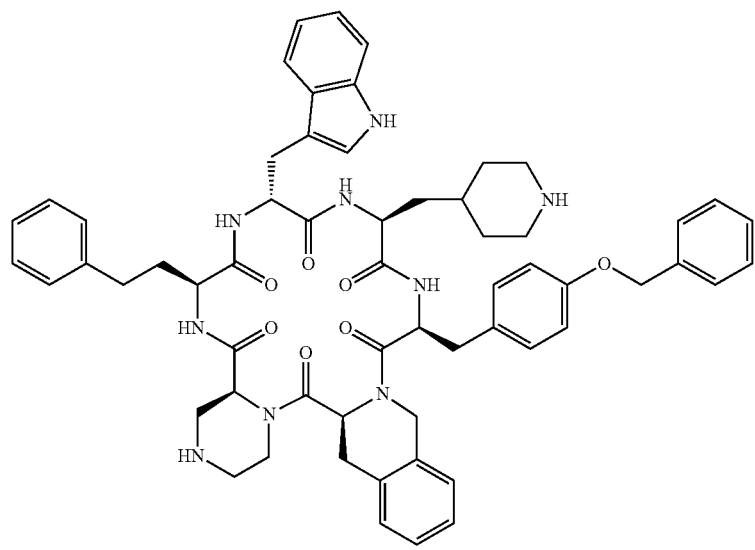
Example 73
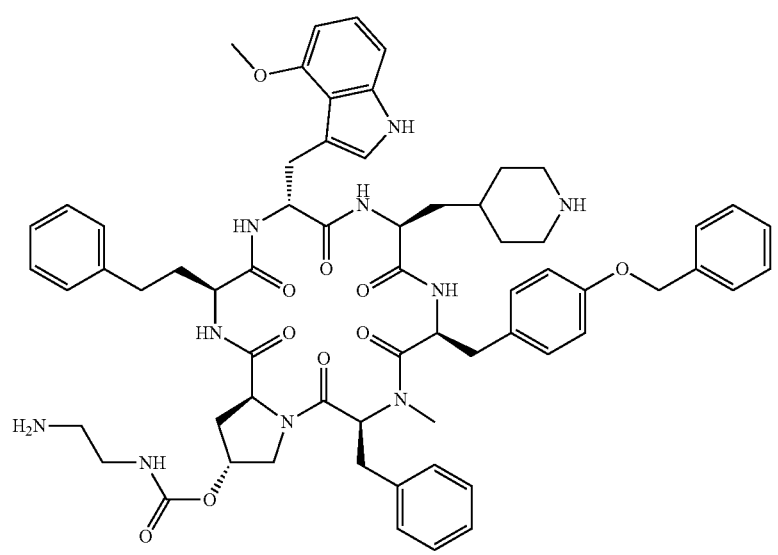
Example 74

TABLE 1-continued
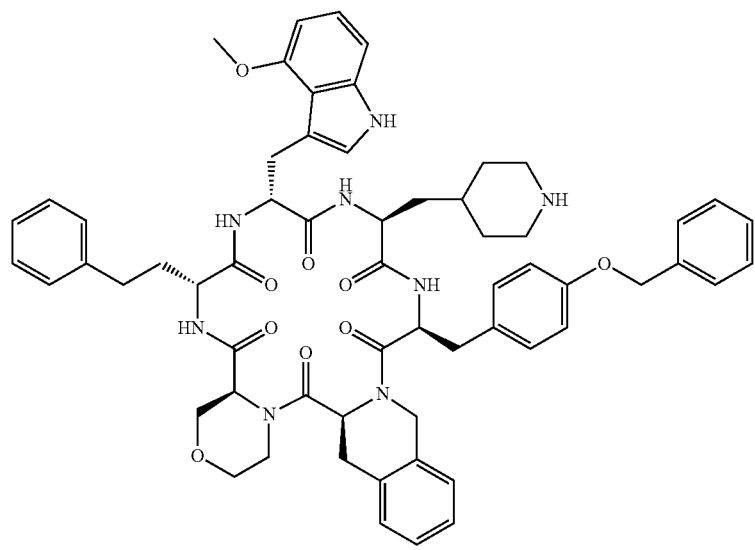
Example 75
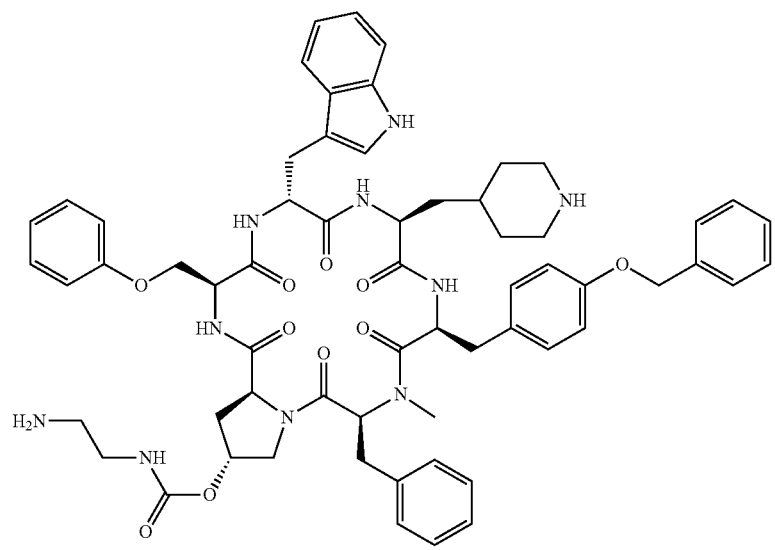
Example 76

TABLE 1-continued
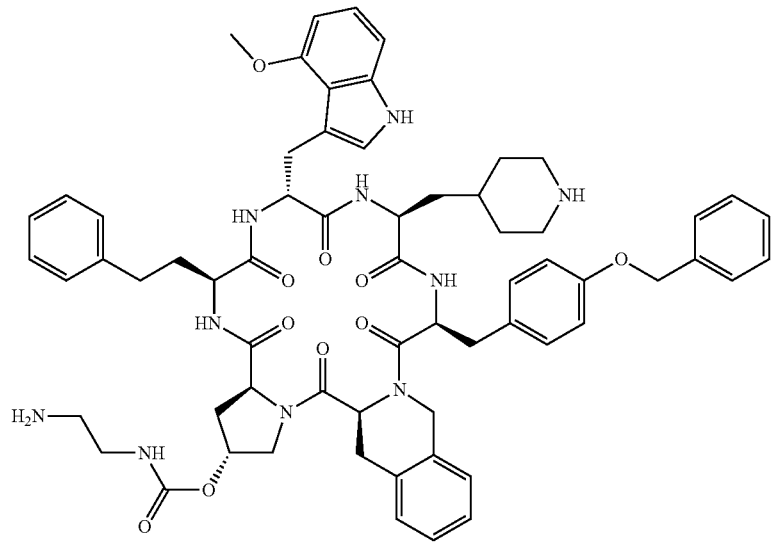
Example 77
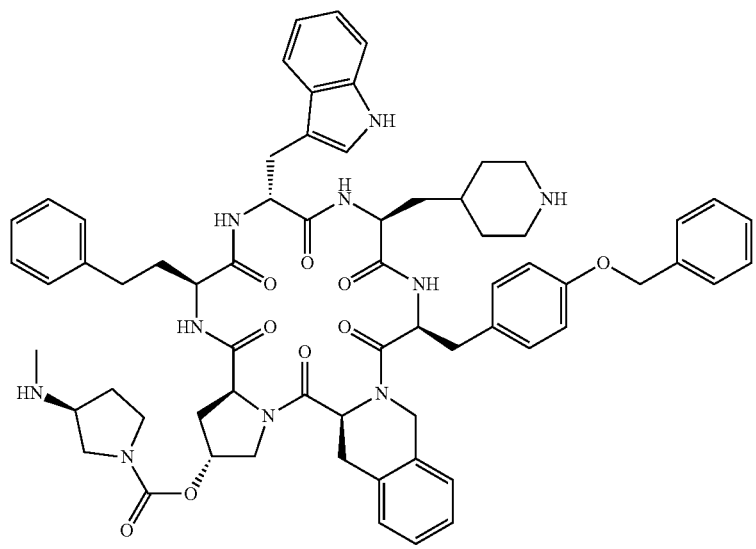
Example 78

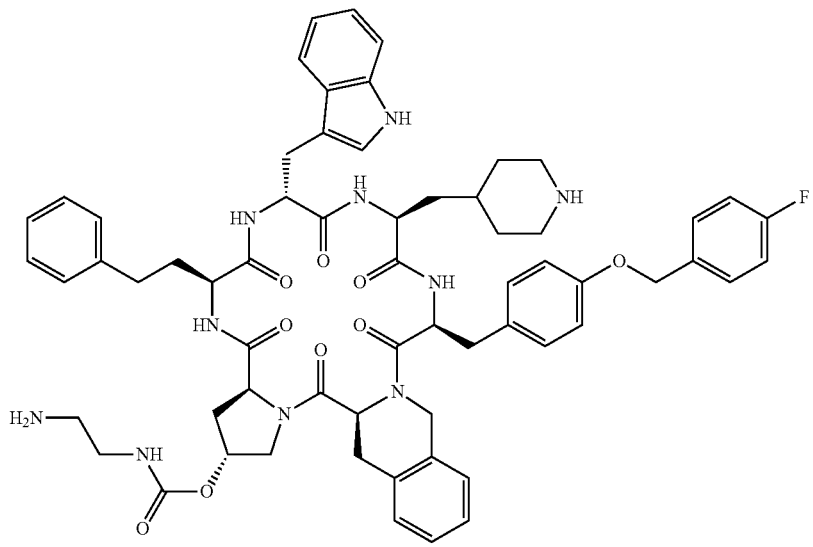

Example 79

General Procedures

Where no preparative routes are included, the relevant intermediate is commercially available. Commercial reagents were utilized without further purification. Room temperature (rt) refers to approximately 20-27° C. $^1$H NMR spectra were recorded at 600 MHz on a Bruker instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions.

Analytical Methods

LCMS analysis of compounds was performed under electrospray conditions.

LCMS Method A

Water Acquity UPLC-H Class, Column: Waters BEH C18 1.7 μm, 2.1×50 mm. Gradient [time (min)/solvent B (%)]: 0.0/10, 0.5/10, 2.5/90, 3.0/90. (Solvent A-0.025% HCOOH in water; Solvent B-0.025% HCOOH in MeCN); Injection volume 0.1 μL (may vary); UV detection 210 nm; Column temperature 30° C.; 0.3 mL/min.

Analytical Method B

MS ion determined using LCMS method below under electrospray conditions, HPLC retention time ($R_T$) determined using HPLC method below, purity >95% by HPLC unless indicated.

LCMS: Water Acquity UPLC-H Class, Column: Waters BEH C18 1.7 μm, 2.1×50 mm. Gradient [time (min)/solvent B (%)]:0.0/10, 0.5/10, 2.5/90, 3.0/90. (Solvent A-0.025% HCOOH in water; Solvent B-0.025% HCOOH in MeCN); Injection volume 0.1 μL (may vary); UV detection 210 nm; Column temperature 30° C.; 0.3 mL/min.

HPLC: Agilent Technologies 1200, Water SunFire C18, 3.5 μm, 4.6×150 mm, 30° C., 1 mL/min; mobile phase A: 0.025% TFA in water, mobile phase B: MeCN. a: Gradient, 5-75% (MeCN:H2O, 15 min), b: Gradient, 10-90% (MeCN:H2O, 15 min); c: 20-90% (MeCN:H2O, 15 min).

Analytical Method C

MS ion determined using LCMS method below under electrospray conditions, HPLC retention time ($R_T$) determined using HPLC method below, purity >95% by HPLC unless indicated.

LCMS: Agilent 1200 HPLC&6410B Triple Quad, Column: Xbridge C18 3.5 um 2.1*30 mm. Gradient [time (min)/solvent B (%)]:0.0/10, 0.9/80, 1.5/90, 8.5/5, 1.51/10. (Solvent A=1 mL of TFA in 1000 mL Water; Solvent B=1 mL of TFA in 1000 mL of MeCN); Injection volume 5 μL (may vary); UV detection 220 nm 254 nm 210 nm; Column temperature 25° C.; 1.0 mL/min.

HPLC: Agilent Technologies 1200, Column: Gemini-NX C18 5 um 110A 150*4.6 mm. Gradient [time (min)/solvent B (%)]:0.0/30, 20/60, 20.1/90, 23/90. (Solvent A=1 mL of TFA in 1000 mL Water; Solvent B=1 mL of TFA in 1000 mL of MeCN); Injection volume 5 μL (may vary); UV detection 220 nm 254 nm; Column temperature 25° C.; 1.0 mL/min Analytical Method D Instrument: Thermo Scientific Orbitrap Fusion; Column: Phenomenex Kinetex Biphenyl 100 Å, 2.6 μm, 2.1×50 mm; Gradient [time (min)/solvent B in A (%)]: 0.00/10, 0.30/10, 0.40/60, 1.10/90, 1.70/90, 1.75/10, 1.99/10, 2.00/10; Solvents: Solvent A=0.1% formic acid in water; Solvent B=0.1% formic acid in acetonitrile; Injection volume 5 μL; Column temperature 25° C.; Flow rate 0.8 mL/min.

Synthesis of Intermediates

Synthesis of Fmoc-D-Trp(4-Me)

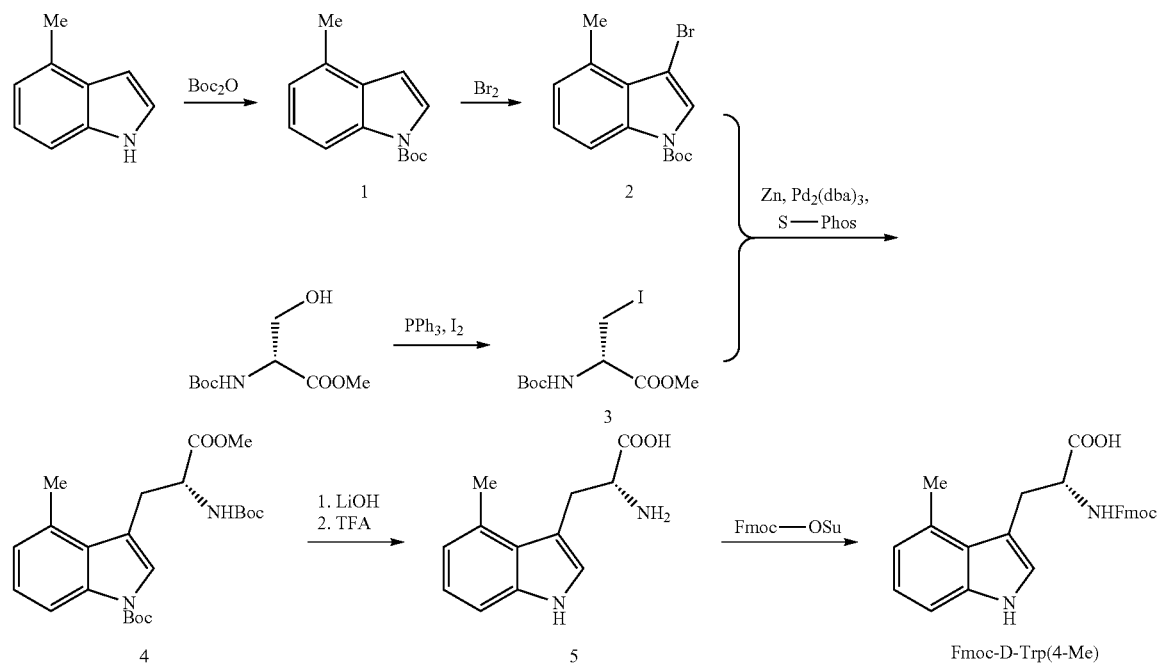

Procedure

N-Boc-4-methylindole (1)

4-Methylindole (5.0 g, 38 mmol) and dimethylaminopyridine (1.04 g, 8.54 mmol) were dissolved in acetonitrile (60 mL) and then a solution of di-tert-butyl dicarbonate (14.0 g, 64 mmol) in acetonitrile (10 mL) was added slowly. The reaction was stirred for 18 h at room temperature under a $N_2$ atmosphere then concentrated. The residue was diluted with EtOAc (100 mL), washed with 1 N HCl (100 mL×3), saturated $NaHCO_3$ (100 mL×3), water (100 mL×1) and brine (100 mL×1) and then dried (MgSO4). After filtration, the solvents were removed to afford compound 1 (8.3 g, quantitative yield), which was used for next step without further purification.

N-Boc-3-bromo-4-methylindole (2)

N-Bromosuccinimide (8.3 g, 47 mmol) was added all at once to a solution of N-Boc-indole (8.3 g, 38 mmol) in THF (100 mL) and the reaction was stirred for 18 h at room temperature. The reaction mixture was concentrated and the residue was diluted with EtOAc (100 mL), washed with saturated aqueous sodium metabisulfite (100 mL×3), saturated $NaHCO_3$ aq (100 mL×3) and brine. The organic phase was dried (MgSO4) and concentrated to afford compound 2 (8.7 g, yield 74%) as an yellow oil.

(S)-Methyl 2-(tert-butoxycarbonylamino)-3-iodopropanoate (3)

A mixture of triphenylphosphine (131 g, 0.50 mol) and imidazole (34 g, 0.50 mol) in DCM (600 mL) was cooled to 0° C. and iodide (127 g, 0.50 mol) was added in small portions over 0.5 h. The cooling bath was removed and the mixture was stirred for 0.5 h. After the mixture was re-cooled to 0° C., a solution of compound 2 (73 g, 0.33 mol) in DCM (300 mL) was added dropwise. Upon completion, the cooling bath was removed and the mixture was allowed to warm to room temperature and stirred for 1.5 h. The mixture was filtered and the filtrate was concentrated to remove most of the solvents. MTBE (400 mL) was added to the residue and the mixture was filtered to remove triphenylphosphine oxide. The filtrate was concentrated and the residue was purified by flash column chromatography to afford 3 (74.0 g, 68% yield) as a yellow solid.

(R)-tert-Butyl 3-(2-(tert-butoxycarbonylamino)-3-methoxy-3-oxopropyl)-4-methyl-1H-indole-1-carboxylate (4)

A solution of compound 3 (7.5 g, 26 mmol) and iodine (0.5 g) in DMF (30 mL) was added to a suspension of zinc (4.5 g, 77 mmol) in DMF (50 mL). The mixture was stirred at 30° C. under nitrogen for 30 min, then cooled to room temperature. Compound 2 (8.0 g, 25.8 mol), S-Phos (200 mg) and Pd(dba)$_2$ (400 mgl) was added. The reaction mixture was stirred at 50° C. under nitrogen overnight and then cooled to room temperature. Brine (500 mL) was added and the resulting mixture was extracted with EtOAc (300 mL×3). The organics were combined, washed with brine and concentrated. The residue was purified by flash column chromatography (petroleum ether/ethyl acetate=100:1 to 40:1) to afford 4 as a viscous oil (3.3 g, 30% yield).

D-Trp(4-Me)-OH (5)

To a solution of compound 4 (3.3 g, 7.6 mmol) in a mixture of water/methanol (30 mL, 2:1) was added lithium hydroxide hydrate (1.3 g, 30 mmol). The reaction mixture was stirred at room temperature for 3 h and then concentrated to remove most of methanol. The residue was extracted with EtOAc (30 mL×3), washed with brine (20 mL×2), dried and concentrated to afford acid.

The above acid was dissolved in DCM (20 mL), and TFA (5 mL) was added. The reaction mixture was stirred for 1 h and then concentrated to afford 5 as a TFA salt, which was used in the next step without further purification.

Fmoc-D-Trp(4-Me)

Compound 5 (7.6 mmol) was dissolved in a mixture of acetone (100 mL) and saturated NaHCO₃ aq (100 mL). Fmoc-OSu (2.5 g, 7.5 mmol) was added. The reaction mixture was stirred 18 h at room temperature. The reaction was diluted with H2O (100 mL), washed with hexane (100 mL×2). The aqueous phase was acidified with 1N HCl to pH 3 and extracted with EtOAc (100 mL×3). The combined EtOAc phases were washed with 1N HCl (100 mL×3) and brine (100 mL×1) and then dried over MgSO4. After filtration, the solvents was removed by concentration, the reside was purified by flash column chromatography (DCM/MeOH=100:1 to 20:1) to afford Fmoc-D-Trp(4-Me) (2.3 g, 68% yield form compound 4) as a white solid.

LCMS (Method A): m/z 441.7 [M+H]⁺ (ES+)

The following compounds were synthesized using the same method:

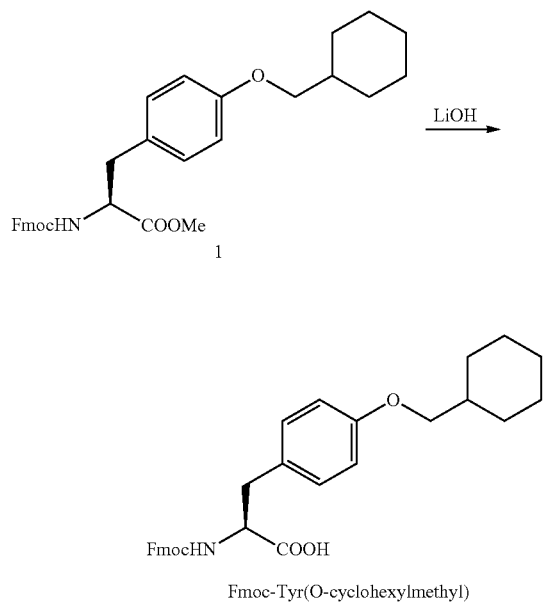

| Compound | Structure | Molecular Formula | ESI |
|---|---|---|---|
| Fmoc-D-Trp(5-Me) | (structure shown) | C27H24N2O4 | 441.7 [M + H]⁺ |
| Fmoc-D-Trp(4-OMe) | (structure shown) | C27H24N2O5 | 456.6 [M + H]⁺ |
| Fmoc-D-Trp(5-OMe) | (structure shown) | C27H24N2O5 | 456.8 [M + H]⁺ |

Synthesis of Fmoc-Tyr(O-cyclohexylmethyl)

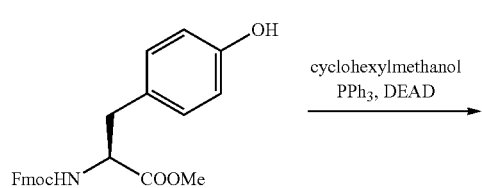

Procedure

Fmoc-L-Tyr(O-cyclohexylmethyl)-OMe (1)

A mixture of Fmoc-Tyr-OMe (1.5 g, 3.6 mmol), cyclohexylmethanol (500 mg, 4.4 mmol) and triphenylphosphine (1.13 g, 4.3 mol) in THF (100 mL) was cooled to 0° C. and DEAD (800 mg, 4.3 mol) was added. The mixture was allowed to warm to room temperature and stirred overnight. The reaction mixture was concentrated and the residue was purified by flash column chromatography to afford compound 1 (0.9 g, 48% yield).

Fmoc-L-Tyr(O-cyclohexylmethyl)

To a solution of compound 1 (0.9 g, 1.7 mmol) in water/methanol (30 mL, 10:1) was added lithium hydroxide hydrate (100 mg, 2.4 mmol). The reaction mixture was stirred at 0° C. for 3 h and then acidified with 1N HCl to pH 3. Then the mixture was extracted with EtOAc (30 mL×3), the extracts were washed with brine (20 mL×2), dried and concentrated. The reside was purified by flash column chromatography (DCM/MeOH=100:1 to 20:1) to afford Fmoc-L-Tyr(O-cyclohexylmethyl) (630 mg, 74% yield) as a white solid.

LCMS (Method A): m/z 500.9 [M+H]+(ES+), The following compound was synthesized using the same method:

| Compound | Structure | Molecular Formula | ESI |
|---|---|---|---|
| Fmoc-L-Tyr(O-4-chlorobenzyl) | (structure with Cl) | C31H26ClNO5 | 528.3 [M + H]+ |
| Fmoc-L-Tyr(O-4-Fluorobenzyl) | (structure with F) | C31H26FNO5 | 512.5 [M + H]+ |

Synthesis of Cyclohexapeptide Examples 1-79

Standard Fmoc solid phase peptide synthesis (SPPS) was used to synthesize the linear peptides which were then cleaved from the resin and cyclized to give the cyclohexapeptide. This linear synthesis can start at any position in the 6-mer sequence and then cyclisation can be carried out to give the final cyclohexapeptides, two methods are outlined below.

Method a

Peptide synthesis
1) To the vessel containing CTC-resin (0.4 mmol) and Fmoc-trans-4-HYP-OH (282.7 mg, 0.8 mmol, 2.0 eq.) under bubbled N$_2$ (g) was added DCM (10 mL).
2) DIEA (263.9 μL, 1.6 mmol, 4.0 eq.) was added dropwise and the reaction stirred for 2 h. 3) MeOH (0.8 mL) was added and the reaction stirred for 30 min.
4) The resin was drained and washed with DMF (×5).
5) Bis(p-nitrophenyl) carbonate (730.0 mg, 2.4 mmol, 6.0 eq.) and DIEA (0.8 mL, 4.8 mmol, 12.0 eq.) were added to the vessel, and the reaction continued for 4 h. After the reaction was complete, the resin was washed with DMF (×5).
6) N-Boc-ethylenediamine (770.0 mg, 4.8 mmol, 12.0 eq.) and DIEA (0.8 mL, 4.8 mmol, 12.0 eq.) were added respectively to the resin in DMF (10 mL). The reaction was mixed overnight at room temperature.
7) The resin was drained and washed with DMF (×5).
8) A solution of piperidine in DMF (piperidine: DMF, 1:4) was added and the reaction continued for 30 min.
9) The resin was drained and washed with DMF (×5).
10) Fmoc-amino acid solution (0.8 mmol, 2.0 eq.) was added to the resin and mixed for 30 seconds, followed by adding HATU (2.0 eq.) and DIEA (4.0 eq.). N$_2$ (g) was bubbled through the mixture for 1 h.
11) The resin was drained and washed with DMF (×5).
12) Repeat steps 8-11 for next amino acid coupling.

Peptide Cleavage, Cyclization and Purification
1) To the flask containing the side chain protected peptide at rt was added cleavage buffer (1% TFA in DCM, 10 mL) and the resulting mixture stirred for 0.5 h.
2) The reaction mixture was filtered and the filtrate diluted with anhydrous DCM to 1 mM. DIEA was added to adjust the pH to 8. To the solution was added TBTU (385.2 mg, 1.2 mmol, 3.0 eq.) and HOBT (162.9 mg, 1.2 mmol, 3.0 eq.) and the resulting solution reacted for 3-4 h.
3) Upon completion, the reaction mixture was washed with 1 N HCl (200 mL) and the organic phase dried under vacuum to obtain the crude peptide, which was further treated with TFA:H$_2$O:TIPS, 95:2.5:2.5 for 10 min-1 h.
4) The crude peptide was precipitated out by addition of methyl tert-butyl ether.
5) The crude peptide was purified by HPLC to give the final product. Prep-HPLC Conditions: Instrument: Gilson 281. Solvent: A-0.1% TFA in H2O, B-acetonitrile, Column: Luna C18 (200×25 mm; 10 μm) and Gemini C18 (150*30 mm; 5 μm) in series. Gradient [time (min)/solvent B (%)]:0.0/25, 60.0/55, 60.1/90, 70/90, 70.1/10 for example 17.

Method b

Peptide synthesis
1) The CTC-resin (1 eq.) was swelled in DMF (10×) for 2 h, washed with DMF (10×) three times, DCM (10×) three times and DMF (10×) three times.
2) Fmoc-protected amino acid (3 eq.) was dissolved in DMF, and then DIC (2.9 eq.), HOBt (2.9 eq.), and NMM (5.6 eq.) was added. The resulting mixture was shaken for 1 min and transferred to the resin.

3) The reaction was shaken for 1-2 h and monitored by Kaiser method. 4) After coupling, the resin was washed with DMF.
5) The Fmoc group was removed using a solution of piperidine in DMF (piperidine: DMF, 1:4), twice (2 min, 8 min).
6) The resins were carefully washed with DMF (10×) three times, DCM (10×) three times and DMF (10×) three times.

Note: Fmoc-phenylglycine was transformed into its activated HOBt-ester [fresh prepared from Fmoc-Phg (3.0 eq.) and HOBt (3.0 eq.) in the presence of DIC (3.0 eq., 0° C., 20 min) before solid phase synthesis.

Peptide Cleavage, Cyclization and Purification
1) The full-length, linear peptides were cleaved from the resin by swelling and shaking the peptide-resin for 4 h in a 1:1 (v:v) TFE/DCM (10 vol/g of dried resin).
2) The cleaved solution was filtered and the drained resin was washed with additional DCM (5 vol/g of initial dried peptide-resin) to fully extract the cleaved peptide from the resin. Solvents in the combined filtrates were evaporated and the residue dried.
3) The crude peptides were dissolved in a mixture of DMF/DCM (30 vol/g, 1/5), cooled to 0° C. and DIC (5 eq.) and HOBt (5 eq.) were added. Upon completion, the reaction was washed with aq. sat. NaCO$_3$ (2×) and brine (1×). The organic layer was dried, filtered, and concentrated to afford crude cyclopeptides.
4) Crude cyclopeptides were deprotected by stirring in a mixture of TFA/DCM (50 vol/g, 1/1) for 1 h. The products were precipitated from cold diethyl ether and filtered to afford crude peptides, which were purified by prep-HPLC to afford cyclic hexapeptides. Prep-HPLC Conditions: Instrument: Water Auto-P 2545/2489/515. Solvent: A-0.1% TFA in Water, B-MeCN, Column: SunFire Prep C18 OBD, 5 μm, 30×100 mm. Gradient [time (min)/solvent B (%)]: 0.0/30, 1.0/30, 9.0/45, 9.5/95, 13.0/95. UV detection 210 nm & MS detection; Column temperature 25° C.; 30 mL/min.

TABLE 2

HRMS and LCMS properties and the methods used to prepare and purify peptides represented by Examples 1-79

| Example | Synthetic Method | HRMS (Method D) | Analytical Method | LCMS/HPLC |
|---|---|---|---|---|
| 1 | b | (HESI/FT) m/z: [M + 2H]$^{2+}$ Calcd for C$_{60}$H$_{70}$O$_9$N$_{10}$ 537.2658; Found 537.2672 | B | m/z 1073.5 [M + H]$^+$, R$_T$ = 6.35 min (b) |
| 2 | b | (HESI/FT) m/z: [M + 2H]$^{2+}$ Calcd for C$_{61}$H$_{72}$O$_9$N$_{10}$ 544.2736; Found 544.2750 | B | m/z 1087.9 [M + H]$^+$, R$_T$ = 8.32 min (b) |
| 3 | a | (HESI/FT) m/z: [M + 2H]$^{3+}$ Calcd for C$_{61}$H$_{74}$O$_9$N$_{11}$ 368.18848; Found 368.1884; | C | m/z 1103.3 [M + H]$^+$, R$_T$ = 11.07 min |
| 3 | a | m/z: [M + 2H]$^{2+}$ Calcd for C$_{61}$H$_{73}$O$_9$N$_{11}$ 551.77909; Found 551.7786; m/z: [M + H] Calcd for C$_6$H$_{72}$O$_9$N$_{11}$ 1102.5509; Found 1102.5507 | | |
| 4 | b | (HESI/FT) m/z: [M + 2H]$^{2+}$ Calcd for C$_{61}$H$_{72}$O$_9$N$_{10}$ 544.2736; Found 544.2750 | B | m/z 1087.9 [M + H]$^+$, R$_T$ = 8.10 min (b) |
| 5 | b | (HESI/FT) m/z: [M + 2H]$^{2+}$ Calcd for C$_{61}$H$_{72}$O$_{10}$N$_{10}$ 552.2711; Found 552.2724 | B | m/z 1103.78 [M + H]$^+$, R$_T$ = 7.85 min (b) |
| 6 | b | (HESI/FT) m/z: [M + 2H]$^{2+}$ Calcd for C$_{60}$H$_{69}$O$_9$N$_{10}$Cl 554.2463; Found 554.2477 | B | m/z 1108.82 [M + H]$^+$, R$_T$ = 7.56 min (b) |
| 7 | b | (HESI/FT) m/z: [M + 2H]$^{2+}$ Calcd for C$_{60}$H$_{69}$O$_9$N$_{10}$Cl 554.2463; Found 554.2477 | B | m/z 1108.82 [M + 2H]$^+$, R$_T$ = 7.62 min (b) |
| 8 | b | (HESI/FT) m/z: [M + 2H]$^{2+}$ Calcd for C$_{60}$H$_{69}$O$_9$N$_{10}$Cl 554.2463; Found 554.2477 | B | m/z 554.9 [M + 2H]$^{2+}$, R$_T$ = 7.76 min (b) |
| 9 | b | (HESI/FT) m/z: [M + 2H]$^{2+}$ Calcd for C$_{61}$H$_{72}$O$_{10}$N$_{10}$ 552.2711; Found 552.2724 | B | m/z 1104.14 [M + H]$^+$, R$_T$ = 8.87 min (a) |
| 10 | b | (HESI/FT) m/z: [M + 2H]$^{2+}$ Calcd for C$_{60}$H$_{69}$O$_9$N$_{10}$Br 576.2211; Found 576.2225 | B | m/z 1152.74 [M + H]$^+$, R$_T$ = 9.49 min (a) |
| 11 | b | (HESI/FT) m/z: [M + 2H]$^{2+}$ Calcd for C$_{59}$H$_{69}$O$_9$N$_{11}$ 537.7634; Found 537.7634 | B | m/z 1096.8 [M + Na]$^+$, R$_T$ = 6.62 min (b) |
| 12 | b | (HESI/FT) m/z: [M + 2H]$^{2+}$ Calcd for C$_{61}$H$_{72}$O$_{10}$N$_{10}$ 552.2711; Found 552.2711 | B | m/z 1103.5 [M + H]$^+$, R$_T$ = 7.54 min (b) |
| 13 | b | (HESI/FT) m/z: [M + 2H]$^{2+}$ Calcd for C$_{61}$H$_{72}$O$_9$N$_{10}$ 544.2736; Found 544.2750 | B | m/z 1087.8 [M + H]$^+$, R$_T$ = 8.11 min (b) |
| 14 | a | (HESI/FT) m/z: [M + H]$^{2+}$ Calcd for C$_{60}$H$_{73}$O$_9$N$_{12}$ 368.52023; Found 368.5201; m/z: [M + H]$^{2+}$ Calcd for C$_{60}$H$_{72}$O$_9$N$_{12}$ 552.27671; Found 552.2763; m/z: [M + H]$^+$ Calcd for C$_{60}$H$_{71}$O$_9$N$_{12}$ 1103.54615; Found 1103.5452 | C | m/z 552.7 [M + 2H]$^{2+}$, R$_T$ = 7.08 min |
| 15 | b | (HESI/FT) m/z: [M + 2H]$^{2+}$ Calcd for C$_6$H$_{73}$O$_9$N$_{11}$ 551.7791; Found 551.7791 | C | m/z 1102.2 [M + H]$^+$, R$_T$ = 9.83 min |
| 16 | b | (HESI/FT) m/z: [M + 2H]$^{2+}$ Calcd for C$_{60}$H$_{72}$O$_9$N$_{12}$ 552.2767; Found 552.2781 | C | m/z 1103.4 [M + H]$^+$, R$_T$ = 9.74 min |
| 17 | b | (HESI/FT) m/z: [M + 2H]$^{2+}$ Calcd for C$_{63}$H$_{74}$O$_9$N$_{10}$ 557.28146; Found 557.2812; m/z: [M + H]$^+$ Calcd for C$_{63}$H$_{73}$O$_9$N$_{10}$ 1113.55565; Found 1113.5544 | C | m/z 1113.5 [M + H]$^+$, R$_T$ = 10.89 min |
| 18 | a | (HESI/FT) m/z: [M + 2H]$^{2+}$ Calcd for C$_8$H$_{74}$O$_9$N$_{18}$ 557.2815; Found 557.2828 | C | m/z 557.3 + [M + 2H]$^{2+}$, R$_T$ = 10.67 min |
| 19 | a | (HESI/FT) m/z: [M + 2H]$^{2+}$ Calcd for C$_{83}$H$_{74}$O$_9$N$_{10}$ 557.2815; Found 557.2828 | C | m/z 557.3 [M + 2H]$^{2+}$, R$_T$ = 10.37 min |

TABLE 2-continued

HRMS and LCMS properties and the methods used to prepare and purify peptides represented by Examples 1-79

| Example | Synthetic Method | HRMS (Method D) | Analytical Method | LCMS/HPLC |
|---|---|---|---|---|
| 20 | a | (HESI/FT) m/z: [M + 2H]$^{2+}$ Calcd for C$_{83}$H$_{70}$O$_8$N$_{18}$ 547.2684; Found 547.2684 | C | m/z 1093.4 [M + H]$^+$, R$_T$ = 13.42 min |
| 21 | a | (HESI/FT) m/z: [M + 2H]$^{2+}$ Calcd for C$_{63}$H$_{72}$O$_9$N$_{10}$Na 1135.54; Found 11135.5378; m/z: [M + H]$^+$ Calcd for C$_{63}$H$_{73}$O$_9$N$_{10}$ 1113.5557; Found 1113.5556 | C | m/z 1113.3 [M + H]$^+$, R$_T$ = 9.60 min |
| 22 | a | (HESI/FT) m/z: [M + 2H]$^+$ Calcd for C$_{83}$H$_{70}$O$_8$N$_{10}$ 547.2684; Found 547.2684 | C | m/z 1093.4 [M + H]$^+$, R$_T$ = 10.37 min |
| 23 | a | (HESI/FT) m/z: [M + 2H]$^+$ Calcd for C$_{83}$H$_{70}$O$_8$N$_{10}$ 547.2684; Found 547.2684 | C | m/z 1093.4 [M + H]$^+$, R$_T$ = 10.27 min |
| 24 | a | (HESI/FT) m/z: [M + H]$^+$ Calcd for C$_{83}$H$_{70}$O$_8$N$_{10}$ 547.2684; Found 547.2697 | C | m/z 1093.3 [M + H]$^+$, R$_T$ = 10.65 min |
| 25 | a | (HESI/FT) m/z: [M + H]$^+$ Calcd for C$_{62}$H$_{72}$O$_9$N$_{11}$1114.5509; Found 1136.5330 m/z: [M + H]$^+$ Calcd for C$_{62}$H$_{72}$O$_9$N$_{11}$ 1114.5509; Found 1114.5508 | C | m/z 1114.4 [M + H]$^+$, R$_T$ = 9.56 min |
| 26 | b | (HESI/FT) m/z: [M + H]$^{2+}$ Calcd for C$_{62}$H$_{73}$O$_9$N$_{11}$ 557.77909; Found 557.7789; m/z: [M + H]$^+$ Calcd for C$_{62}$H$_{72}$O$_9$N$_{11}$ 1114.5509; Found 1114.5502 | C | m/z 1114.3 [M + H]$^+$, R$_T$ = 9.42 min |
| 27 | b | (HESI/FT) m/z: [M + 2H]$^{2+}$ Calcd for C$_{59}$H$_{75}$O$_9$N$_{11}$ 540.7869; Found 540.7883 | B | m/z 1102.8 [M + Na]$^+$, R$_T$ = 8.45 min (b) |
| 28 | b | (HESI/FT) m/z: [M + 2H]$^{2+}$ Calcd for C$_{62}$H$_{74}$O$_9$N$_{10}$ 551.2815; Found 551.2828 | B | m/z 1102.8 [M + H]$^+$, R$_T$ = 8.25 min (b) |
| 29 | b | (HESI/FT) m/z: [M + 2H]$^{2+}$ Calcd for C$_{62}$H$_{74}$O$_9$N$_{10}$ 551.2815; Found 551.2815 | B | m/z 1102.0 [M + H]$^+$, R$_T$ = 8.55 min (b) |
| 30 | b | (HESI/FT) m/z: [M + 2H]$^{2+}$ Calcd for C$_{61}$H$_{72}$O$_9$N$_{11}$Cl 568.7596; Found 568.7609 | B | m/z 1136.8 [M + H]$^+$, R$_T$ = 8.80 min (b) |
| 31 | b | (HESI/FT) m/z: [M + H]$^{2+}$ Calcd for C$_{59}$H$_{66}$O$_8$N$_9$ 1028.50289; Found 1028.5022; m/z: [M + H]$^{2+}$ Calcd for C$_{59}$H$_{67}$O$_8$N$_9$ 514.75508; Found 514.7549 | B | m/z 1028.9 [M + H]$^+$, R$_T$ = 10.72 min (b) |
| 32 | b | (HESI/FT) m/z:[M + H]$^+$ Calcd for C$_{61}$H$_{69}$O$_8$N$_8$ 1041.5233; Found 1041.5233 | B | m/z 1041.8 [M + H]$^+$, R$_T$ = 11.26 min (b) |
| 33 | a | (HESI/FT) m/z: [M + 2H]$^{2+}$ Calcd for C881-17209N12 552.2767; Found 552.2767 | C | m/z 1103.3 [M + H]$^+$, R$_T$ = 9.17 min |
| 34 | a | (HESI/FT) m/z: [M + 2H]$^{2+}$ Calcd for C881-17209N12 552.2767; Found 552.2767 | C | m/z 1103.3 [M + H]$^+$, R$_T$ = 9.91 min |
| 35 | a | (HESI/FT) m/z: [M + 2H]$^{2+}$ Calcd for C$_{62}$H$_{73}$O$_9$N$_{11}$ 557.7791; Found 557.7791 | C | m/z 1114.4 [M + H]$^+$, R$_T$ = 10.93 min |
| 36 | a | (HESI/FT) m/z: [M + 2H]$^{2+}$ Calcd for C821-17309N11 557.7791; Found 557.7804 | C | m/z 1114.4 [M + H]$^+$, R$_T$ = 10.00 min |
| 37 | b | (HESI/FT) m/z: [M + 2H]$^{2+}$ Calcd for C$_{57}$H$_{71}$O$_9$N$_{11}$ 526.764; Found 526.2757 | B | m/z 1052.1 [M + H]$^+$, R$_T$ = 7.44 min (b) |
| 38 | b | (HESI/FT) m/z:[M + 2H]$^{2+}$ Calcd for C$_{62}$H$_{74}$O$_9$N$_{10}$ 551.2815; Found 551.2815 | B | m/z 1101.9 [M + H]$^+$, R$_T$ = 7.04 min (c) |
| 39 | b | (HESI/FT) m/z: [M + 2H]$^{2+}$ Calcd for C$_{62}$H$_{75}$O$_{10}$N$_{11}$ 566.7844; Found 566.7857 | B | m/z 1155.0 [M + Na]$^+$, R$_T$ = 6.23 min (c) |
| 40 | b | (HESI/FT) m/z: [M + 2H]$^{2+}$ Calcd for C$_{61}$H$_{72}$O$_9$N$_{11}$Cl 568.7596; Found 568.7609 | B | m/z 1159.0 [M + Na]$^+$, R$_T$ = 7.45 min (b) |
| 41 | b | (HESI/FT) m/z: [M + 2H]$^{2+}$ Calcd for C$_{62}$H$_{73}$O$_9$N$_{10}$Cl 568.2620; Found 568.2620 | B | m/z 1136.0 [M + H]$^+$, R$_T$ = 8.09 min (b) |
| 42 | b | (HESI/FT) m/z: [M + 2H]$^{2+}$ Calcd for C$_{62}$H$_{73}$O$_9$N$_{10}$Cl 568.2612; Found 568.2634 | B | m/z 1157.9 [M + Na]$^+$, R$_T$ = 8.17 min (b) |
| 43 | b | (HESI/FT) m/z: [M + 2H]$^{2+}$ Calcd for C$_{63}$H$_{76}$O$_{10}$N$_{10}$ 566.2868; Found 566.2881 | B | m/z 1131.9 [M + H]$^+$, R$_T$ = 6.92 min (c) |
| 44 | b | (HESI/FT) m/z: [M + 2H]$^{2+}$ Calcd for C$_{63}$H$_{80}$O$_9$N$_{10}$ 560.30494; Found 560.3056 | B | m/z 1120.0 [M + H]$^+$, R$_T$ = 7.57 min (c) |
| 45 | b | (HESI/FT) m/z: [M + H]$^+$ Calcd for C$_{60}$H$_{67}$O$_8$N$_8$ 1027.5076; Found 1027.5078 m/z: [3M + H]$^{2+}$ Found 1541 | B | m/z 1028.2 [M + H]$^+$, |
| 46 | b | (HESI/FT) m/z: [M + H]$^+$ Calcd for C$_{61}$H$_{69}$O$_9$N$_8$ 1057.5182; Found 1057.5239 | B | m/z 1058.0 [M + H]$^+$, R$_T$ = 10.38 min (b) |
| 47 | b | (HESI/FT) m/z: [M + 2H]$^{2+}$ Calcd for C$_{61}$H$_{71}$O$_9$N$_{11}$Cl$_2$ 585.7401; Found 585.7408 | B | m/z 1171.9 [M + H]$^+$, R$_T$ = 8.12 min (b) |
| 48 | b | (HESI/FT) m/z: [M + 2H]$^{2+}$ Calcd for C$_{61}$H$_{72}$O$_9$N$_{11}$Cl 568.7596; Found 568.7603 | B | m/z 1158.9 [M + H]$^+$, R$_T$ = 8.20 min (b) |
| 49 | b | (HESI/FT) m/z: [M + 2H]$^{2+}$Calcd for C$_{60}$H$_{77}$O$_9$N$_{11}$ 547.7947; Found 547.7954 | B | m/z 1095.1 [M + H]$^+$, R$_T$ = 7.25 min (b) |
| 50 | b | (HESI/FT) m/z: [M + H]$^+$ Calcd for C$_{59}$H$_{74}$O$_9$N$_{11}$ 1080.5666; Found 1080.5665 | B | m/z 1103.0 [M + H]$^+$, R$_T$ = 6.87 min (b) |
| 51 | b | (HESI/FT) m/z: [M + H]$^+$ Calcd for C$_{61}$H$_{72}$O$_9$N$_{11}$Cl 568.7596; Found 568.7603 | B | m/z 1136.9 [M + H]$^+$, R$_T$ = 8.12 min (b) |

TABLE 2-continued

HRMS and LCMS properties and the methods used to prepare and purify peptides represented by Examples 1-79

| Example | Synthetic Method | HRMS (Method D) | Analytical Method | LCMS/HPLC |
|---|---|---|---|---|
| 52 | b | (HESI/FT) m/z: [M + 2H]$^{2+}$ Calcd for C$_{60}$H$_{78}$O$_9$N$_{12}$ 555.3002; Found 555.3022 | B | m/z 1110.1 [M + H]$^+$, R$_T$ = 7.27 min (b) |
| 53 | b | (HESI/FT) m/z: [M + 2H]$^{2+}$ Calcd for C611-17909N11 554.8026; Found 554.8026 | B | m/z 1131.1 [M + H]$^+$, R$_T$ = 7.33 min (b) |
| 54 | b | (HESI/FT) m/z: [M + 2H]$^+$ Calcd for C$_{61}$H$_{79}$O$_9$N$_{11}$ 554.8026; Found 554.8039 | B | m/z 1131.1 [M + H]$^+$, R$_T$ = 8.03 min (b) |
| 55 | b | (HESI/FT) m/z: [M + 2H]$^{2+}$ Calcd for C$_{63}$H$_{76}$O$_{10}$N$_{10}$ 566.2868; Found 566.2881 | B | m/z 1132.0 [M + H]$^+$, R$_T$ = 7.71 min (b) |
| 56 | b | (HESI/FT) m/z: [M + 2H]$^{2}$ $^+$Calcd for C$_{64}$H$_{79}$O$_{10}$N$_{10}$ 572.2868.; Found 572.2867 | B | m/z 1144.0 [M + H]$^+$, R$_T$ = 7.49 min (b) |
| 57 | b | (HESI/FT) m/z: [M + 2H]$^{2+}$ Calcd for C$_{62}$H$_{76}$O$_9$N$_{11}$ 558.7869; Found 558.7883 | B | m/z 1139.0 [M + Na]$^+$, R$_T$ = 8.02 min (b) |
| 58 | b | (HESI/FT) m/z: [M + 2H]$^+$ Calcd for C$_{60}$H$_{71}$O$_9$N$_{12}$Cl 569.2572; Found 569.2586 | B | m/z 1137.9 [M + H]$^+$, R$_T$ = 6.35 min (b) |
| 59 | b | (HESI/FT) m/z: [M + H]$^+$ Calcd for C$_{60}$H$_{71}$O$_9$N$_{12}$Cl 569.2572; Found 569.2570 | B | m/z 1137.9 [M + H]$^+$, R$_T$ = 7.43 min (b) |
| 60 | b | (HESI/FT) m/z: [M + H]$^+$ Calcd for C$_{62}$H$_{75}$O$_9$N$_{11}$ 558.7869; Found 558.7869 | B | m/z 1116.9 [M + H]$^+$, R$_T$ = 7.03 min (b) |
| 61 | b | (HESI/FT) m/z: [M + H]$^+$ Calcd for C$_{59}$H$_{66}$O$_8$N$_9$ 1028.5029; Found 1028.5056 | B | m/z 1029.0 +M+30H+, R$_T$ = 10.48 min (b) |
| 62 | b | (HESI/FT) m/z: [M + H]$^+$ Calcd for C$_{60}$H$_{67}$O$_8$N$_8$ 1027.5076; Found 1027.5103 | B | m/z 1028.0 [M + H]$^+$, R$_T$ = 10.32 min (b) |
| 63 | b | (HESI/FT) m/z: [M + H]$^+$ Calcd for C$_{60}$H$_{68}$O$_9$N$_9$ 1058.5135; Found 1058.5175 | B | m/z 1080.9 [M + Na]$^+$, R$_T$ = 8.52 min (c) |
| 64 | b | (HESI/FT) m/z: [M + 2H]$^{2+}$ Calcd for C$_{60}$H$_{71}$O$_{10}$N$_{11}$ 552.7687; Found 552.7687 | B | m/z 1104.9 [M + H]$^+$, R$_T$ = 7.35 min (b) |
| 65 | b | (HESI/FT) m/z: [M + 2H]$^{2+}$Calcd for C$_{59}$H$_{68}$O$_7$N$_{10}$ 514.26307; Found 514.2651 | B | m/z 514.8 [M + H]$^+$, R$_T$ = 8.31 min (b) |
| 66 | b | (HESI/FT) m/z: [M + 2H]$^{2+}$ Calcd for C$_{65}$H$_{78}$O$_{11}$N$_{10}$ 587.2920; Found 587.2940 | B | m/z 1174.7 [M + H]$^+$, R$_T$ = 7.58 min (b) |
| 67 | b | (HESI/FT) m/z: [M + 2H]$^{2+}$ Calcd for C$_{60}$H$_{71}$O$_9$N$_{11}$ 544.7713; Found 544.7713 | B | m/z 1188.9 [M + H]$^+$, R$_T$ = 6.69 min (b) |
| 68 | b | (HESI/FT) m/z: [M + H]$^{2+}$ Calcd for C$_{60}$H$_{68}$O$_9$N$_9$ 1058.5135; Found 1058.5135 | B | m/z 1058.9 [[M + H]$^+$, R$_T$ = 10.71min (b) |
| 69 | b | ND | B | m/z 1067.9 [M + 2H]$^{2+}$, R$_T$ = 8.61 min (b) |
| 70 | b | (HESI/FT) m/z: [M + 2H]$^{2+}$ Calcd for C$_{57}$H$_{69}$O$_9$N$_{11}$F$_2$ 544.7618; Found 544.7618 | B | m/z 545.5 [M + 2H]$^{2+}$, R$_T$ = 7.16 min (b) |
| 71 | b | (HESI/FT) m/z: [M + 2H]$^{2+}$ Calcd for C$_{60}$H$_{78}$O$_9$N$_{12}$ 555.3002; Found 555.3002 | B | m/z 1110.0 [M + 2H]$^{2+}$, R$_T$ = 7.03 min (b) |
| 72 | b | (HESI/FT) m/z: [M + 2H]$^{2+}$ Calcd for C$_{62}$H$_{73}$O$_9$N$_{11}$ 557.7791; Found 557.7804 | B | m/z 559.1 [M + 2H]$^{2+}$, R$_T$ = 7.92 min (b) |
| 73 | b | (HESI/FT) m/z: [M + 2H]$^{2+}$ Calcd for C$_{60}$H$_{69}$O$_7$N$_9$ 513.7655; Found 513.7675 | B | m/z 514.3 [M + 2H]$^{2+}$, R$_T$ = 8.48 min (b) |
| 74 | b | (HESI/FT) m/z: [M + 2H]$^{2+}$ Calcd for C$_{64}$H$_{78}$O$_{10}$N$_{10}$ 573.2946; Found 573.2966 | B | m/z 1168.0 [M + Na]$^+$, R$_T$ = 8.02 min (b) |
| 75 | b | (HESI/FT) m/z: [M + H]$^+$ Calcd for C$_{61}$H$_{69}$O$_9$N$_8$ 1057.5182; Found 1057.5182 | B | m/z 1057. [M + H]$^+$, R$_T$ =10.79 min (b) |
| 76 | b | (HESI/FT) m/z: [M + 2H]$^{2+}$ Calcd for C$_{62}$H$_{74}$O$_{10}$N$_{10}$ 559.2789; Found 559.2809 | B | m/z 1118.9 [M + H]$^+$, R$_T$ = 8.40 min (b) |
| 77 | b | ND | B | m/z 1144.0 [M + H]$^+$, R$_T$ = 7.44 min (b) |
| 78 | b | (HESI/FT) m/z: [M + 2H]$^{2+}$ Calcd for C661-17809N10 577.2971; Found 577.2985 | B | m/z 577.7 [M + 2H]$^{2+}$, R$_T$ = 7.75 min (b) |
| 79 | a | (HESI/FT) m/z: [M + 2H]$^{2+}$ Calcd for C$_{63}$H$_{73}$O$_9$N$_{10}$F 566.2695; Found 566.2785 | C | m/z 1132.3 [M + H]$^+$, R$_T$ = 8.75 min |

ND—Not determined

TABLE 3

$^1$H NMR and $^{13}$C NMR analysis for selected Examples

| Example | Structure | $^1$H NMR | $^{13}$C NMR |
|---|---|---|---|
| 3 | FIG. 1 | $^1$H NMR (600 MHz, Pyr): δ = 1.11-1.24 (m, 1 H, 54<AX>), 1.24-1.37 (m, 2 H, 55<AX>, 55<AX>), 1.37-1.48 (m, 2 H, 53<">, 55<EQ>), 1.67 (d, J = 13.2 Hz, 1 H, 55<EQ>), 1.71-1.82 (m, 2 H, 25<">, 53<'>), 2.40-2.49 (m, 1 H, 18<">), 2.48-2.57 (m, 1 H, 18<'>), 2.66 (dt, J = 13.4, 4.8 Hz, 1 H, 25<'>), 2.78-2.90 (m, 2 H, 19), 2.91-3.04 (m, 2 H, 56<AX>, | $^{13}$C NMR (151 MHz, Pyr): δ = 28.3 (55), 28.5 (63), 29.5 (55), 30.7 (54), 32.4 (19), 34.5 (18), 35.3 (33), 37.6 (43), 37.8 (25), 37.9 (53), 39.5 (29), 40.1 |

TABLE 3-continued

¹H NMR and ¹³C NMR analysis for selected Examples

Figure 2:
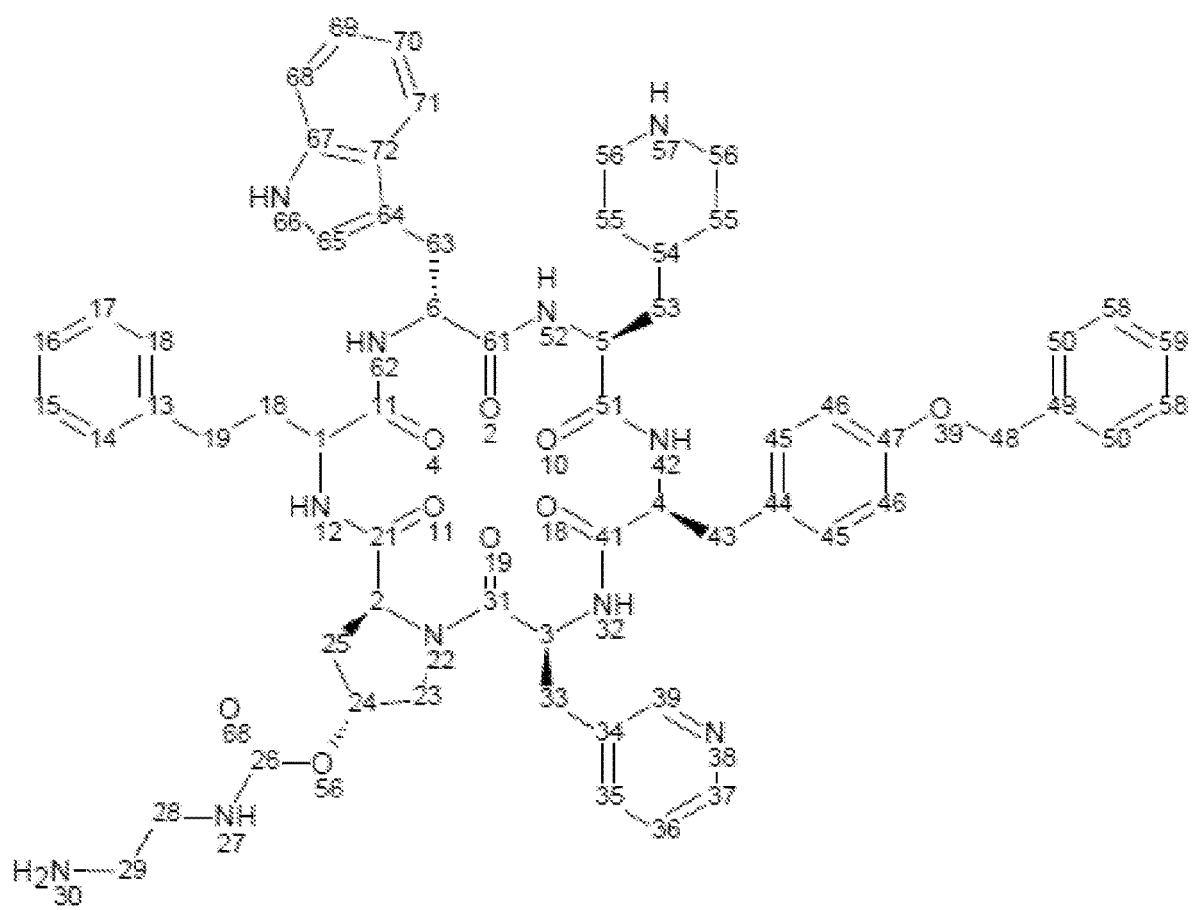
Figure 3:
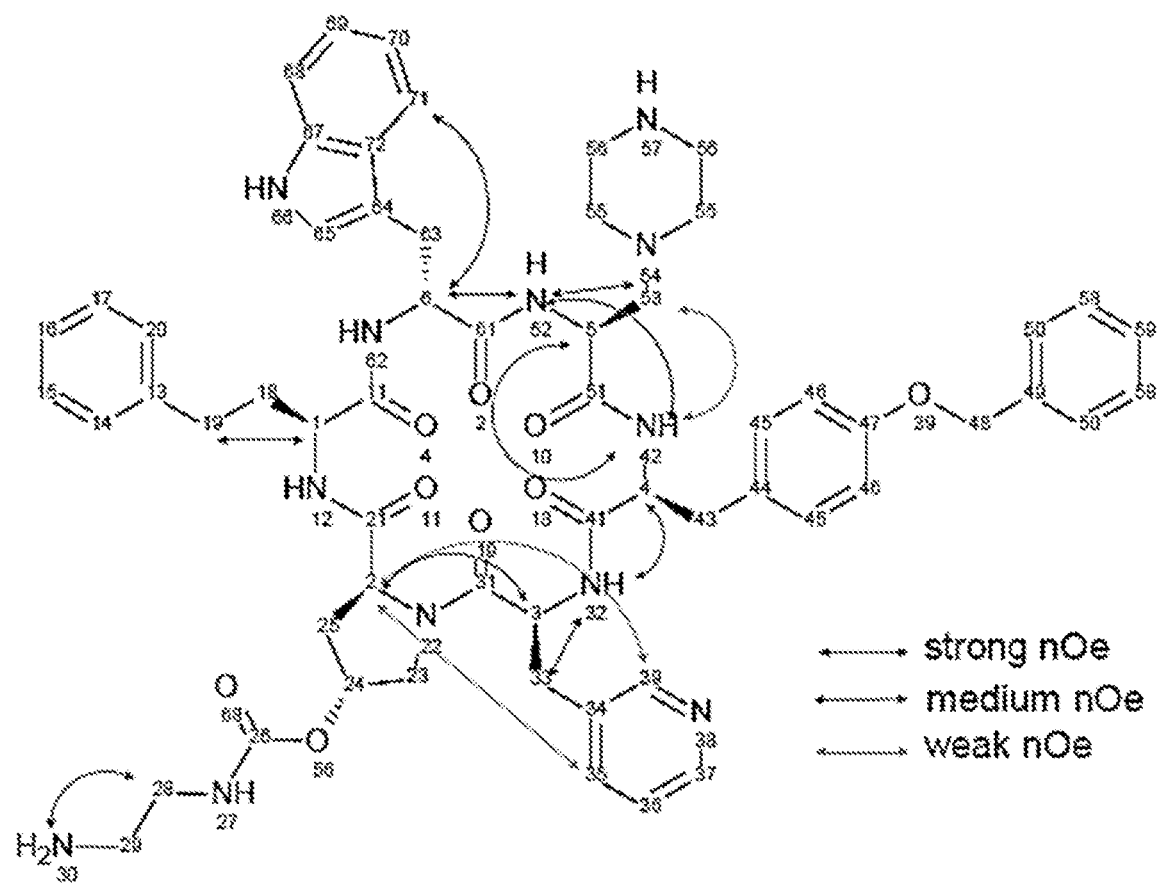

| Example | Structure | ¹H NMR | ¹³C NMR |
|---|---|---|---|
| | | 56<AX>), 3.09-3.19 (m, 2 H, 43<''>, 33<''>), 3.25 (t, J = 11.8 Hz, 1 H, 33<'>), 3.35-3.50 (m, 4 H, 56<EQ>, 56<EQ>,43<'>,63<''>), 3.55-3.62 (m, 1 H, 28<''>), 3.61-3.66 (m, 1 H, 23<''>), 3.61-3.66 (m, 1 H, 28<'>), 3.70 (dd, J = 13.5, 10.7 Hz, 1 H, 63<'>), 3.77-3.85 (m, 1 H, 29<''>), 3.85-3.94 (m, 1 H, 29<'>), 4.10 (dd, J = 7.7, 5.0 Hz, 1 H, 2), 4.50 (d, J = 12.3 Hz, 1 H, 23<'>), 4.60-4.70 (m, 2 H, 3, 5), 4.94 (s, 2 H, 48), 5.12 (q, J = 7.0 Hz, 1 H,1), 5.15-5.20 (m, 1 H, 24), 5.22 (td, J = 9.3, 6.8 Hz, 1 H, 4), 5.34 (dt, J = 11.2, 5.8 Hz, 1 H, 6), 6.89 (d, J = 8.4 Hz, 2 H, 46, 46), 7.07 (t, J = 7.5 Hz, 1 H, 70), 7.16-7.20 (m, 3 H, 45, 45, 16), 7.26 (d, J = 4.4 Hz, 4 H, 17, 15, 20, 14), 7.27-7.30 (m, 2 H, 36, 69), 7.30 (t, J = 7.3 Hz, 1 H, 59), 7.36 (t, J = 7.5 Hz, 2 H, 58, 58), 7.45 (d, ] = 7.3 Hz, 2 H, 50, 50), 7.48 (br. s., 1 H, 65), 7.75 (d, J = 7.9 Hz, 1 H, 71), 7.78 (d, J = 8.1 Hz, 1 H, 68), 7.92 (d, J = 7.5 Hz, 1 H, 35), 8.10 (d, J = 9.4 Hz, 1 H, 42), 8.60 (dd, J = 5.0, 1.3 Hz, 1 H, 37), 8.60-8.63 (m, 1 H, 39), 9.15 (d, J = 7.3 Hz, 1 H, 12), 9.43 (br. s., 1 H, 32), 9.55 (d, J = 6.6 Hz, 1 H, 62), 10.12 (d, J = 7.5 Hz, 1 H, 52), 12.04 (br. s., 1 H, 66) ppm | (28), 43.5 (56, 56), 51.8 (23), 52.6 (3), 53.2 (4), 53.8 (1), 54.3 (5), 55.6 (6), 60.2 (2), 70.0 (48), 72.0 (24), 110.4 (64), 112.3 (68), 114.8 (46, 46), 119.3 (71), 119.5 (70), 122.0 (69), 124.4 (36), 124.8 (65), 126.3 (16), 128.0 (50, 50), 128.1 (72), 128.2 (59), 128.9 (17, 15, 20, 14), 128.9 (58, 58), 130.1 (44), 131.1 (45, 45), 132.3 (34), 137.5 (67), 137.8 (49), 138.1 (35), 142.1 (13), 148.7 (37), 150.7 (39), 157.0 (26), 157.9 (47), 170.9 (31), 171.3 (21), 171.7 (11), 172.5 (41), 173.0 (51), 173.9 (61) ppm |
| 15 | FIG. 2 | ¹H NMR (600 MHz, Pyr): δ = 0.98 (dt, J = 14.1, 8.3 Hz, 1 H, 53<''>), 1.04 (br. s., 1 H, 54<AX>), 1.25-1.38 (m, 2 H, 53<'>, 55<AX>), 1.37-1.43 (m, 1 H, 55<EQ>), 1.42-1.55 (m, 1 H, 55<AX>), 1.72 (d, J = 14.3 Hz, 1 H, 55<EQ>), 2.23-2.33 (m, J = 14.1, 9.5, 9.5, 5.5 Hz, 1 H, 18<''>), 2.60 (ddd, J = 13.9, 10.6, 4.6 Hz, 1 H, 25<''>), 2.70 (dd, J = 13.7, 6.5 Hz, 1 H, 25<'>), 2.72-2.77 (m, J = 14.1, 6.6, 3.7, 3.7 Hz, 1 H, 18<'>), 2.81 (td, J = 12.7, 2.8 Hz, 1 H, 56<AX>), 2.94 (br. s., 2 H, 56<AX>, 19<''>), 2.98-3.11 (m, 2 H, 19<'>, 33<''>), 3.35-3.41 (m, 1 H, 43<''>), 3.40-3.48 (m, 4 H, 33<'>, 63<''>, 56<EQ>, 56<EQ>), 3.57 (ddd, J = 12.5, 6.0, 5.0 Hz, 1 H, 29<''>), 3.65 (ddd, J = 12.7, 7.3, 4.9 Hz, 1 H, 29<'>), 3.70 (br. s., 2 H, 43<'>, 23<''>), 3.86-3.94 (m, 3 H, 28<''>, 28<'>, 23<'>), 4.13 (d, J= 12.3 Hz, 1 H, 63<'>), 4.54 (ddd, J = 8.8, 6.8 Hz, 1 H, 5), 4.86 (q, J = 6.1 Hz, 1 H, 3), 4.88-4.92 (m, 1 H, 6), 4.91-4.95 (m, 1 H, 4), 5.00 (t, J = 10.6, 6.5 Hz, 1 H, 2), 5.02-5.06 (m, J = 11.7 Hz, 1 H, 48<''>), 5.06-5.10 (m, J = 11.7 Hz, 1 H, 48<'>), 5.23 (td, J = 9.7, 3.8 Hz, 1 H, 1), 5.56 (t, J = 3.7 Hz, 1 H, 24), 7.02 (d, J = 8.4 Hz, 2 H, 46, 46), 7.07 (t, J = 7.5 Hz, 1 H, 70), 7.18-7.21 (m, 1 H, 16), 7.26 (t, J = 7.9 Hz, 1 H, 69), 7.28-7.30 (m, 5 H, 18, 17, 15, 14, 36), 7.30-7.34 (m, 3H, 45, 45, 59), 7.37 (d, J = 1.7 Hz, 1 H, 65), 7.38 (t, J = 7.2 Hz, 2 H, 58, 58), 7.51 (d, J = 7.2 Hz, 2 H, 50, 50), 7.72 (d, J = 8.1 Hz, 1 H, 68), 7.96 (dt, J = 7.9, 1.7, 1.3 Hz, 1 H, 35), 8.09 (d, J = 7.5 Hz, 1 H, 71), 8.14 (br. s., 1 H, 32), 8.34 (br. s., 1 H, 52), 8.53 (dd, J = 4.8, 1.7 Hz, 1 H, 37), 8.72 (br. s., 1 H, 62), 8.79 (d, J = 1.3 Hz, 1 H, 39), 8.92 (t, J = 5.8 Hz, 1 H, 27), 9.28 (br. s., 1 H, 42), 10.46 (br. s., 1 H, 12), 11.81 (d, J = 1.3 Hz, 1 H, 66) ppm | ¹³C NMR (151 MHz, Pyr): δ = 28.5 (55), 29.6 (55), 30.3 (63), 30.6 (54), 32.2 (19), 33.4 (33), 34.8 (18, 25), 35.6 (43), 38.7 (53), 39.9 (28), 40.6 (29), 43.9 (56, 56), 52.0 (3), 52.5 (5), 54.1 (23), 54.6 (1), 57.6 (4, 6), 61.5 (2), 70.6 (48), 74.8 (24), 111.6 (64), 112.6 (68), 115.5 (46, 46), 119.9 (70), 120.0 (71), 122.5 (69), 124.1 (36), 124.8 (65), 125.5 (16), 128.5 (50, 50), 128.8 (72, 59), 129.3 (15, 17), 129.4 (14, 20), 129.5 (58, 58), 131.3 (45, 45), 132.1 (44), 132.7 (34), 137.8 (67), 138.1 (49), 139.1 (35), 142.5 (13), 148.8 (37), 152.1 (39), 158.4 (47), 169.5 (31), 170.3 ( ), 171.1 ( ), 172.1 ( ), 172.5 ( ), 173.2 ( ), 173.8 ( ) ppm |
| 14 | FIG. 3 | ¹H NMR (600 MHz, Pyr): δ = 1.78-1.86 (m, 1 H, 25<''>), 2.20-2.30 (m, 2 H, 55<''>, 55<''>), 2.38-2.47 (m, 3 H, 18<''>, 55<'>, 55<'>), 2.48-2.56 (m, 1 H, 18<'>), 2.57-2.69 (m, 3 H, 25<'>, 53), 2.74-2.86 (m, 2 H, 19), 3.12-3.23 (m, 6 H, 56, 56, 33<''>, 43<''>), 3.27 (t, J = 12.5 Hz, 1 H, 33<'>), 3.39 (d, J = 10.6 Hz, 2 H, 63<''>, 43<''>), 3.56-3.68 (m, 4 H, 63<'>, 23<''>, 28), 3.79-3.86 (m, 1 H, 29<''>), 3.86-3.93 (m, 1 H, 29<'>), 4.09 (t, J = 6.8 Hz, 1 H, 2), 4.53 (d, J = 12.8 Hz, 1 H, 23<'>), 4.71 (dt, J = 8.4, 4.2 Hz, 1 H, 5), 4.74 (br. s., 1 H, 3), 4.97 (s, 2 H, 48), 5.03 (q, J = 7.0 Hz, 1 H, 1), 5.20 (br. s., 1 H, 24), 5.21-5.27 (m, 2 H, 6, 4), 6.95 (d, J= 8.3 Hz, 2 H, 46, 46), 7.10 (t, J = 7.5 Hz, 1 H, 70), 7.18 (quin, J = 4.4 Hz, 1 H, 16), 7.23-7.27 (m, 7 H, 69, 14, 20, 15, 17, 45, 45), 7.27-7.31 (m, 1 H, 36), 7.30 (t, J = 7.3 Hz, 1 H, 59), 7.36 (t, J = 7.5 Hz, 2 H, 58, 58), 7.46 (d, J = 7.3 Hz, 2 H, 50, 50), 7.48 (br. s., 1 H, 65), 7.71 (d, J = 8.3 Hz, 1 H, 68), 7.78 (d, J = 8.1 Hz, 1 H, 71), 7.95 (d, J = 7.2 Hz, 1 H, 35), 8.10 (d, J = 9.0 Hz, 1 H, 42), 8.57-8.65 (m, | ¹³C NMR (151 MHz, Pyr): δ = 28.4 (63), 32.5 (19), 34.0 (18), 35.4 (33), 36.9 (43), 37.7 (25), 39.5 (29), 40.1 (28), 43.1 (56, 56), 49.8 (55, 55), 51.8 (23), 53.2 (4), 53.3 (1), 53.5 (5), 54.6 (3), 55.7 (6), 58.4 (53), 60.2 (2), 70.0 (48), 72.1 (24), 110.4 (64), 112.5 (68), 114.9 (46, 46), 119.2 (71), 119.3 (70), 121.9 (69), 124.4 (36), 124.7 (65), 126.4 (16), 128.0 (50, 50), 128.2 (59), 128.3 (72), 128.9 (15, 17, 14, 20, 58, 58), 130.2 (44), 131.0 (45, 45), 132.3 (34), |

TABLE 3-continued

¹H NMR and ¹³C NMR analysis for selected Examples

Figure 4:
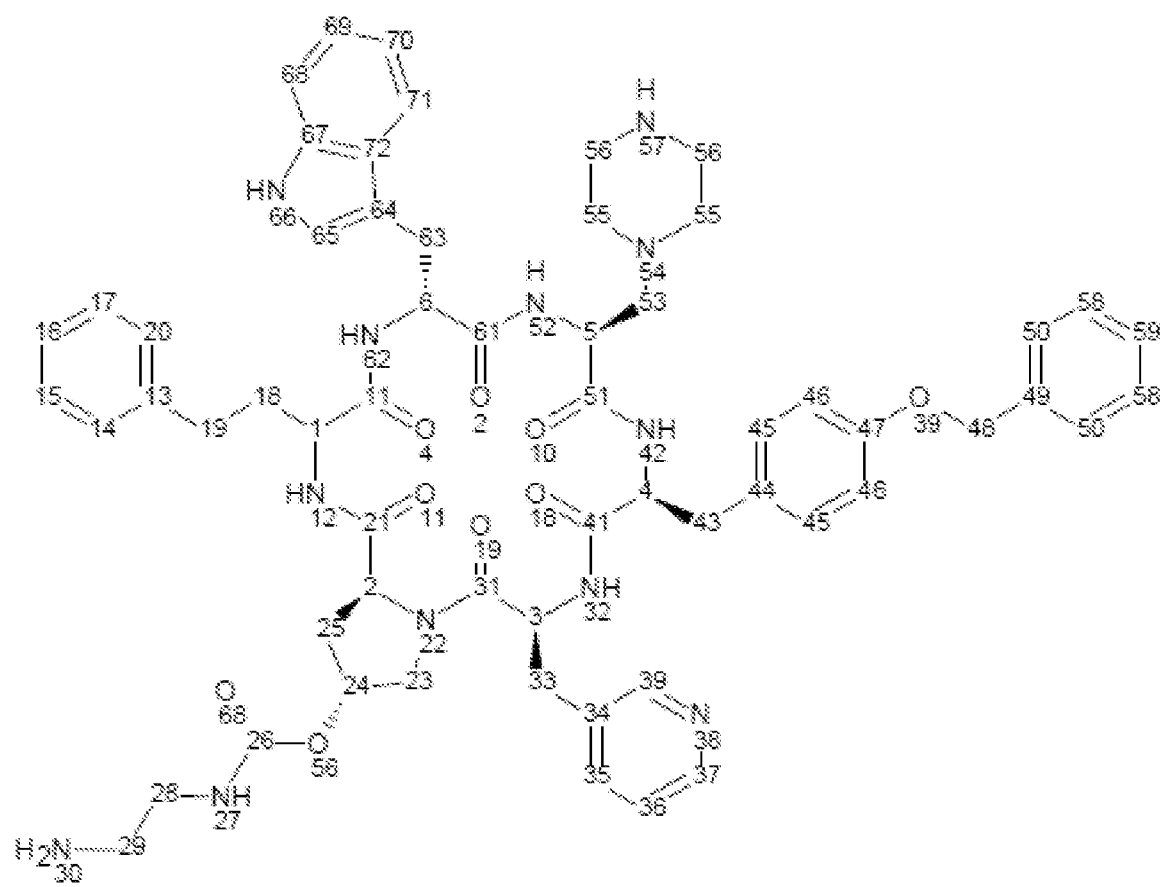
Figure 5:
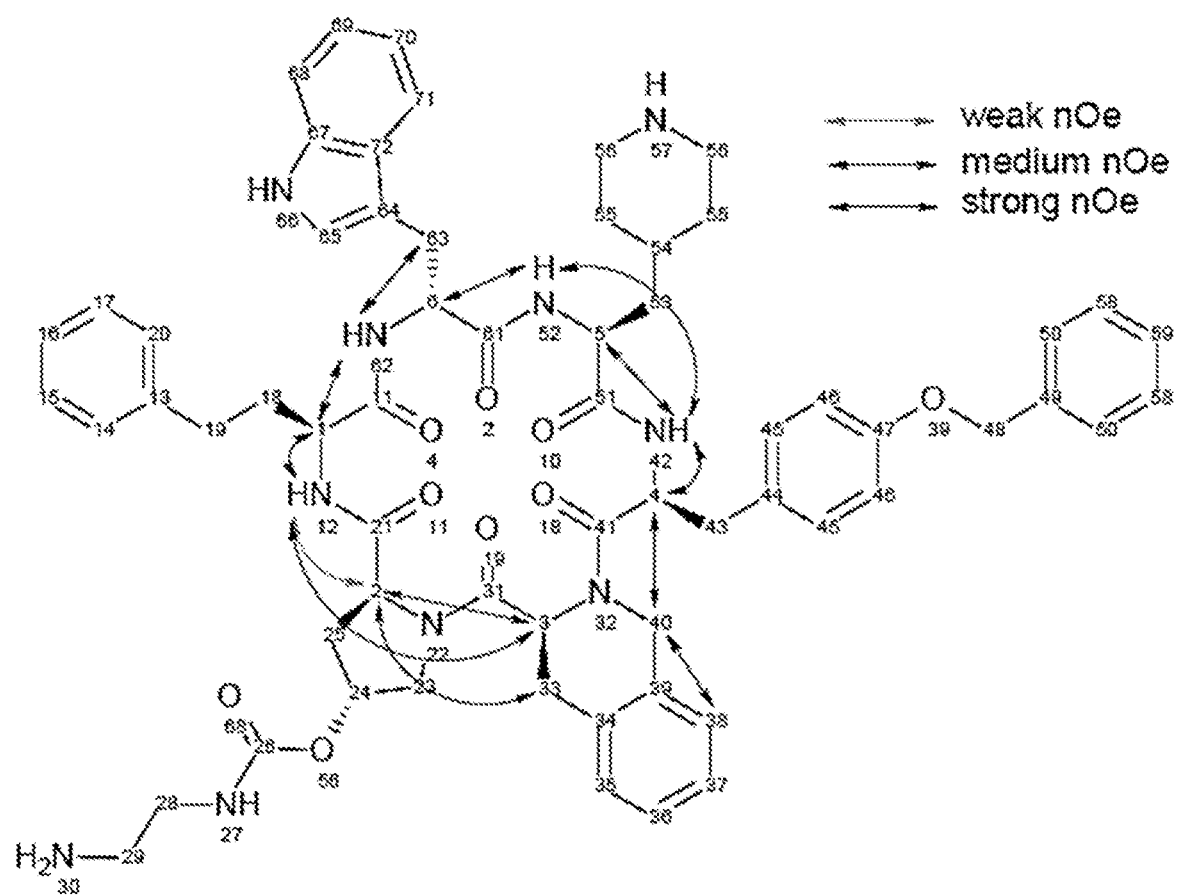

| Example | Structure | ¹H NMR | ¹³C NMR |
|---|---|---|---|
| | | 2 H, 37, 39), 8.76 (t, J = 5.4 Hz, 1 H, 27), 9.18 (br. s., 2 H, 62, 12), 9.29 (br. s., 1 H, 32), 9.95 (d, J = 4.8 Hz, 1 H, 52), 12.00 (br. s., 1 H, 66) ppm | 137.5 (67), 137.8 (49), 138.1 (35), 142.1 (13), 148.5 (37), 150.5 (39), 157.0 (26), 158.0 (47), 170.9 (31), 171.5 (11, 21), 172.1 (51), 172.6 (41), 174.2 (61) ppm |
| 16 | FIG. 4 | ¹H NMR (600 MHz, Pyr): δ = 2.24 (dd, J = 12.7, 7.0 Hz, 2 H, 18<">, 53<">), 2.31-2.40 (m, 2 H, 55<AX>, 55<AX>), 2.39-2.46 (m, 2 H, 55<EQ>, 55<EQ>), 2.49 (dd, J = 12.6, 7.4 Hz, 1 H, 53<'>), 2.60 (ddd, J = 13.8, 9.2, 4.0 Hz, 1 H, 25<">), 2.67 (ddd, J = 13.2, 6.6, 1.0 Hz, 1 H, 25<'>), 2.72 (dddd, J = 14.1, 10.3, 6.6, 4.4 Hz, 1 H, 18<'>), 2.92 (ddd, J = 14.1, 9.0, 6.9 Hz, 1 H, 19<">), 3.01 (ddd, J = 14.1, 9.0, 4.6 Hz, 1 H, 19<'>), 3.09 (dd, J = 13.9, 5.5 Hz, 1 H, 33<">), 3.16 (br. s., 4 H, 56, 56), 3.44 (dd, J = 14.2, 5.2 Hz, 1 H, 33<'>), 3.51 (t, J = 12.7 Hz, 1 H, 43<">), 3.53-3.57 (m, J = 13.2, 9.4 Hz, 1 H, 63<">), 3.57 (dt, J = 12.1, 5.1, 5.0 Hz, 1 H, 29<">), 3.64 (ddd, J = 12.6, 7.7, 4.9 Hz, 1 H, 29<'>), 3.71 (dd, J = 14.3, 2.8 Hz, 1 H, 43<'>), 3.72-3.77 (m, J = 12.1 Hz, 1 H, 23<">), 3.79-3.92 (m, 3 H, 23<'>, 28), 4.02 (dd, J = 14.3, 3.6 Hz, 1 H, 63<'>), 4.68 (q, J = 6.7 Hz, 1 H, 5), 4.76 (br. s., 1 H, 4), 4.90 (ddd, J = 8.8, 3.8 Hz, 1 H, 6), 4.94 (q, J = 6.2 Hz, 1 H, 3), 4.99 (dd, J = 9.2, 1.7 Hz, 1 H, 2), 5.12 (s, 2 H, 48), 5.18 (td, J = 9.7, 4.0 Hz, 1 H, 1), 5.55 (quin, J = 3.0 Hz, 1 H, 24), 7.02 (t, J = 8.1, 7.2 Hz, 1 H, 70), 7.08 (d, J = 8.4Hz, 2 H, 46, 46), 7.17-7.21 (m, 2 H, 16, 69), 7.26 (d, J = 6.6 Hz, 2 H, 14, 20), 7.29 (t, J = 7.0 Hz, 2 H, 15, 17), 7.29-7.32 (m, 1 H, 36), 7.33 (d, J = 7.3 Hz, 1 H, 59), 7.35 (d, J = 8.4 Hz, 2 H, 45, 45), 7.40 (t, J = 7.4 Hz, 2 H, 58, 58), 7.41 (d, J = 1.8 Hz, 1 H, 65), 7.55 (d, J = 7.4 Hz, 2 H, 50, 50), 7.61 (d, J = 8.1 Hz, 1 H, 68), 7.97 (dt, J = 7.9, 1.5 Hz, 1 H, 35), 8.08 (d, J = 8.1 Hz, 1 H, 71), 8.19 (br. s., 1 H, 32), 8.56 (dd, J = 4.8, 1.7 Hz, 1 H, 37), 8.63 (br. s., 1 H, 52), 8.67 (d, J = 2.6 Hz, 1 H, 62), 8.84 (d, J = 1.5 Hz, 1 H, 39), 8.87 (t, J = 5.7 Hz, 1 H, 27), 9.65 (br. s., 1 H, 42), 10.38 (br. s., 1 H, 12), 11.85 (d, J = 1.8 Hz, 1 H, 66) ppm | ¹³C NMR (151 MHz, Pyr): δ = 30.1 (63), 33.4 (19), 35.1 (33), 35.6 (25), 35.6 (18), 37.0 (43), 39.9 (28), 40.6 (29), 43.5 (56, 56), 50.6 (55, 55), 53.0 (3), 54.0 (5, 23), 54.6 (1), 57.6 (6), 58.4 (4), 59.0 (53), 61.4 (2), 70.6 (48), 74.9 (24), 111.6 (64), 112.5 (68), 115.6 (46, 46), 120.1 (70), 120.4 (71), 122.3 (69), 124.3 (36), 125.1 (65), 126.8 (16), 128.6 (50, 50), 128.7 (59), 129.3 (17, 15), 129.3 (72), 129.4 (58, 58), 129.5 (20, 14), 131.3 (45, 45), 132.3 (44), 132.8 (34), 137.8 (67), 138.3 (49), 139.3 (35), 142.5 (13), 148.6 (37), 151.9 (39), 157.4 (26), 158.6 (47), 169.7 (31), 171.1 (41), 172.1 (21), 172.5 (61), 173.0 (51), 173.2 (11) ppm |
| 17 | FIG. 5 | ¹H NMR (600 MHz, Pyr): δ = 1.09-1.19 (m, 1 H, 54<AX>), 1.29-1.40 (m, 2 H, 55<AX>, 55<AX>), 1.38-1.45 (m, 1 H, 53<">), 1.49 (d, J = 13.2 Hz, 1 H, 55<EQ>), 1.80 (d, J = 13.8 Hz, 1 H, 55<EQ>), 1.93 (ddd, J = 14.0, 10.2, 3.9 Hz, 1 H, 53<'>), 2.47-2.56 (m, 1 H, 18<">), 2.56-2.65 (m, 1 H, 18<'>), 2.73 (ddd, J =12.5, 8.3, 3.7 Hz, 1 H, 25<">), 2.82 (dt, J = 13.8, 5.0 Hz, 1 H, 25<'>), 2.90-3.05 (m, 5 H, 56<AX>, 56<AX>, 19<">, 19<'>, 33<">), 3.08 (dd, J = 13.9, 7.0 Hz, 1 H, 43<">), 3.25 (dd, J = 15.3, 6.1 Hz, 1 H, 33<'>), 3.37-3.49 (m, 4 H, 43<'>, 63<">, 56<EQ>, 56<EQ>), 3.58 (t, J = 5.9 Hz, 2 H, 29), 3.64 (dd, J = 12.8, 5.0 Hz, 1 H, 23<">), 3.73 (dd, J = 13.5, 11.3 Hz, 1 H, 63<'>), 3.77-3.89 (m, 2 H, 28), 4.37 (dd, J = 8.6, 6.2 Hz, 1 H, 3), 4.42 (dd, J = 13.0, 1.3 Hz, 1 H, 23<'>), 4.44 (d, J = 14.3 Hz, 1 H, 40<">), 4.71 (d, J = 14.7 Hz, 1 H, 40<'>), 4.78 (ddd, J = 11.2, 7.7, 3.9 Hz, 1 H, 5), 4.95 (s, 2 H, 48), 5.05 (dd, J = 8.6, 5.0 Hz, 1 H, 2), 5.28 (quin, J = 4.4 Hz, 1 H, 24), 5.35 (q, J = 6.3 Hz, 1 H, 1), 5.58 (ddd, J = 11.1, 7.4, 5.7 Hz, 1 H, 6), 5.66 (q, J = 7.3 Hz, 1 H, 4), 6.94 (d, J = 8.6 Hz, 2 H, 46, 46), 7.01 (ddd, J = 8.0, 7.2, 0.7 Hz, 1 H, 70), 7.03 (d, J = 7.2 Hz, 1 H, 38), 7.17 (td, J = 7.3, 1.1 Hz, 1 H, 37), 7.19 (td, J = 6.1, 2.4 Hz, 1 H, 16), 7.22 (t, J = 7.5 Hz, 1 H, 36), 7.25 (d, J = 6.6 Hz, 1 H, 35), 7.26-7.28 (m, 5 H, 69, 20, 14, 17, 15), 7.28-7.30 (m, 1 H, 59), 7.35 (t, J = 7.4 Hz, 2 H, 58, 58), 7.40 (d, J = 8.6 Hz, 2 H, 45, 45), 7.41 (d, J = 2.2 Hz, 1 H, 65), 7.45 (d, J = 7.0 Hz, 2 H, 50, 50), 7.69 (d, J = 8.1 Hz, 1 H, 71), 7.80 (d, J = 8.1 Hz, 1 H, 68), 8.13 (d, J = 8.3 Hz, 1 H, 42), 8.79 (t, J = 5.9 Hz, 1 H, 27), 8.94 (d, J = 6.2 Hz, 1 H, 12), 10.05 (d, J = 7.7 Hz, 1 H, 62), 10.17 (d, J = 7.9 Hz, 1 H, 52), 12.00 (d, J = 1.8 Hz, 1 H, 66) ppm | ¹³C NMR (151 MHz, Pyr): δ = 28.2 (55), 28.8 (63), 29.7 (55), 30.5 (54), 30.6 (33), 32.3 (19), 36.0 (18), 38.3 (53), 38.6 (25), 39.1 (43), 39.5 (28), 40.1 (29), 43.3 (56), 43.4 (56), 46.6 (40), 51.0 (4), 51.6 (5), 52.1 (23), 54.3 (1), 55.1 (6), 55.2 (3), 60.5 (2), 69.9 (48), 72.2 (24), 110.5 (64), 112.3 (68), 115.0 (46, 46), 119.4 (71), 119.5 (70), 122.0 (69), 124.7 (65), 126.2 (38), 126.3 (16), 127.1 (37), 127.7 (35), 128.0 (50, 50), 128.2 (72), 128.2 (59, 36), 128.9 (20, 14, 15, 17), 129.0 (58, 58), 129.5 (44), 131.7 (45, 45), 134.5 (34), 134.9 (39), 137.5 (67), 137.8 (49), 142.2 (13), 157.1 (26), 158.1 (47), 170.7 (41), 170.9 (11), 171.4 (21, 31), 171.5 (51), 173.4 (61) ppm |

TABLE 3-continued

¹H NMR and ¹³C NMR analysis for selected Examples

Figure 6:
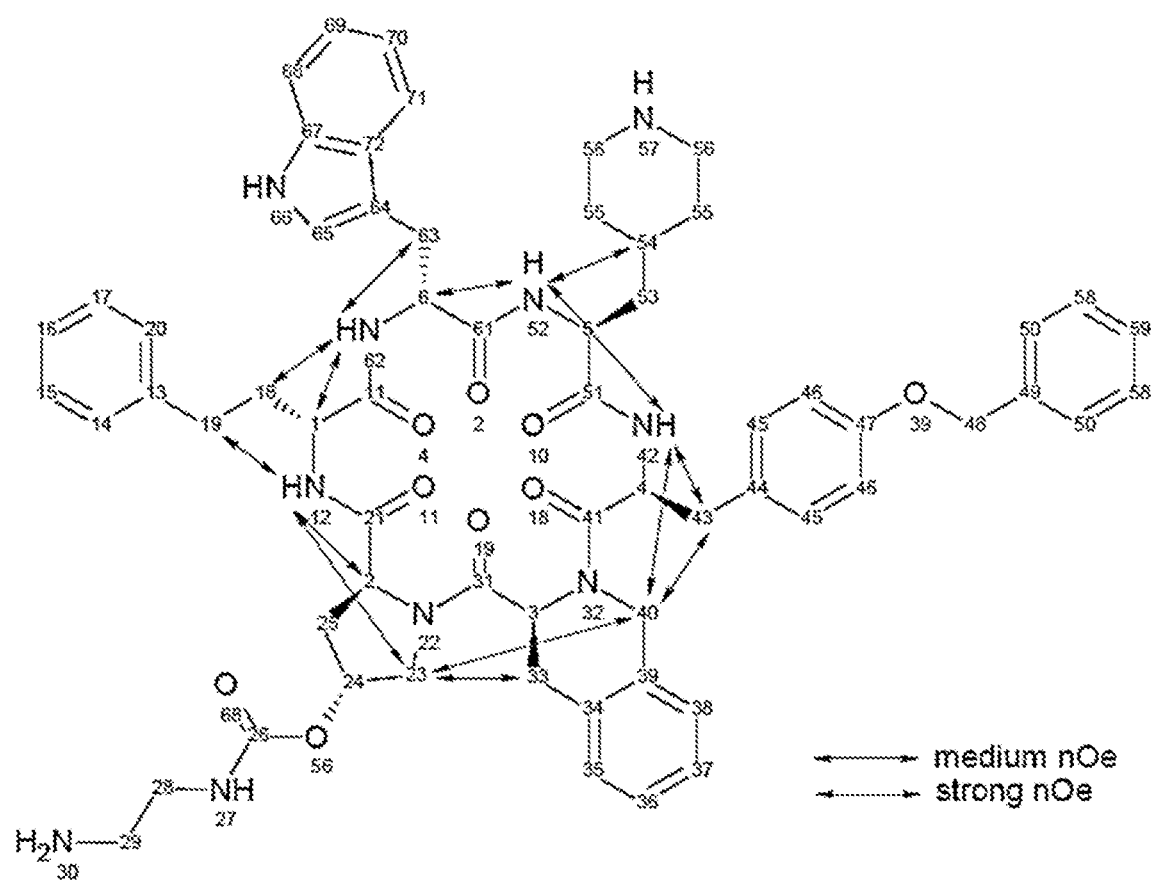
Figure 7:
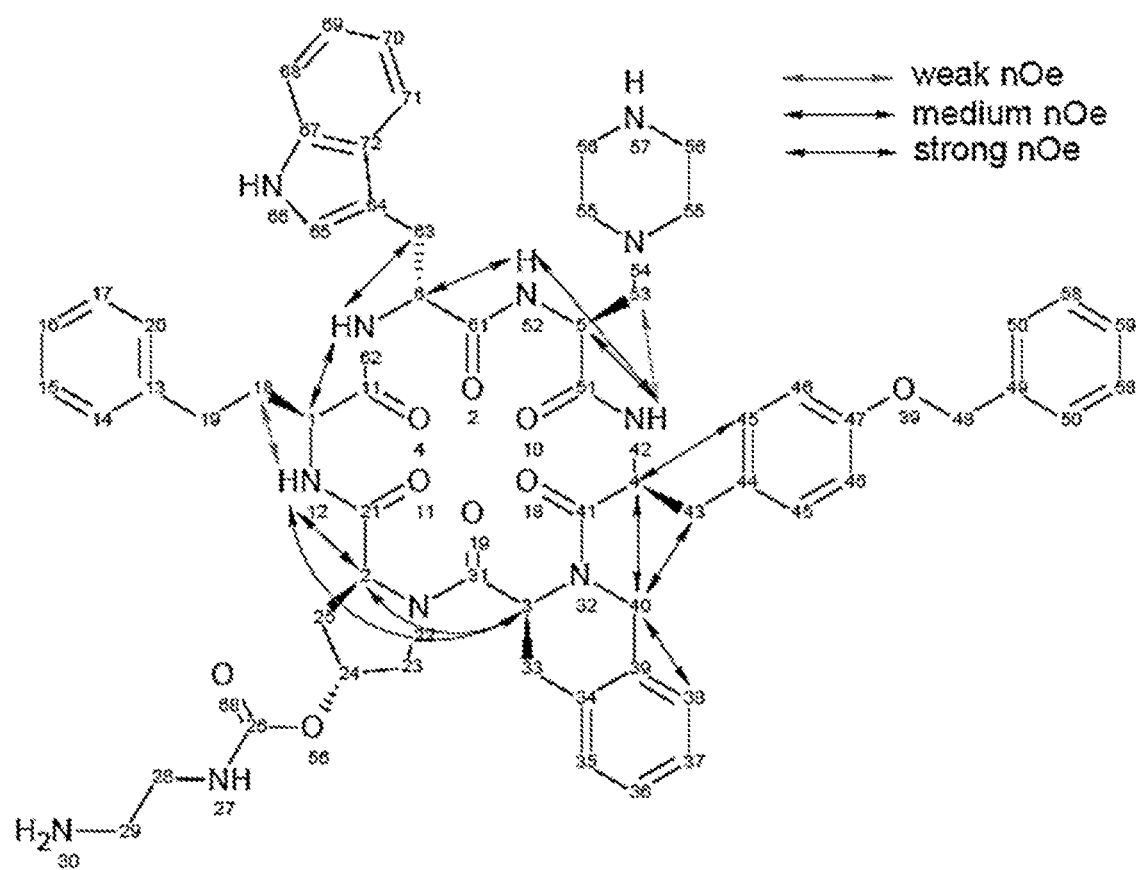

| Example | Structure | ¹H NMR | ¹³C NMR |
|---|---|---|---|
| 21 | FIG. 6 | ¹H NMR (600 MHz, Pyr): δ = 0.96-1.07 (m, 1 H, 54<AX>), 1.11-1.37 (m, 6 H, 54<AX>, 55<AX>, 53<">), 1.43 (d, J = 13.4 Hz, 1 H, 55<EQ>), 1.45-1.54 (m, 2 H, 53<">, 55<EQ>), 1.73 (d, J = 12.5 Hz, 1 H, 55<EQ>), 1.81-1.93 (m, 2 H, 53<">, 55<EQ>), 2.06 (ddd, J = 13.8, 10.8, 2.9 Hz, 1 H, 53<'>), 2.29 (ddd, J = 14.2, 9.4, 4.5 Hz, 1 H, 25<">), 2.42-2.52 (m, 1 H, 18<">), 2.56-2.67 (m, 2 H, 19<">, 18<'>), 2.71 (dd, J = 13.8, 8.9 Hz, 1 H, 25<'>), 2.90 (br. s., 8 H, 56<AX>, 25<">, 25<'>, 19<'>, 18), 3.01-3.11 (m, 3 H, 56<AX>, 33), 3.15 (dd, J = 15.3, 7.6 Hz, 1 H, 33<">), 3.26 (dd, J = 14.2, 6.9 Hz, 1 H, 43<">), 3.29-3.39 (m, 7 H, 43<'>, 33<'>, 56<EQ>, 56<EQ>, 63<">), 3.41 (dd, J = 13.6, 4.2 Hz, 1 H, 63<">), 3.53 (br. s., 2 H, 19<">, 43<">), 3.56-3.64 (m, 5 H, 19<'>, 29), 3.67 (dd, J = 14.3, 11.9 Hz, 1 H, 63<'>), 3.77 (d, J = 12.8 Hz, 1 H, 43<'>), 3.79-3.92 (m, 5 H, 63<'>, 28), 3.99 (dd, J = 12.6, 5.4 Hz, 1 H, 23<">), 4.17 (br. s., 2 H, 23), 4.33 (dd, J = 13.0, 2.9 Hz, 1 H, 23<'>), 4.47 (dd, J = 10.5, 7.1 Hz, 1 H, 3), 4.62 (d, J = 14.9 Hz, 1 H, 40<">), 4.68 (br. s., J = 11.0, 7.0, 3.9 Hz, 1 H, 5), 4.97 (s, 2 H, 48), 4.97-5.01 (m, 4 H, 40<">, 5, 48), 5.06 (br. s., J = 14.7 Hz, 1 H, 40<'>), 5.08 (d, J = 14.7 Hz, 1 H, 40<'>), 5.16 (td, J = 7.2, 4.3 Hz, 1 H, 1), 5.30 (t, J = 8.8 Hz, 1 H, 2), 5.36 (dd, 2 H, 3, 6), 5.37-5.42 (m, 2 H, 2, 6), 5.45 (dt, J = 9.6, 4.9 Hz, 1 H, 24), 5.50 (br. s., 1 H, 24), 5.57 (dt, J = 8.6, 4.4 Hz, 1 H, 1), 5.72 (q, J = 7.3 Hz, 1 H, 4), 6.00 (t, J = 10.7 Hz, 1 H, 4), 6.84 (d, J = 8.6 Hz, 2 H, 46, 46), 6.91 (t, J = 7.4 Hz, 1 H, 70), 7.01 (d, J = 7.2 Hz, 1 H, 38), 7.04 (d, J = 7.2 Hz, 1 H, 35), 7.04 (d, J = 8.6 Hz, 2 H, 46, 46), 7.07 (d, J = 7.0 Hz, 1 H, 70), 7.08 (d, J = 7.2 Hz, 2 H, 38, 35), 7.10-7.14 (m, 1 H, 16), 7.13-7.18 (m, 5 H, 20, 17, 16, 15, 14), 7.18-7.21 (m, 2 H, 69, 37), 7.23 (d, 3 H, 36, 17, 15), 7.25-7.30 (m, 3 H, 37, 69, 36), 7.30-7.36 (m, 2 H, 59), 7.38 (t, J = 7.5 Hz, 4 H, 58, 58), 7.39 (br. s., 1 H, 65), 7.42 (s, 1 H, 65), 7.45 (d, J = 7.2 Hz, 4 H, 50, 50), 7.50 (d, J = 8.6 Hz, 3 H, 71, 45, 45), 7.53 (d, J = 8.4 Hz, 2 H, 45, 45), 7.71 (d, J = 7.2 Hz, 2 H, 14, 20), 7.74 (d, J = 8.1 Hz, 1 H, 68), 7.78 (d, J = 8.1 Hz, 1 H, 68), 7.81 (d, J = 7.7 Hz, 1 H, 71), 8.24 (d, J = 8.8 Hz, 1 H, 42), 8.66 (d, J = 8.6 Hz, 1 H, 12), 8.83 (t, J = 5.8 Hz, 1 H, 27), 8.90 (d, J = 9.4 Hz, 1 H, 42), 9.05 (d, J = 7.9 Hz, 1 H, 62), 9.07 (t, J = 5.8 Hz, 1 H, 27), 9.59 (d, J = 4.6 Hz, 1 H, 62), 9.62 (d, J = 9.4 Hz, 1 H, 52), 9.82 (d, J = 7.3 Hz, 1 H, 52), 10.00 (d, J = 7.2 Hz, 1 H, 12), 11.92 (s, 2 H, 66) ppm | ¹³C NMR (126 MHz, Pyr): δ = 27.5 (63), 28.0 (63, 55), 28.3 (55), 29.5 (55), 30.0 (55), 30.0 (54), 30.4 (54), 30.5 (33), 30.9 (19), 31.0 (33), 31.4 (19), 35.0 (18), 35.4 (25), 37.1 (18), 37.9 (43), 38.2 (53), 38.4 (53, 25), 39.5 (43), 39.6 (28), 40.1 (29), 43.1 (56), 43.3 (56), 46.7 (40), 47.1 (40), 50.5 (5), 51.8 (4), 52.4 (23, 4), 52.6 (5), 53.1 (1), 54.1 (23), 54.3 (3), 54.6 (1), 55.9 (6), 57.2 (6), 60.2 (2), 61.0 (2), 61.2 (3), 69.9 (48), 70.0 (48), 72.3 (24), 74.3 (24), 110.3 (64), 110.9 (64), 112.1 (68), 114.9 (46, 46), 115.0 (46, 46), 119.0 (71), 119.5 (70, 71), 121.9 (69), 124.7 (65), 125.8 (16), 126.1 (16), 126.2 (38), 126.5 (38), 127.3 (37), 127.4 (35), 127.7 (37), 127.8 (35), 128.0 (36), 128.0 (50, 50), 128.1 (72), 128.2 (36), 128.3 (59), 128.6 (17, 15), 128.8 (20, 14, 17, 15), 128.9 (58, 58), 129.6 (14, 20), 129.7 (44), 130.0 (44), 130.9 (45, 45), 131.7 (45, 45), 133.8 (34), 134.0 (39), 134.2 (39), 135.1 (34), 137.4 (67), 137.7 (49), 142.2 (13), 144.3 (13), 157.1 (26), 158.1 (47), 170.6 (31, 21), 171.3 (31), 171.6 (51), 171.7 (41), 172.2 (51), 172.6 (41), 173.0 (61), 173.2 (61), 173.4 (11) ppm |
| 24 | FIG. 7 | ¹H NMR (600 MHz, Pyr): δ = 2.30-2.38 (m, 2 H, 55<AX>, 55<AX>), 2.43-2.48 (m, 1 H, 18<">), 2.47-2.52 (m, 2 H, 55<EQ>, 55<EQ>), 2.56 (dq, J = 10.2, 6.8 Hz, 1 H, 18<'>), 2.64 (dd, J = 12.9, 10.0 Hz, 1 H, 53<">), 2.68-2.74 (m, 1 H, 25<">), 2.73 (dd, J = 13.0, 3.7 Hz, 1 H, 53<'>), 2.81-2.86 (m, 1 H, 25<'>), 2.85-2.93 (m, 2 H, 19), 3.04 (dd, J = 15.2, 9.2 Hz, 1 H, 33<">), 3.11-3.16 (m, 1 H, 43<">), 3.15-3.22 (m, 4 H, 56, 56), 3.27 (dd, J = 15.2, 5.7 Hz, 1 H, 33<'>), 3.39 (dd, J = 13.6, 5.5 Hz, 1 H, 63<">), 3.40 (dd, J = 13.6, 6.2 Hz, 1 H, 43<'>), 3.58 (t, J = 5.9 Hz, 2 H, 29), 3.66 (dd, J = 13.8, 10.4 Hz, 1 H, 63<'>), 3.68 (dd, J = 12.3, 5.0 Hz, 1 H, 23<'>), 3.76-3.89 (m, 2 H, 28), 4.42 (d, J = 12.7 Hz, 1 H, 23<'>), 4.47 (dd, J = 8.8, 6.2 Hz, 1 H, 3), 4.54 (d, J = 14.3 Hz, 1 H, 40<">), 4.81 (ddd, J = 10.5, 6.8, 3.9 Hz, 1 H, 5), 4.83 (d, J = 14.9 Hz, 1 H, 40<'>), 4.97 (s, 2 H, 48), 5.07 (dd, J = 8.6, 5.1 Hz, 1 H, 2), 5.26 (q, J = 6.6 Hz, 1 H, 1), 5.29 (quin, J = 4.2 Hz, 1 H, 24), 5.46 (dt, J = 10.6, 7.2 Hz, 1 H, 6), 5.73 (dd, J = 14.8, 7.4 Hz, 1 H, 4), 6.98 (d, J = 8.6 Hz, 2 H, 46, 46), 7.04 (t, J = 7.9 Hz, 1 H, 70), 7.10 (d, J = 7.3 Hz, 1 H, 38), 7.16-7.19 (m, 1 H, 16), 7.18-7.20 (m, 1 H, 37), 7.22-7.24 (m, 3 H, 69, 36, 35), 7.24-7.26 (m, 4 H, 20, 17, 14, 15), 7.29 (t, J = 7.5 Hz, 1 H, 59), 7.35 (t, J = 7.4 Hz, 2 H, 58, 58), 7.40 (d, J = 2.2 Hz, 1 H, 65), 7.44 (d, J = 8.0 Hz, 2 H, 45, 45), 7.45 (d, J = 7.5 Hz, 2 H, 50, 50), 7.69 (d, J = 8.8 Hz, 1 H, 68), 7.69 (d, J = 7.9 Hz, 1 H, 71), 8.12 (d, J = | ¹³C NMR (151 MHz, Pyr): δ = 28.6 (63), 30.6 (33), 32.3 (19), 35.6 (18), 38.4 (25), 38.5 (43), 39.5 (28), 40.0 (29), 43.1 (56, 56), 46.7 (40), 50.0 (55, 55), 50.8 (4), 52.1 (23), 52.8 (5), 54.2 (1), 55.2 (6), 55.3 (3), 58.9 (53), 60.5 (2), 70.0 (48), 72.2 (24), 110.6 (64), 112.3 (68), 115.0 (46, 46), 119.2 (71), 119.3 (70), 121.9 (69), 124.6 (65), 126.2 (38), 126.3 (16), 127.2 (37), 127.6 (35), 128.0 (50, 50), 128.2 (59, 36), 128.3 (72), 128.8 (58, 58), 129.0 (15, 17, 14, 20), 129.6 (44), 131.7 (45, 45), 134.5 (39), 134.9 (34), 137.5 (67), 137.8 (49), 142.2 (13), 157.1 (26), 158.1 (47), 170.4 (51), 170.8 (41), 170.9 (11), 171.3 (31), 171.4 (21), 173.8 (61) |

TABLE 3-continued

¹H NMR and ¹³C NMR analysis for selected Examples

Figure 8:
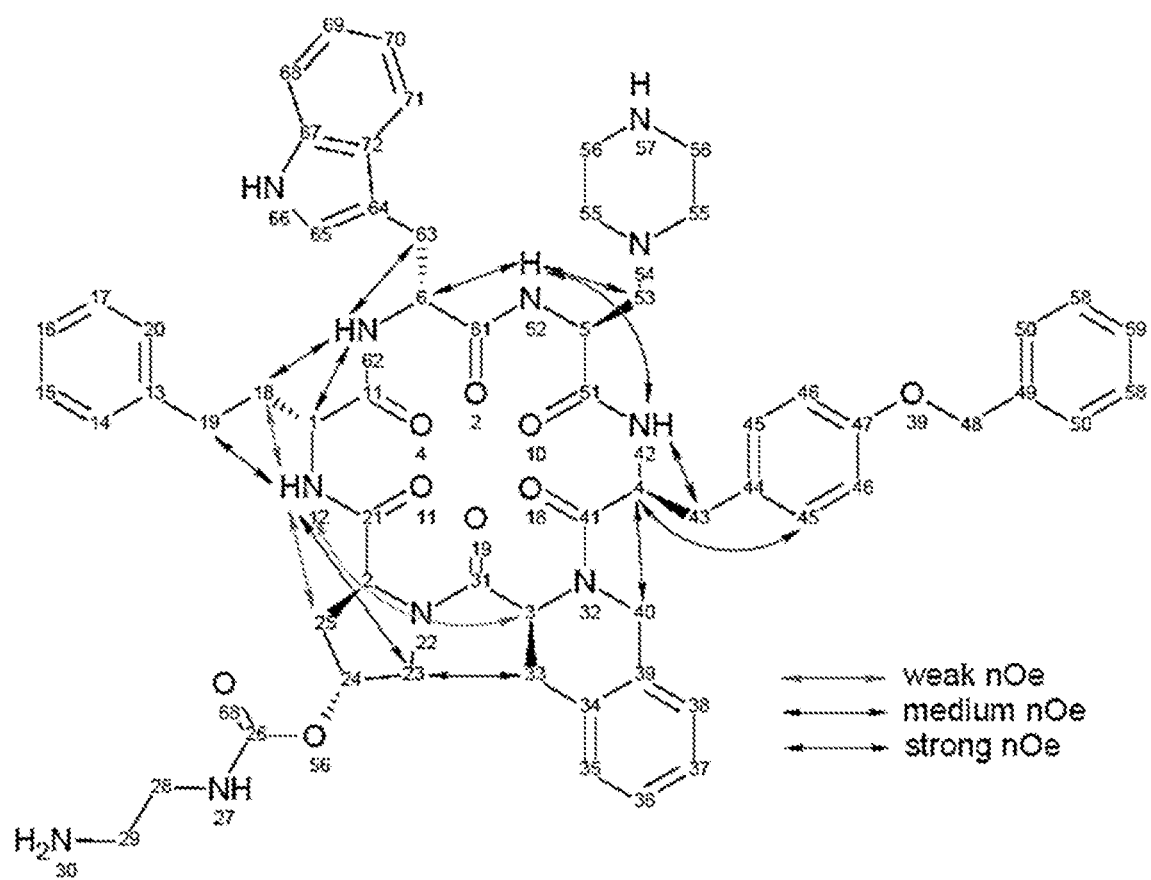
Figure 9:
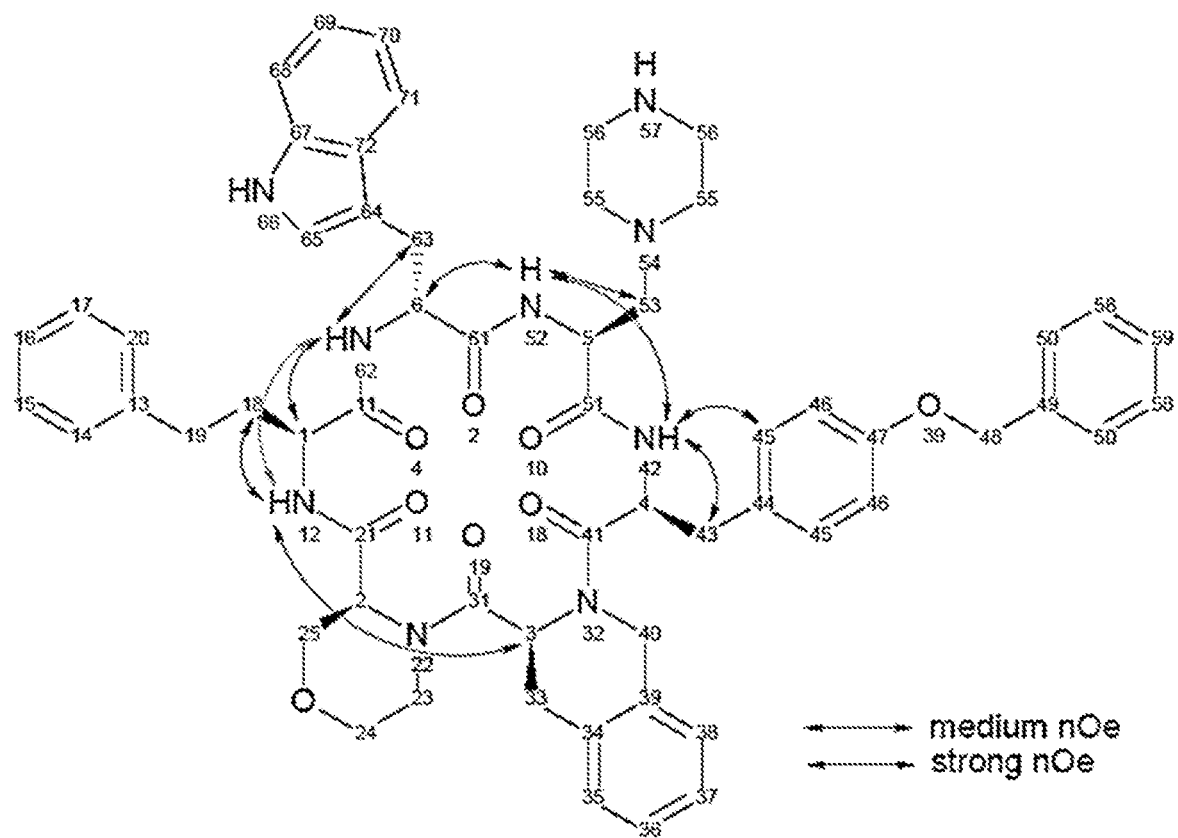

| Example | Structure | ¹H NMR | ¹³C NMR |
|---|---|---|---|
| | | 8.4 Hz, 1 H, 42), 8.81 (t, J = 5.8 Hz, 1 H, 27), 8.98 (d, J = 6.6 Hz, 1 H, 12), 9.78 (d, J = 7.2 Hz, 1 H, 62), 9.98 (d, J = 6.6 Hz, 1 H, 52), 11.93 (d, J = 1.5 Hz, 1 H, 66) ppm | ppm |
| 25 | FIG. 8 | ¹H NMR (600 MHz, Pyr): δ = 2.28 (ddd, J = 14.3, 9.4, 5.0 Hz, 1 H, 25<''>), 2.31-2.37 (m, 4 H, 55<AX>, 55<AX>), 2.37-2.49 (m, 5 H, 55<EQ>, 55<EQ>, 18<''>), 2.59-2.69 (m, 3 H, 53<''>, 18<'>), 2.68-2.78 (m, 4 H, 53<'>, 19<''>, 25<'>), 2.83-2.92 (m, 4 H, 25, 19<'>, 18), 3.09 (br. s., 10 H, 33, 56, 56), 3.17 (dd, J = 16.1, 6.4 Hz, 1 H, 33<''>), 3.24 (dd, J = 14.5, 7.3 Hz, 1 H, 43<''>), 3.32 (dd, J = 13.9, 5.1 Hz, 1 H, 43<'>), 3.35 (dd, J = 16.0, 6.4 Hz, 1 H, 33<'>), 3.40 (dd, J = 13.9, 4.8 Hz, 1 H, 63<''>), 3.45-3.52 (m, 2 H, 19<''>, 63<'>), 3.52-3.66 (m, 7 H, 63<'>, 19<'>, 43<''>, 29), 3.75-3.80 (m, 1 H, 43<'>), 3.80-3.84 (m, 1 H, 63<'>), 3.83-3.92 (m, 4 H, 28), 4.07 (dd, J = 12.8, 5.5 Hz, 1 H, 23<''>), 4.17 (br. s., 2 H, 23), 4.21 (dd, J = 12.3, 2.6 Hz, 1 H, 23<'>), 4.49 (dd, J = 11.3, 6.5 Hz, 1 H, 3), 4.63 (dt, J = 9.7, 5.0 Hz, 1 H, 5), 4.82 (d, J = 14.9 Hz, 1 H, 40<''>), 4.97 (d, J = 14.7 Hz, 1 H, 40<''>), 5.00 (d, 2 H, 48), 5.02 (d, 2 H, 48), 5.10 (d, J = 14.1 Hz, 1 H, 40<'>), 5.09-5.17 (m, 2 H, 5, 1), 5.21 (d, J = 14.9 Hz, 1 H, 40<'>), 5.25 (q, J = 5.5 Hz, 1 H, 6), 5.27-5.33 (m, 2 H, 6, 2), 5.44 (dd, J = 7.8, 6.3 Hz, 1 H, 2), 5.47-5.55 (m, 4 H, 3, 24, 1), 5.79 (dd, J = 15.1, 7.2 Hz, 1 H, 4), 6.06 (t, J = 11.6 Hz, 1 H, 4), 6.89 (d, J = 8.4 Hz, 2 H, 46, 46), 6.98 (t, J = 7.6 Hz, 1 H, 70), 7.03-7.06 (m, 1 H, 35), 7.05-7.09 (m, 3 H, 46, 46, 35), 7.07-7.10 (m, 2 H, 35, 70), 7.10-7.12 (m, 1 H, 16), 7.12-7.15 (m, 1 H, 16), 7.16 (br. s., 3 H, 37, 38), 7.19 (d, J = 7.9 Hz, 2 H, 20, 14), 7.20-7.21 (m, 3 H, 69, 37), 7.24 (d, 6 H, 15, 17, 36), 7.28-7.33 (m, 2 H, 59), 7.34-7.36 (m, 1 H, 65), 7.37 (d, J = 8.1 Hz, 4 H, 58, 58), 7.39 (d, J = 1.5 Hz, 1 H, 65), 7.43-7.50 (m, 6 H, 45, 45, 50, 50), 7.56-7.58 (m, 2 H, 45, 45), 7.58-7.60 (m, 1 H, 71), 7.64 (d, J = 8.3 Hz, 1 H, 68), 7.67 (d, J = 8.1 Hz, 1 H, 68), 7.69 (d, J = 7.3 Hz, 2 H, 20, 14), 7.85 (d, J = 8.1 Hz, 1 H, 71), 8.29 (d, J = 9.2 Hz, 1 H, 42), 8.62 (d, J = 8.6 Hz, 1 H, 12), 8.74-8.76 (m, 1 H, 62), 8.80 (t, J = 5.8 Hz, 1 H, 27), 8.93 (d, J = 9.5 Hz, 1 H, 42), 9.06 (t, J = 5.8 Hz, 1 H, 27), 9.27 (d, J = 6.1 Hz, 1 H, 52), 9.47 (d, J = 4.8 Hz, 1 H, 62), 9.51 (d, J = 8.8 Hz, 1 H, 52), 10.03 (d, J = 8.1 Hz, 1 H, 12), 11.87 (d, J = 2.0 Hz, 1 H, 66), 11.92 (d, J = 1.8 Hz, 1 H, 66) ppm | ¹³C NMR (151 MHz, Pyr): δ = 28.5 (63), 28.5 (63), 30.5 (33), 30.8 (19), 31.1 (33), 32.3 (19), 35.4 (18), 35.5 (25), 37.0 (18), 37.3 (43), 38.6 (25), 39.3 (43), 39.6 (28), 40.1 (29), 42.9 (56, 56), 43.1 (56, 56), 46.6 (40), 47.1 (40), 49.9 (55, 55), 50.2 (55, 55), 51.4 (4), 51.7 (5), 52.2 (4), 52.7 (23), 53.1 (1), 53.3 (3), 53.8 (5), 54.1 (23), 54.6 (1), 56.0 (6), 57.3 (6), 58.4 (53), 58.7 (73), 59.9 (2), 61.0 (2), 61.2 (3), 70.0 (48), 70.0 (48), 72.3 (24), 74.3 (24), 110.3 (64), 110.9 (64), 112.1 (68), 114.9 (46, 46), 115.1 (46, 46), 119.0 (71), 119.3 (71, 70), 119.5 (70), 121.8 (69), 124.5 (65), 124.7 (65), 125.8 (16), 126.2 (16), 126.6 (38), 127.0 (38), 127.5 (35), 127.6 (37), 127.7 (37), 127.9 (35), 128.1 (50, 50), 128.2 (59), 128.3 (59), 128.3 (72), 128.4 (72), 128.6 (36, 17, 15), 128.8 (58, 58), 128.9 (20, 14), 129.6 (20, 14), 129.9 (44), 130.9 (45, 45), 131.4 (45, 45), 133.6 (39), 134.0 (34), 134.2 (39), 135.2 (34), 137.4 (67), 137.7 (49), 137.8 (49), 142.1 (13), 144.3 (13), 157.1 (26), 157.3 (26), 158.1 (47), 170.6 (21), 170.8 (51), 170.9 (31), 171.2 (51), 171.3 (31), 171.7 (11), 171.8 (41), 172.4 (21), 172.5 (41), 173.0 (61), 173.3 (11), 173.6 (61) ppm |
| 31 | FIG. 9 | ¹H NMR (600 MHz, Pyr): δ = 2.30-2.40 (m, 2 H, 55<AX>, 55<AX>), 2.42-2.51 (m, 2 H, 55<EQ>, 55<EQ>), 2.55 (q, J = 7.6 Hz, 2 H, 18), 2.59-2.66 (m, J = 12.8, 9.8 Hz, 1 H, 53<''>), 2.66-2.74 (m, J = 13.1, 4.0 Hz, 1 H, 53<'>), 2.83-2.91 (m, 1 H, 19<''>), 2.91-2.99 (m, 1 H, 19<'>), 3.08 (dd, J = 14.2, 8.4 Hz, 1 H, 43<''>), 3.12-3.17 (m, 4 H, 56, 56), 3.17-3.24 (m, 2 H, 23<''>, 33<''>), 3.24-3.31 (m, J = 15.3, 5.8 Hz, 1 H, 33<'>), 3.40-3.50 (m, 3 H, 43<'>, 24<''>, 63<''>), 3.67 (dd, J = 11.0, 3.1 Hz, 1 H, 25<''>), 3.68-3.74 (m, J = 14.0, 10.7 Hz, 1 H, 63<'>), 3.86 (dd, J = 11.0, 2.7 Hz, 1 H, 24<'>), 4.57 (d, J = 14.6 Hz, 1 H, 40<''>), 4.59 (t, J = 7.4 Hz, 1 H, 3), 4.80 (d, J = 13.1 Hz, 1 H, 23<'>), 4.83-4.90 (m, 2 H, 2, 5), 5.00 (d, J = 14.3 Hz, 1 H, 40<'>), 5.00 (s, 2 H, 48), 5.11 (d, J = 11.0 Hz, 1 H, 25<'>), 5.36 (q, J = 6.7 Hz, 1 H, 1), 5.46 (dt, J = 10.4, 6.3 Hz, 1 H, 6), 5.88 (td, J = 8.0, 7.0 Hz, 1 H, 4), 6.97 (d, J = 8.5 Hz, 2 H, 46, 46), 7.04 (t, J = 7.3 Hz, 1 H, 70), 7.13 (d, J = 7.6 Hz, 1 H, 38), 7.14-7.19 (m, 1 H, 16), 7.21-7.23 (m, 4 H, 20, 14, 15, 17), 7.22-7.25 (m, 2 H, 37, 69), 7.28 (d, J = 5.8 Hz, 1 H, 59), 7.27 (br. s, 2 H, 35, 36), 7.34 (t, J = 7.6 Hz, 2 H, | ¹³C NMR (151 MHz, Pyr): δ = 28.4 (63), 31.5 (33), 32.5 (19), 36.2 (18), 39.2 (43), 40.2 (23), 43.1 (56, 56), 46.7 (40), 50.1 (55, 55), 50.6 (4), 52.6 (5), 53.2 (3), 55.0 (1), 55.6 (6), 57.9 (2), 58.9 (53), 66.8 (24), 67.6 (25), 70.0 (48), 110.7 (64), 112.2 (68), 115.0 (46, 46), 119.2 (71), 119.3 (70), 121.9 (69), 124.6 (65), 126.2 (16), 126.3 (38), 127.4 (37), 127.6 (35), 128.0 (50, 50), 128.2 (59), 128.3 (72), 128.3 (36), 128.8 (17, 15), 128.8 (20, 14), 128.9 (58, 58), 129.5 (44), 131.5 (45, 45), 134.7 (34), 135.0 |

TABLE 3-continued

¹H NMR and ¹³C NMR analysis for selected Examples

Figure 10:
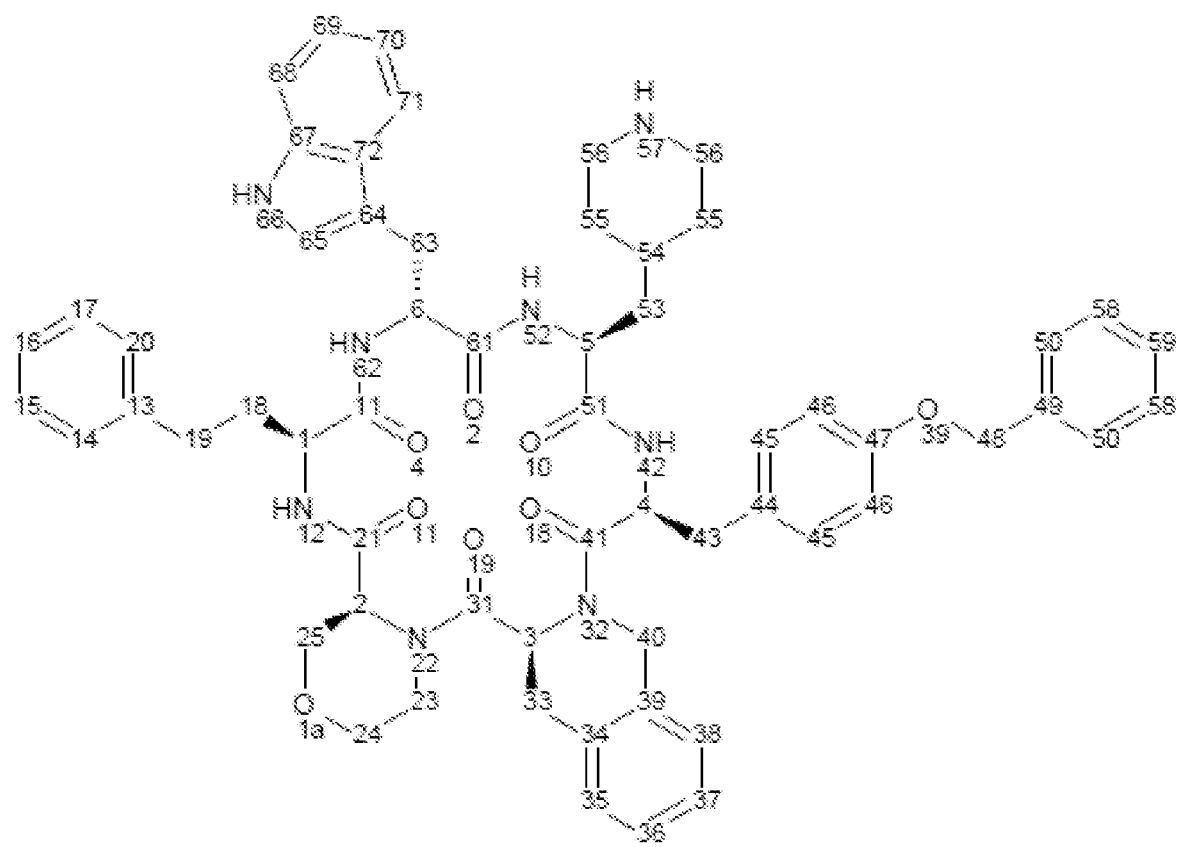
Figure 11:
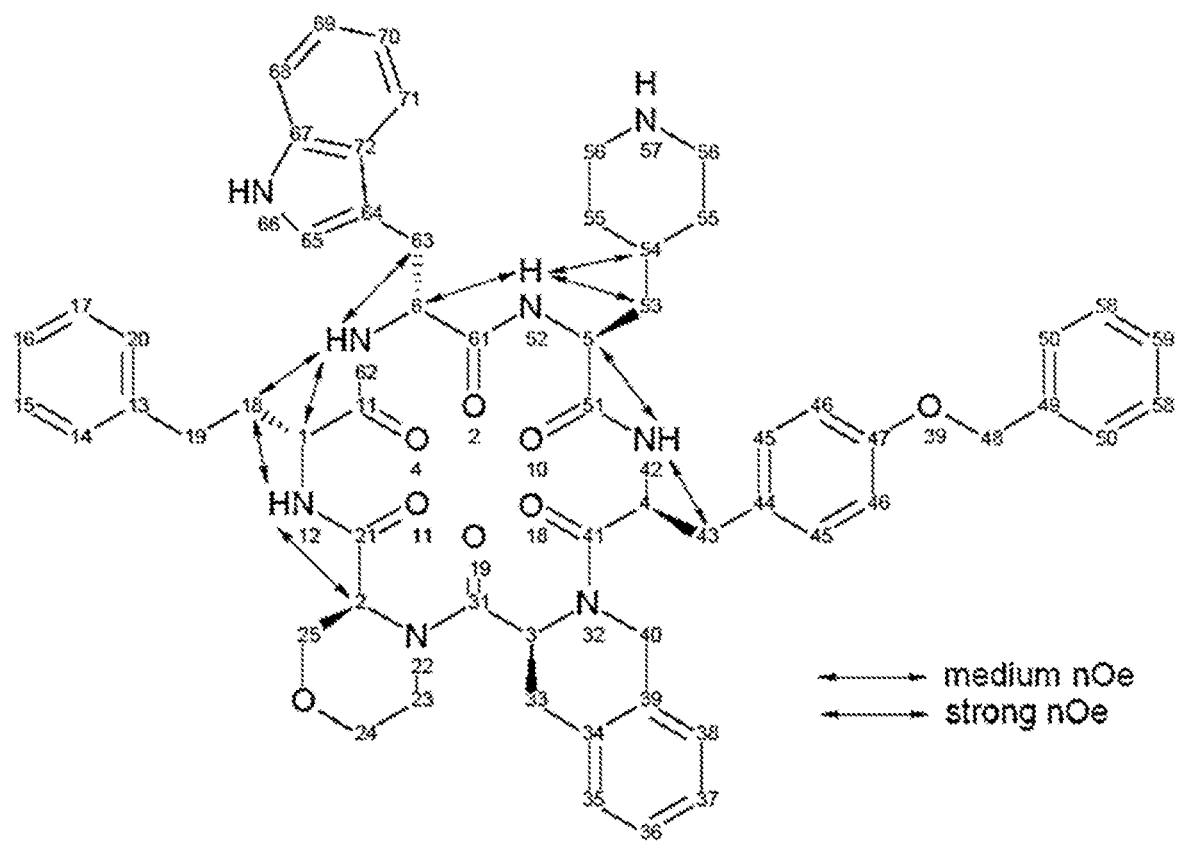

| Example | Structure | ¹H NMR | ¹³C NMR |
|---|---|---|---|
| | | 58, 58), 7.41 (d, J = 8.2 Hz, 2 H, 45, 45), 7.41 (d, J = 2.4 Hz, 1 H, 65), 7.45 (d, J = 7.3 Hz, 2 H, 50, 50), 7.67 (d, J = 8.2 Hz, 1 H, 68), 7.72 (d, J = 7.9 Hz, 1 H, 71), 8.12 (d, J = 8.5 Hz, 1 H, 42), 9.18 (d, J = 6.4 Hz, 1 H, 12), 9.95 (d, J = 7.0 Hz, 1 H, 52), 10.02 (d, J = 7.0 Hz, 1 H, 62), 11.96 (d, J = 1.2 Hz, 1 H, 66) ppm | (39), 137.5 (67), 137.7 (49), 142.1 (13), 158.1 (47), 168.1 (21), 170.5 (31), 170.7 (51), 170.9 (41), 171.2 (11), 173.8 (61) ppm |
| 45 | FIG. 10 | ¹H NMR (600 MHz, Pyr): δ = 1.12 (br. s., 1 H, 54<AX>), 1.23-1.42 (m, 3 H, 53<">, 55<AX>, 55<AX>), 1.51 (d, J = 14.3 Hz, 1 H, 55<EQ>), 1.80 (d, J = 13.6 Hz, 1 H, 55<EQ>), 1.93 (ddd, J = 14.0, 10.1, 3.9 Hz, 1 H, 53<'>), 2.56-2.66 (m, 2 H, 18<">, 18<'>), 2.89-3.01 (m, 4 H, 19<">, 19<'>, 56<AX>, 56<AX>), 3.00-3.06 (m, J = 13.9, 7.5 Hz, 1 H, 43<'>), 3.13-3.19 (m, J =15.0, 10.8 Hz, 1 H, 33<">), 3.23 (td, J = 13.0, 3.3 Hz, 1 H, 23<">), 3.26 (dd, J = 15.0, 5.7 Hz, 1 H, 33<'>), 3.39-3.46 (m, 4 H, 43<'>, 56<EQ>, 56<EQ>, 24<">), 3.48 (dd, J = 13.8, 5.3 Hz, 1 H, 63<">), 3.67 (dd, J = 11.2, 3.1 Hz, 1 H, 25<">), 3.79 (dd, J = 13.8, 11.4 Hz, 1 H, 63<'>), 3.84 (dd, J = 11.3, 3.4 Hz, 1 H, 24<'>), 4.46-4.52 (m, 2 H, 40<">, 3), 4.77-4.84 (m, 3 H, 23<'>, 5, 2), 4.90 (d, J = 14.9 Hz, 1 H, 40<'>), 4.98 (s, 2 H, 48<">, 48<'>), 5.11 (d, J = 10.8 Hz, 1 H, 25<'>), 5.42 (q, J = 6.5 Hz, 1 H, 1), 5.55 (ddd, J = 11.4, 7.0, 5.3 Hz, 1 H, 6), 5.80 (ddd, J = 8.3, 6.4 Hz, 1 H, 4), 6.94 (d, J = 8.4 Hz, 2 H, 46, 46), 7.01 (t, J = 7.4 Hz, 1 H, 70), 7.08 (d, J = 7.0 Hz, 1 H, 38), 7.15-7.20 (m, 1 H, 16), 7.20-7.21 (m, 1 H, 37), 7.24-7.26 (m, 4 H, 17, 15, 20, 14), 7.26-7.28 (m, 3 H, 69, 59, 36), 7.29 (d, J = 5.3 Hz, 1 H, 35), 7.33 (t, J = 7.6 Hz, 2 H, 58, 58), 7.37 (d, J = 8.4 Hz, 2 H, 45, 45), 7.44 (d, J = 7.6 Hz, 2 H, 50, 50), 7.43 (s, 1 H, 65), 7.70 (d, J = 8.1 Hz, 1 H, 71), 7.81 (d, J = 8.1 Hz, 1 H, 68), 8.14 (d, J = 8.6 Hz, 1 H, 42), 9.18 (d, J = 6.2 Hz, 1 H, 12), 10.16 (d, J = 7.9 Hz, 1 H, 52), 10.29 (d, J = 7.2 Hz, 1 H, 62), 12.02 (d, J = 1.5 Hz, 1 H, 66) ppm | ¹³C NMR (151 MHz, Pyr): δ = 28.2 (55), 28.6 (63), 29.7 (55), 30.3 (54), 31.4 (33), 32.6 (19), 36.4 (18), 38.5 (53), 39.6 (43), 40.3 (23), 43.3 (56), 43.4 (56), 46.7 (40), 50.9 (4), 51.3 (5), 53.1 (3), 55.2 (1), 55.5 (6), 57.9 (2), 66.8 (24), 67.8 (25), 70.0 (48), 110.5 (64), 112.3 (68), 115.0 (46, 46), 119.3 (71), 119.5 (70), 122.0 (69), 124.7 (65), 126.3 (16, 38), 127.4 (37), 127.6 (35), 127.9 (50, 50), 128.1 (72), 128.2 (36), 128.3 (59), 128.8 (58, 58), 128.8 (17, 15), 128.9 (14, 20), 129.5 (44), 131.5 (45, 45), 134.7 (34), 135.0 (39), 137.5 (67), 137.7 (49), 142.1 (13), 158.1 (47), 168.0 (21), 170.6 (41), 170.9 (31), 171.3 (11), 171.5 (51), 173.4 (61) ppm |
| 62 | FIG. 11 | ¹H NMR (600 MHz, Pyr): δ = 0.98 (br. s., 1 H, 54<AX>), 1.15 (br. s., 1 H, 54<AX>), 1.28 (br. s., 5 H, 55<AX>, 53<">), 1.43 (br. s., 3 H, 55<EQ>, 53<">), 1.74 (d, J = 11.9 Hz, 1 H, 55<EQ>), 1.86 (ddd, J = 13.8, 9.4, 4.4 Hz, 1 H, 53<'>), 1.93 (d, J = 13.2 Hz, 1 H, 55<EQ>), 2.09 (br. s., 1 H, 53<'>), 2.50-2.65 (m, 1 H, 18<">), 2.75 (br. s., 3 H, 18<">, 18<'>, 19<'">), 2.86 (br. s., 1 H, 18<">), 2.87-3.01 (m, 5 H, 56<AX>, 56<AX>, 19<'>), 3.19-3.30 (m, 5 H, 43<">, 19<">, 33<">, 33<'>), 3.32-3.44 (m, 8 H, 33<'>,56<EQ>, 63<">, 24<">), 3.43-3.46 (m, 1 H, 19<'>), 3.49 (dd, J = 14.3, 5.5 Hz, 2 H, 43<'>, 43<'>), 3.52-3.59 (m, J = 2.8 Hz, 1 H, 24<">), 3.61-3.69 (m, J = 13.2, 11.6 Hz, 2 H, 43<'>, 63<'>), 3.72 (td, J = 12.8, 3.7 Hz, 2 H, 25<">, 23<">), 3.79 (t, J = 12.5 Hz, 1 H, 63<'>), 3.88 (dd, J = 11.3, 2.5 Hz, 2 H, 25<">, 24<'>), 3.91-3.95 (m, 2 H, 23<">, 23<'>), 3.97 (dd, J = 11.1, 3.0 Hz, 1 H, 24<'>), 4.69-4.81 (m, 4 H, 23<'>, 3, 5, 40<">), 4.91-4.99 (m, 1 H, 40<">), 5.00 (d, J = 3.9 Hz, 4 H, 48), 5.01-5.04 (m, 1 H, 5), 5.05-5.11 (m, 2 H, 40<'>), 5.12 (d, 1 H, 25<'>), 5.17-5.23 (m, 2 H, 25<'>, 1), 5.31-5.35 (m, 1 H, 6), 5.40 (br. s., 1 H, 2), 5.45 (ddd, J = 11.3, 7.0, 4.4 Hz, 1 H, 6), 5.50 (t, J = 7.2 Hz, 1 H, 3), 5.55 (d, J = 3.9 Hz, 1 H, 2), 5.69 (br. s., 1 H, 1), 5.75 (td, J = 8.1, 6.1 Hz, 1 H, 4), 5.99 (t, J = 10.3 Hz, 1 H, 4), 6.88 (d, J = 8.4 Hz, 2 H, 46, 46), 7.00 (t, J = 7.4 Hz, 1 H, 70), 7.01 (d, J = 8.4 Hz, 2 H, 46, 46), 7.05 (t, J = 7.3 Hz, 1 H, 70), 7.05-7.08 (m, 2 H, 16), 7.07-7.11 (m, 2 H, 17, 15), 7.13 (t, 5 H, 35, 38, 20, 14), 7.20 (d, 3 H, 37, 35, 36), 7.23 (br. s., 3 H, 15, 17, 69), 7.24-7.28 (m, 2 H, 37, 69), 7.30 (d, J = 7.2 Hz, 3 H, 36, 59), 7.35 (t, J = 7.7 Hz, 2 H, 58, 58), 7.38 (s, 2 H, 65), 7.40 (t, J = 7.5 Hz, 2 H, 58, 58), 7.46 (d, J = 6.6 Hz, 4 H, 50, 50), 7.47 (d, J = 6.6 Hz, 2 H, 45, 45), 7.52 (d, J = 8.1 Hz, 2 H, 45, 45), 7.54-7.58 (m, 3 H, 20, 14, 68), 7.62 (d, J = 8.3 Hz, 1 H, 71), 7.73 (d, J = 8.1 Hz, 1 H, 68), 7.77 (d, J = 8.1 Hz, 1 H, 71), 8.20 (d, J = 8.1 Hz, 1 H, 42), 8.71 (d, J = | ¹³C NMR (151 MHz, Pyr): δ = 27.5 (63), 27.9 (63), 28.0 (55), 28.3 (55), 29.4 (55), 29.6 (55), 30.3 (54), 30.6 (54), 31.1 (19), 31.4 (33), 31.6 (19), 32.1 (33), 34.2 (18), 37.6 (18), 37.8 (43), 38.3 (53), 39.0 (43), 40.2 (23), 43.4 (56), 43.4 (56), 46.5 (40), 47.1 (40), 50.3 (5), 51.8 (3), 52.0 (5, 4), 52.7 (4), 53.6 (1), 54.7 (2, 1), 55.9 (6), 57.2 (6), 58.2 (2), 61.5 (3), 66.1 (24), 66.8 (25), 67.0 (24), 68.4 (25), 70.0 (48), 70.1 (48), 110.2 (64), 110.8 (64), 112.0 (68), 112.1 (68), 115.0 (46, 46), 119.0 (71), 119.4 (70), 119.5 (71), 119.5 (70), 121.9 (69), 124.6 (65), 125.9 (16), 126.1 (16), 126.3 (38), 126.4 (38), 127.1 (35), 37), 127.5 (37), 127.9 (35), 128.0 (36), 128.0 (50, 50), 128.1 (72), 128.2 (59), 128.6 (15, 17), 128.8 (36), 128.8 (58, 58), 128.9 (20, 14), 129.5 (20, 14), 129.9 (44), 130.1 (44), 130.9 (45, 45), 131.6 (45, 45), 133.6 (39), 134.3 (39, 34), 135.2 (34), 137.5 |

TABLE 3-continued

¹H NMR and ¹³C NMR analysis for selected Examples

| Example | Structure | ¹H NMR | ¹³C NMR |
|---|---|---|---|
| | | 9.2 Hz, 1 H, 12), 8.93 (d, J = 7.0 Hz, 1 H, 62), 9.00 (d, J = 9.7 Hz, 1 H, 42), 9.06 (d, J = 9.2 Hz, 1 H, 52), 9.62 (d, J = 7.9 Hz, 2 H, 62, 12), 9.95 (d, J = 7.9 Hz, 1 H, 52), 11.81 (br. s., 1 H, 66), 11.89 (br. s., 1 H, 66) ppm | (67), 137.8 (49), 137.8 (49), 142.4 (13), 143.1 (13), 158.0 (47), 158.1 (47), 168.3 (21), 168.8 (21), 170.9 (31), 171.3 (31), 171.4 (51), 171.5 (41), 171.6 (11), 171.8 (11), 171.9 (51), 172.4 (41), 173.2 (61), 173.4 (61) ppm |

Biological Activity

A Hit Hunter® cAMP XS+ assay was used to monitor activation of the $SST_2$ and $SST_5$ via the Gi G protein. Cells were pre-stimulated with forskolin to elicit a cAMP response and the potency and efficacy of somatostatin agonists to reduce cAMP was measured. Briefly cells (10,000 cells/well) were incubated (37° C.; 30 min) with compound (10 μM-10 μM) in media (2:1 HBSS/11 mM Hepes: cAMP XS+Ab reagent) in the presence of $EC_{80}$ forskolin (20 M $SST_2$ and 15 μM $SST_5$). Signal was detected through incubation with 20 μL cAMP XS+ED/CL lysis cocktail (60 mm; RT) followed by incubation with 20 NL cAMP XS+EA reagent (180 min; RT). Microplates were read with a PerkinElmer Envision™ instrument for chemiluminescent signal detection.

Compound activity was normalised to the activity of somatostatin 28 (basal 0%, 100% 6 signal achieved with 50 nM somatostatin 28) and data analyzed using Dotmatics Browser using a 4-parameter logistic fit to determine potency ($pEC_{50}$) and efficacy (%).

| Example Number | $SST_2$ $pEC_{50}$ | $SST_2$ (EMax) | $SST_5$ $pEC_{50}$ | $SST_5$ (EMax) | $SST_{5/2}$ Selectivity |
|---|---|---|---|---|---|
| Somatostatin-28 | 9.6 | 100.4 | 10.3 | 101.0 | 4.6 |
| Pasireotide | 9.0 | 100.3 | 9.6 | 101.5 | 3.8 |
| Octreotide | 10.5 | 98.5 | 7.8 | 97.0 | 0.0 |
| Example 1 | 5.5 | 62.0 | 7.6 | 98.6 | 130.7 |
| Example 2 | 6.4 | 96.4 | 7.7 | 104.8 | 21.9 |
| Example 3 | 6.7 | 98.4 | 9.1 | 100.0 | 236.7 |
| Example 4 | 6.6 | 102.9 | 7.9 | 105.0 | 23.6 |
| Example 5 | 6.5 | 97.6 | 8.0 | 98.7 | 33.8 |
| Example 6 | 7.3 | 97.9 | 8.9 | 97.9 | 41.9 |
| Example 7 | 8.0 | 99.2 | 9.3 | 101.5 | 19.3 |
| Example 8 | 7.5 | 101.2 | 8.9 | 102.0 | 22.7 |
| Example 9 | 7.3 | 101.5 | 8.6 | 106.0 | 23.3 |
| Example 10 | 7.7 | 100.8 | 9.3 | 98.0 | 38.9 |
| Example 11 | 6.7 | 98.0 | 8.4 | 99.4 | 48.2 |
| Example 12 | 7.7 | 97.6 | 9.1 | 98.1 | 26.1 |
| Example 13 | 6.7 | 97.6 | 8.6 | 98.7 | 87.2 |
| Example 14 | 6.8 | 99.6 | 10.1 | 96.7 | 1876.8 |
| Example 15 | <5.0 | 55.5 | 7.7 | 100.7 | 531.3 |
| Example 16 | <5.0 | 79.5 | 8.4 | 100.5 | 2729.5 |
| Example 17 | 6.4 | 97.3 | 9.3 | 103.8 | 789.4 |
| Example 18 | 8.3 | 28.2 | 7.9 | 100.1 | 0.3 |
| Example 19 | 7.0 | 75.5 | 7.7 | 99.8 | 5.5 |
| Example 20 | 5.5 | 98.0 | 8.2 | 99.6 | 418.4 |
| Example 21 | 6.4 | 97.3 | 8.7 | 101.1 | 220.3 |
| Example 22 | 7.1 | 100.4 | 9.3 | 101.7 | 142.6 |
| Example 23 | 6.2 | 96.6 | 8.4 | 100.7 | 148.7 |
| Example 24 | <5 | 46.8 | 7.0 | 101.7 | 110.6 |
| Example 25 | 6.7 | 100.3 | 9.9 | 102.4 | 1351.8 |
| Example 26 | 6.3 | 66.6 | 9.9 | 99.1 | 4067.3 |
| Example 27 | 6.4 | 90.7 | 8.6 | 99.4 | 159.6 |
| Example 28 | 8.1 | 99.6 | 10.1 | 100.4 | 101.0 |
| Example 29 | 6.1 | 89.6 | 9.0 | 100.0 | 663.6 |
| Example 30 | 6.6 | 100.1 | 9.0 | 101.4 | 214.2 |
| Example 31 | 6.7 | 99.7 | 10.2 | 88.7 | 3441.5 |
| Example 32 | 7.0 | 98.8 | 8.9 | 99.9 | 66.8 |
| Example 33 | <5.0 | 13.4 | 7.4 | 107.2 | 279.1 |
| Example 34 | 5.4 | 49.2 | 9.0 | 101.9 | 3271.8 |
| Example 35 | <5.0 | 27.8 | 9.0 | 107.2 | 10046.0 |
| Example 36 | 6.3 | 63.4 | 8.9 | 101.9 | 384.3 |
| Example 37 | 5.2 | 75.8 | 8.7 | 107.5 | 2927.5 |
| Example 38 | 5.6 | 82.7 | 7.9 | 103.1 | 171.5 |
| Example 39 | 6.4 | 100.3 | 9.4 | 106.6 | 1104.6 |
| Example 40 | 6.5 | 91.2 | 8.6 | 105.7 | 126.6 |
| Example 41 | 8.1 | 102.3 | 9.8 | 104.0 | 51.0 |
| Example 42 | 7.9 | 99.3 | 9.6 | 104.0 | 45.1 |

-continued

| Example Number | SST$_2$ pEC$_{50}$ | SST$_2$ (EMax) | SST$_5$ pEC$_{50}$ | SST$_5$ (EMax) | SST$_{5/2}$ Selectivity |
|---|---|---|---|---|---|
| Example 43 | 7.5 | 101.3 | 9.5 | 106.7 | 94.3 |
| Example 44 | 6.1 | 75.3 | 9.0 | 105.1 | 823.8 |
| Example 45 | 6.8 | 100.5 | 9.4 | 100.1 | 430.7 |
| Example 46 | 7.4 | 98.6 | 10.1 | 101.5 | 527.6 |
| Example 47 | 6.7 | 100.1 | 9.1 | 108.0 | 226.4 |
| Example 48 | 8.7 | 100.3 | 10.7 | 102.8 | 106.6 |
| Example 49 | 6.3 | 98.9 | 8.5 | 103.3 | 143.3 |
| Example 50 | 6.2 | 95.4 | 7.8 | 103.3 | 41.1 |
| Example 51 | 8.3 | 100.3 | 10.1 | 106.4 | 64.3 |
| Example 52 | 6.4 | 96.8 | 9.8 | 107.4 | 2108.2 |
| Example 53 | <5.0 | 50.9 | 7.5 | 102.7 | 293.1 |
| Example 54 | 6.2 | 96.2 | 9.3 | 104.0 | 1083.5 |
| Example 55 | <5 | 85.9 | 8.0 | 106.4 | 1120.0 |
| Example 56 | 6.5 | 98.1 | 9.7 | 104.3 | 1648.2 |
| Example 57 | 6.7 | 96.5 | 9.3 | 102.1 | 404.6 |
| Example 58 | <5.0 | 42.9 | 7.8 | 103.0 | 695.7 |
| Example 59 | 6.3 | 95.7 | 9.2 | 106.2 | 738.9 |
| Example 60 | 6.9 | 99.8 | 9.0 | 104.3 | 129.4 |
| Example 61 | <5.0 | 23.4 | 7.5 | 103.3 | 291.4 |
| Example 62 | 6.2 | 99.4 | 8.5 | 101.8 | 224.3 |
| Example 63 | 7.2 | 102.4 | 8.6 | 103.8 | 24.4 |
| Example 64 | 7.0 | 100.3 | 7.8 | 103.8 | 5.5 |
| Example 65 | 6.0 | 91.8 | 9.4 | 99.4 | 2293.7 |
| Example 66 | <5.0 | 51.1 | 8.9 | 102.7 | 7454.5 |
| Example 67 | 6.4 | 98.3 | 7.8 | 103.7 | 25.7 |
| Example 68 | 6.6 | 99.1 | 9.5 | 98.8 | 791.6 |
| Example 69 | <5.0 | 69.0 | 7.1 | 102.7 | 124.3 |
| Example 70 | <5.0 | 77.9 | 8.3 | 102.2 | 1815.8 |
| Example 71 | <5.0 | 52.8 | 7.2 | 103.2 | 171.4 |
| Example 72 | <5.0 | 14.0 | 8.2 | 101.3 | 1621.3 |
| Example 73 | 6.4 | 99.2 | 9.2 | 94.9 | 566.7 |
| Example 77 | 5.4 | 39.3 | 8.2 | 103.6 | 681.8 |
| Example 78 | 5.5 | 76.2 | 8.9 | 105.5 | 2726.7 |

The invention claimed is:

1. A compound of the formula (1):

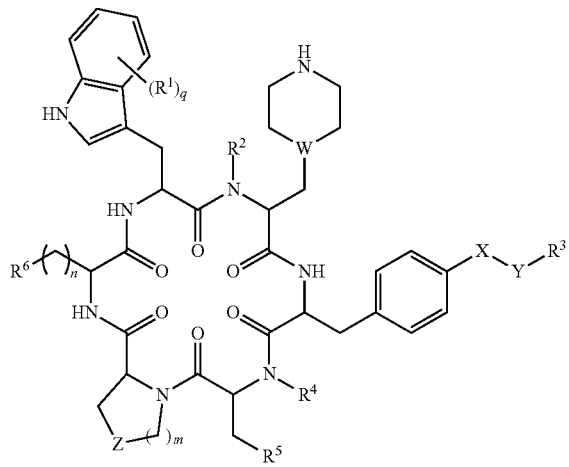

or a salt thereof, wherein;

W is CH or N;

X and Y are CH$_2$ or O, wherein one of X and Y is CH$_2$ and the other of X and Y is O;

Z is CHR$^7$, NR$^8$ or O;

m is 1 or 2;

n is 0 to 3;

each R$^1$ is independently selected from halo, C$_1$-C$_3$ alkyl and C$_1$-C$_3$ alkoxy, wherein the C$_1$-C$_3$ alkyl and alkoxy groups are optionally substituted with up to 6 fluorine atoms;

q is 0 to 2;

R$^2$ is selected from H and C$_1$-C$_3$ alkyl optionally substituted with up to 6 fluorine atoms;

R$^3$ is selected from optionally substituted C$_1$-C$_6$ alkyl, optionally substituted C$_3$-C$_6$ cycloalkyl, optionally substituted aryl and optionally substituted heteroaryl;

R$^4$ is H or optionally substituted C$_1$-C$_3$ alkyl, where the C$_1$-C$_3$ alkyl group is optionally joined to R$^5$ to form a ring;

R$^5$ is selected from optionally substituted C$_1$-C$_6$ alkyl, optionally substituted aryl and optionally substituted heteroaryl, where R$^5$ is optionally joined to R$^4$ to form a ring;

R$^6$ is selected from optionally substituted aryl, optionally substituted heteroaryl, optionally substituted O-aryl or optionally substituted O-heteroaryl;

R$^7$ is selected from H, optionally substituted C$_1$-C$_6$ alkyl, CONR$^{10}$R$^{11}$, OCONR$^{10}$R$^{11}$, OCOR$^{10}$, OCOOR$^{10}$, COOR$^{10}$ or OR$^{12}$;

R$^8$ is selected from H, CONR$^{10}$R$^{11}$ or COOR$^{10}$;

R$^{10}$ and R$^{11}$ are independently selected from H, optionally substituted C$_1$-C$_6$ alkyl and optionally substituted C$_2$-C$_6$ alkyl where any one atom in the C$_2$-C$_6$ alkyl group is replaced by a heteroatom selected from N, O and S, or wherein R$^{10}$ and R$^{11}$ are optionally joined to form a ring; and R$^{12}$ is optionally substituted aryl or optionally substituted heteroaryl.

2. The compound according to claim 1 which is a compound of formula (1a):

(1a)

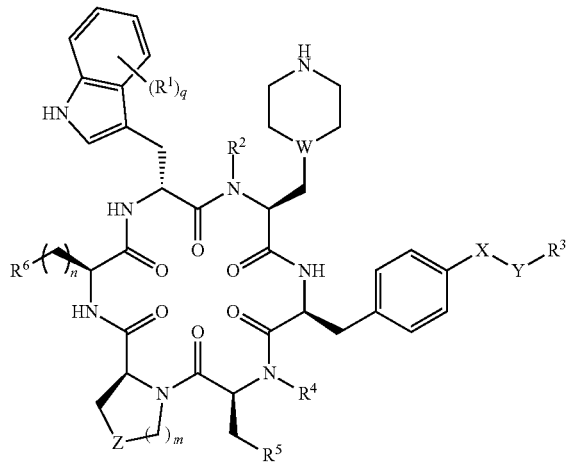

or a salt thereof.

3. The compound according to claim 1 which is a compound of formula (1b):

(1b)

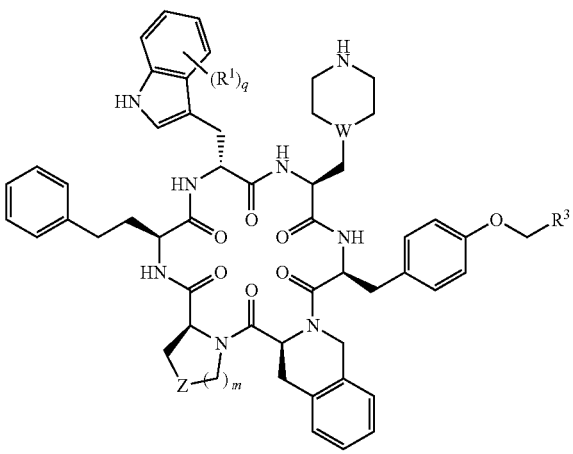

or a salt thereof.

4. The compound according to claim 1, wherein X is O and Y is $CH_2$.

5. The compound according to claim 1, wherein Z is $CHR^7$.

6. The compound according to claim 1, wherein $R^1$ is OMe or Me.

7. The compound according to claim 1, wherein $R^2$ is H.

8. The compound according to claim 1, wherein $R^3$ is optionally substituted phenyl, optionally substituted cyclohexyl, optionally substituted cyclopentyl or optionally substituted cyclobutyl, wherein the optional substituents are selected from chloro, bromo and fluoro.

9. The compound according to claim 1, wherein $R^4$ is H.

10. The compound according to claim 1, wherein $R^5$ is optionally substituted phenyl or optionally substituted pyridyl, wherein the optional substituents are selected from chloro, bromo, fluoro and OMe.

11. The compound according to claim 1, wherein $R^4$ and $R^5$ are joined together to form a ring; and wherein the ring moiety formed by $R^4$ and $R^5$ is selected from the group consisting of:

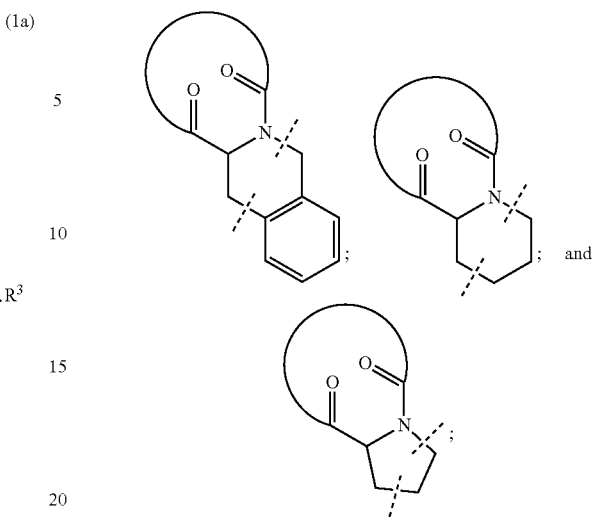

wherein said ring moieties are optionally substituted with a group or groups selected from halo, $C_1$-$C_3$ alkyl and $C_1$-$C_3$ alkoxy, wherein the $C_1$-$C_3$ alkyl and alkoxy groups are themselves optionally substituted with up to 6 fluorine atoms.

12. The compound according to claim 1, wherein $R^7$ is $OCONR^{10}R^{11}$, $COOR^{10}$ or $OR^{12}$; wherein $R^{10}$ and $R^{11}$ are $C_2$-$C_6$ alkyl where any one atom in the $C_2$-$C_6$ alkyl group is replaced by a heteroatom selected from N, O and S, where $R^{10}$ and $R^{11}$ are optionally joined via $CH_2$ to form a ring; and $R^{12}$ is pyridyl.

13. The compound according to claim 1, wherein the moiety formed by Z and m is selected from:

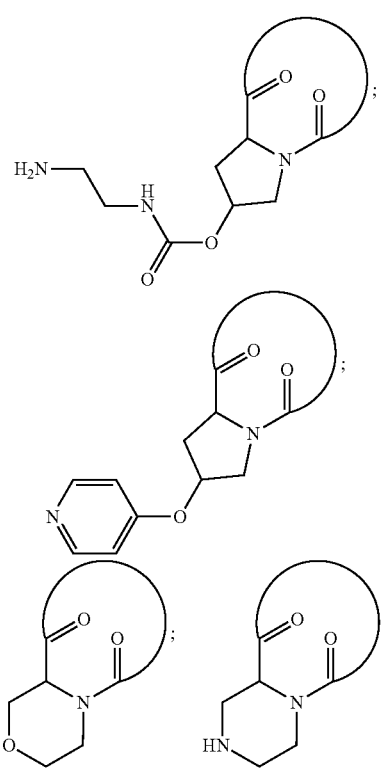

127
-continued
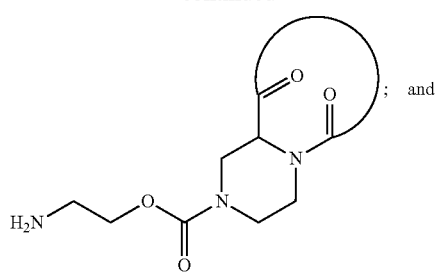
; and
128
-continued
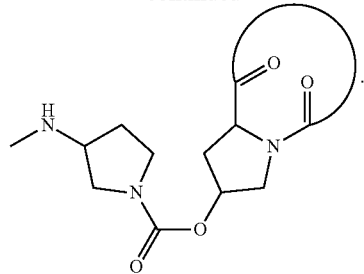
.
14. The compound according to claim 1 wherein $R^6$ is phenyl.
15. The compound according to claim 1 which is selected from the group consisting of:
Example 1
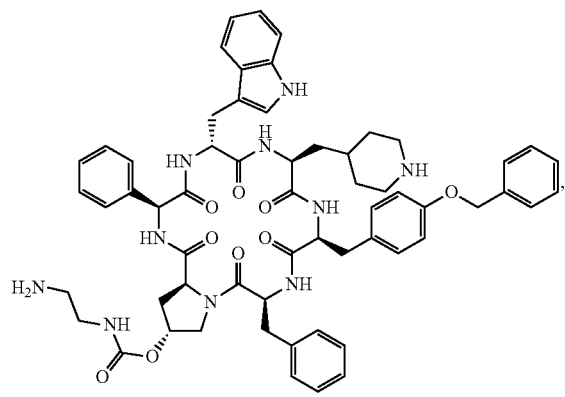
,
Example 2
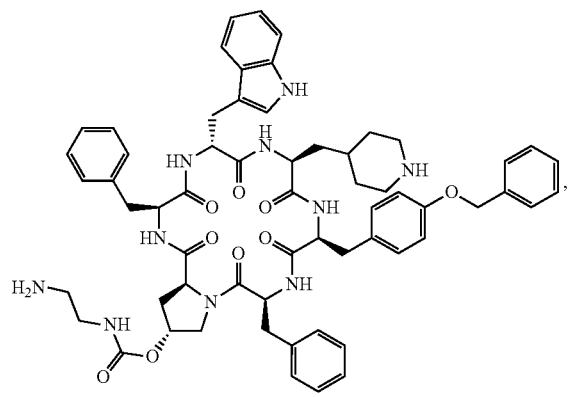
,
Example 3
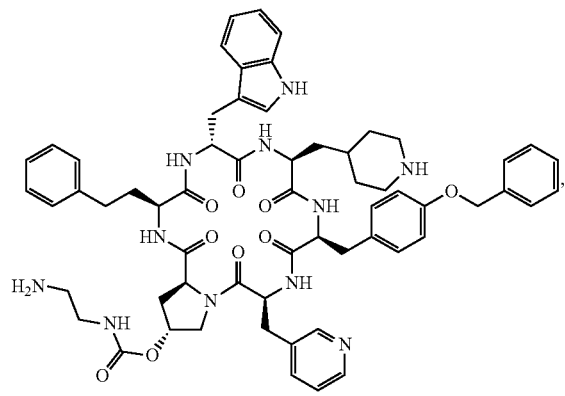
,
Example 4
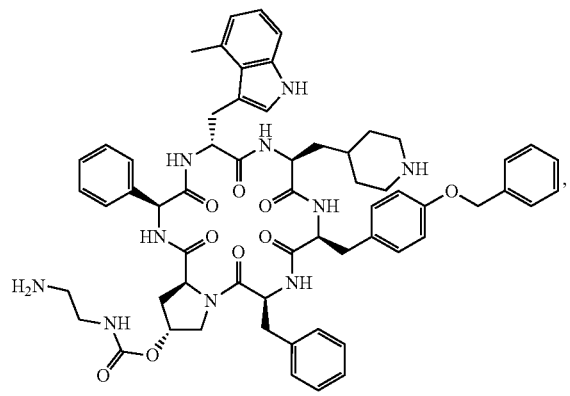
, Example 5
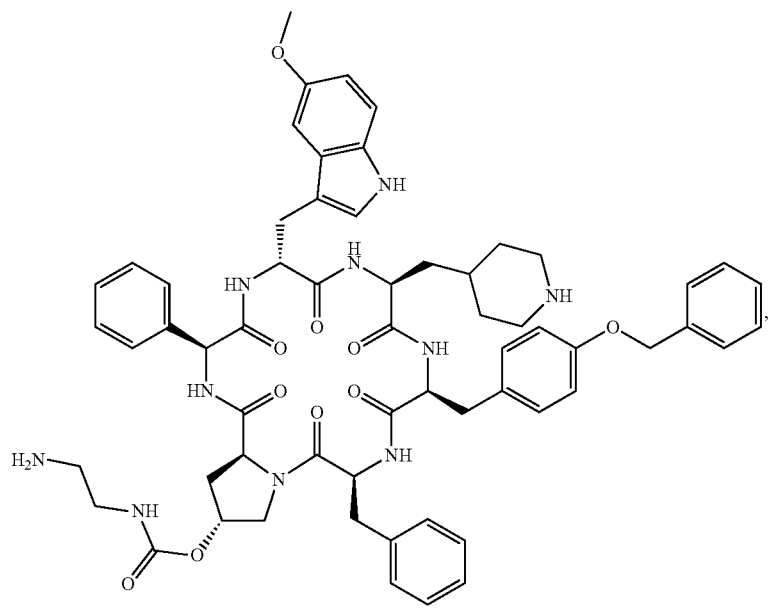
Example 6
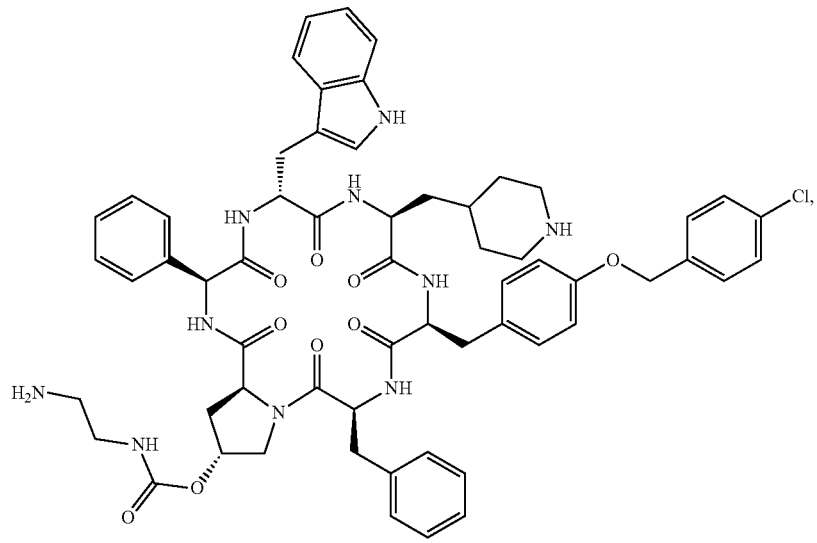
Example 7
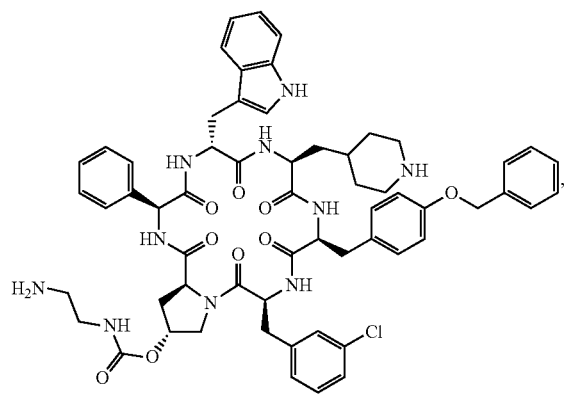
Example 8
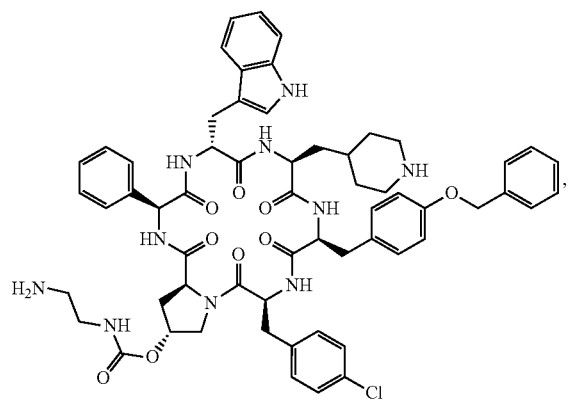

-continued
Example 9
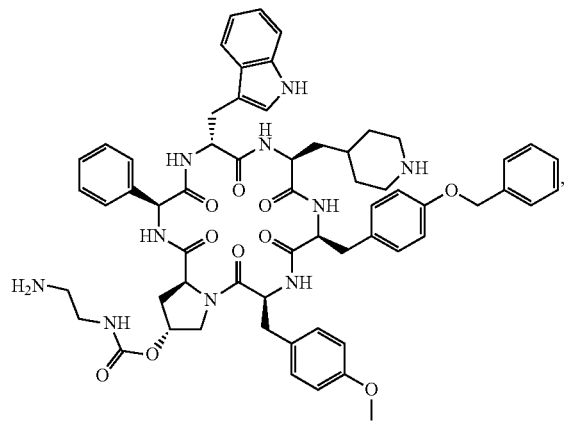
Example 10
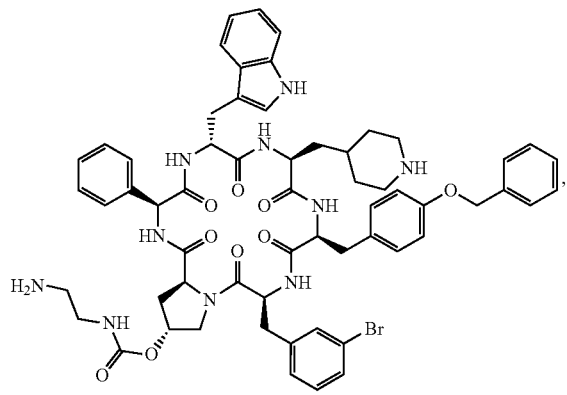
Example 11
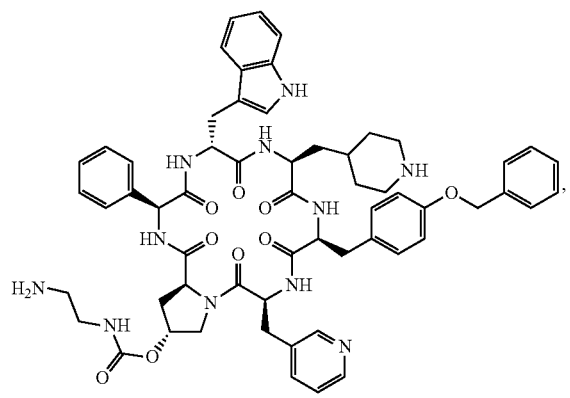
Example 12
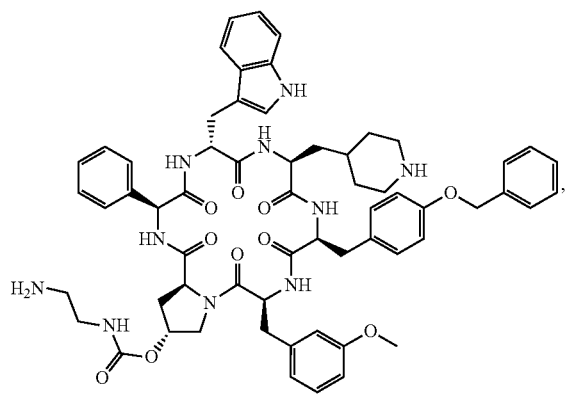
Example 13
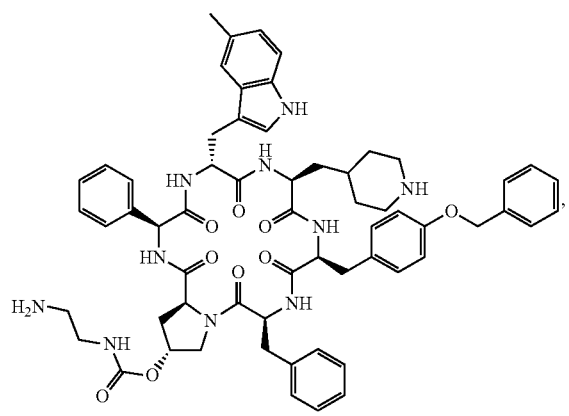
Example 14
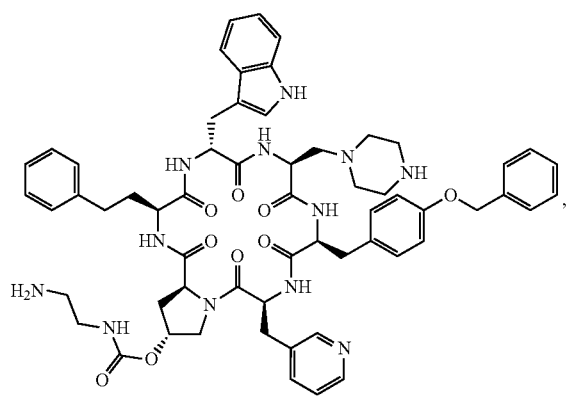

-continued
Example 15
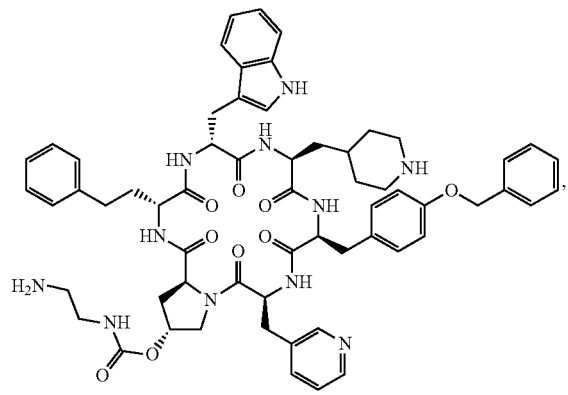
Example 16
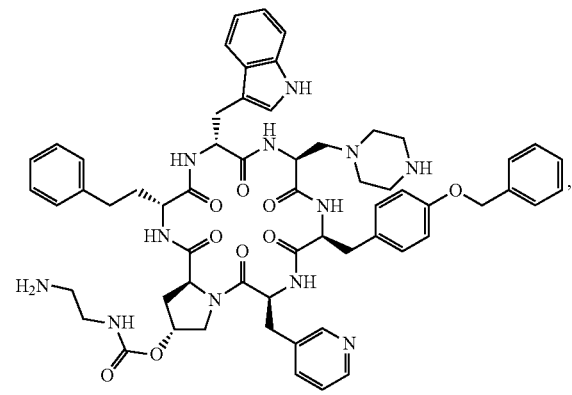
Example 17
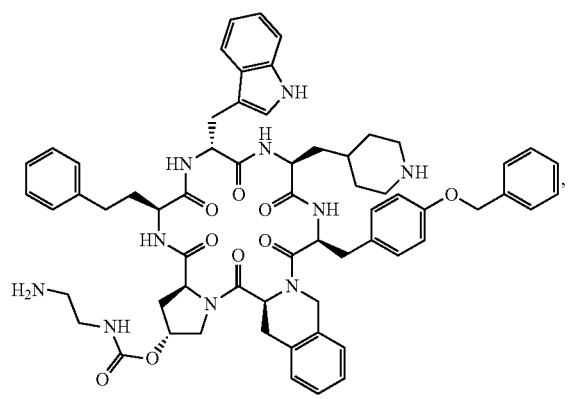
Example 18
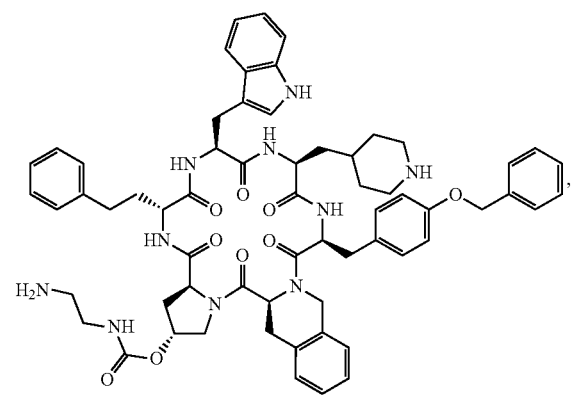
Example 19
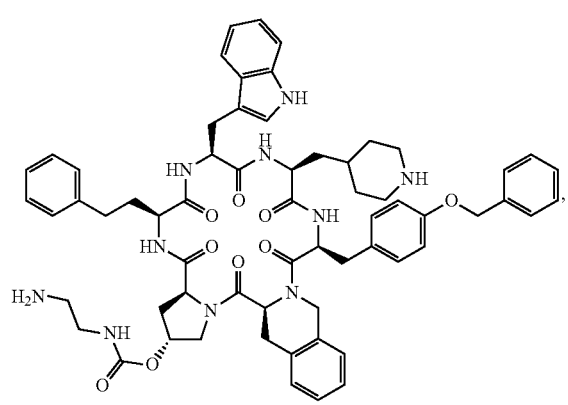
Example 20
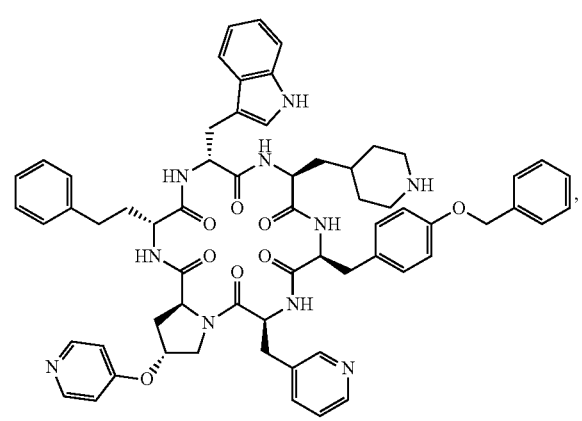

-continued
Example 21
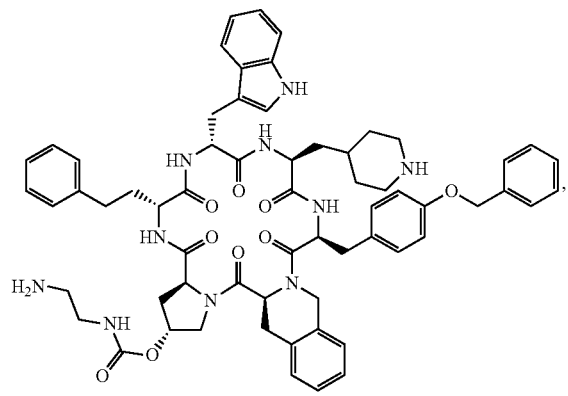
Example 22
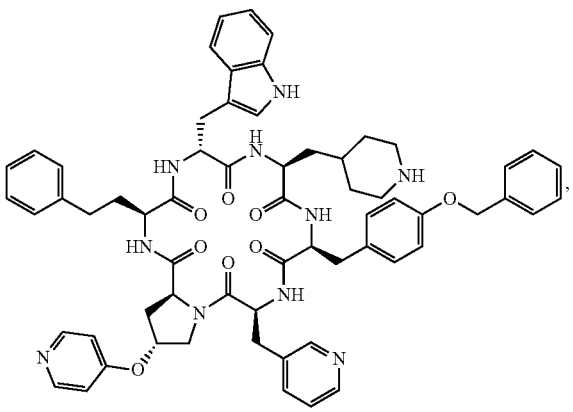
Example 23
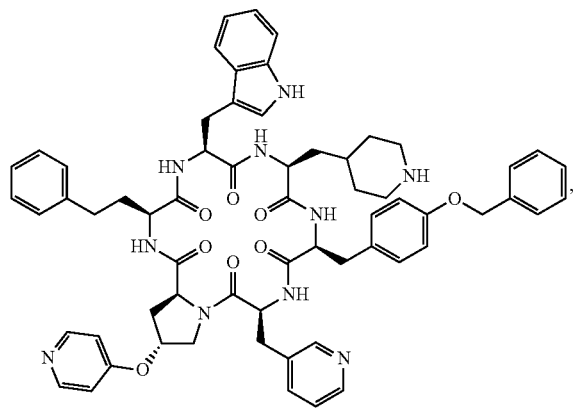
Example 24
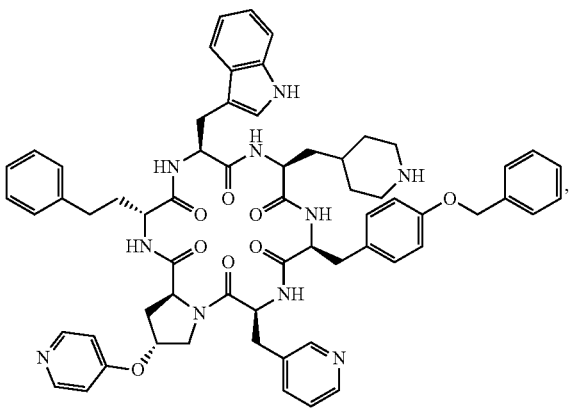
Example 25
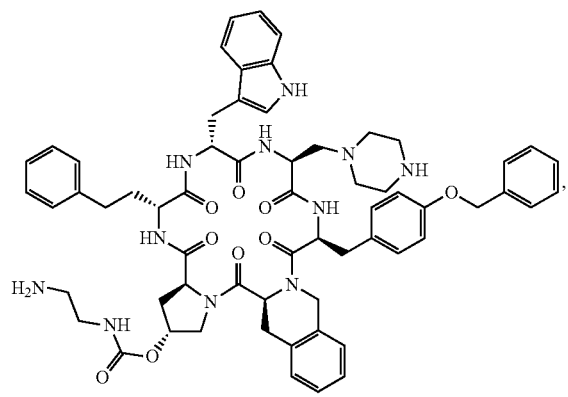
Example 26
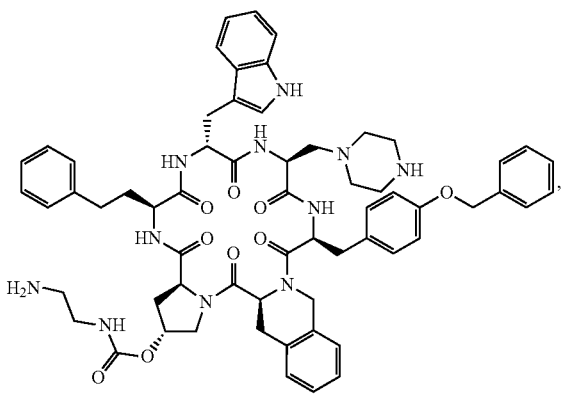

-continued
Example 27
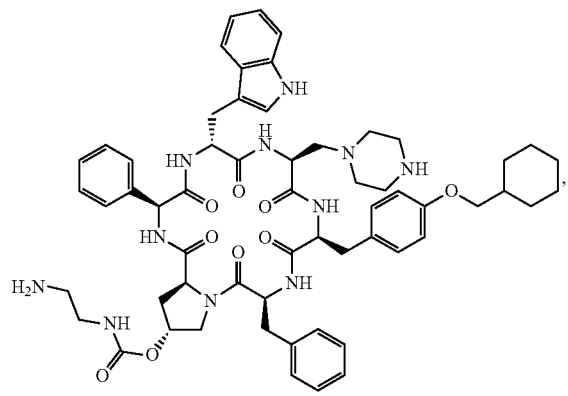
Example 28
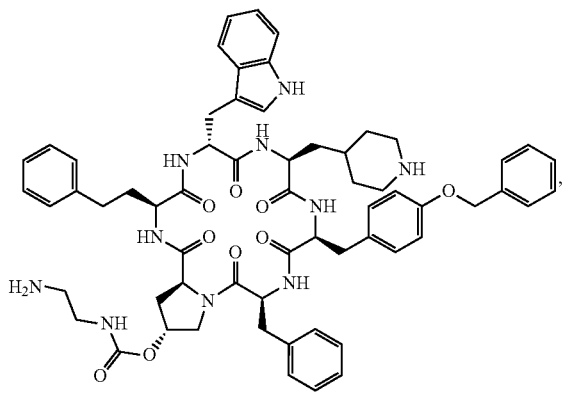
Example 29
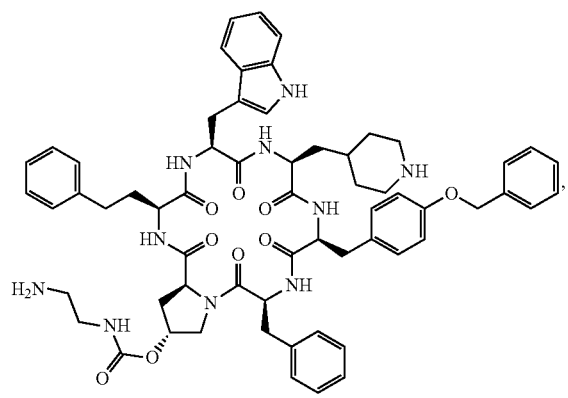
Example 30
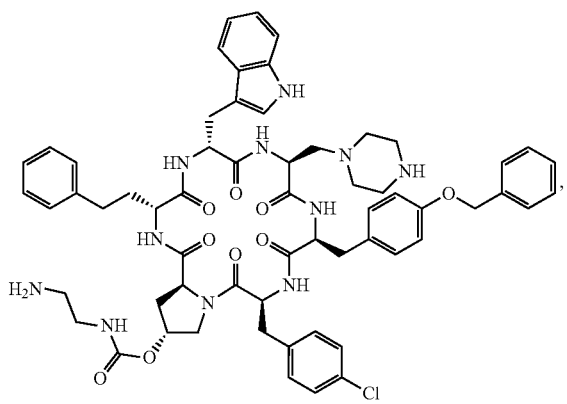
Example 31
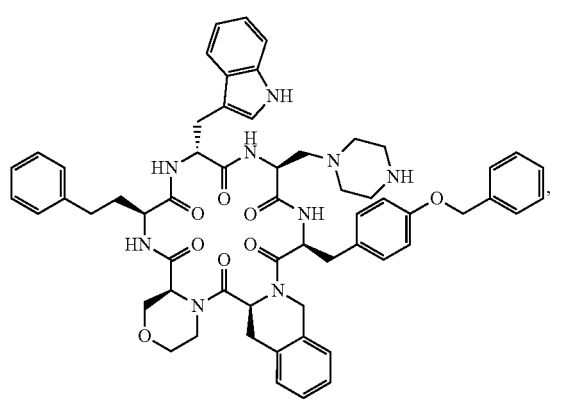
Example 32
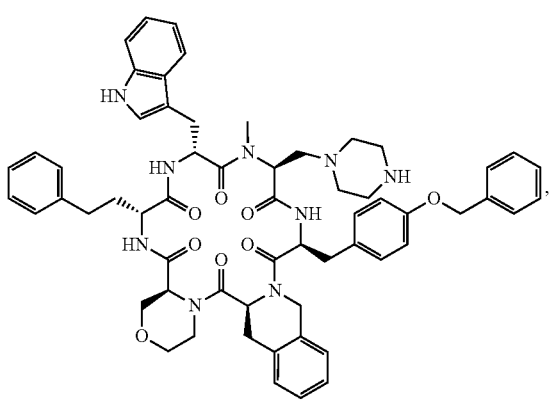
Example 33
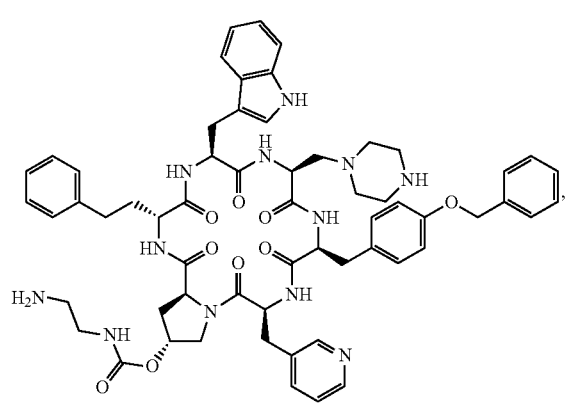
Example 34
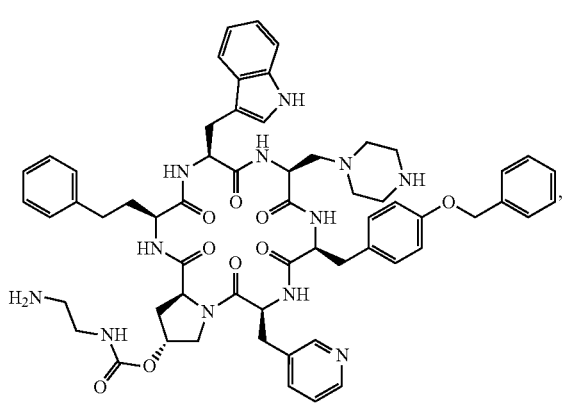

-continued
Example 35
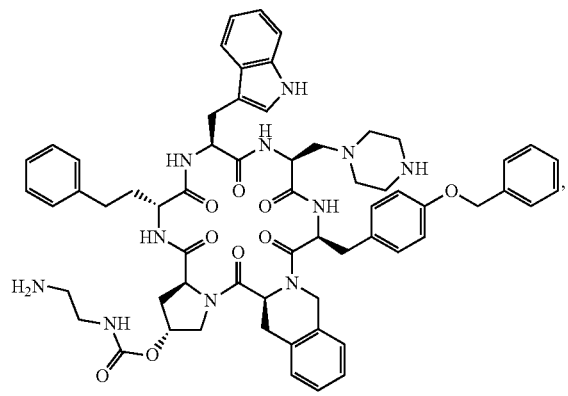,
Example 36
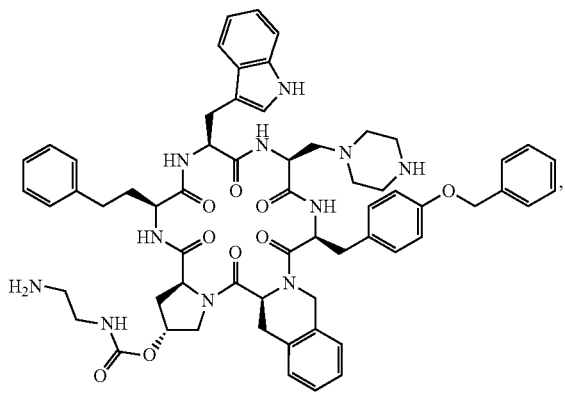,
Example 37
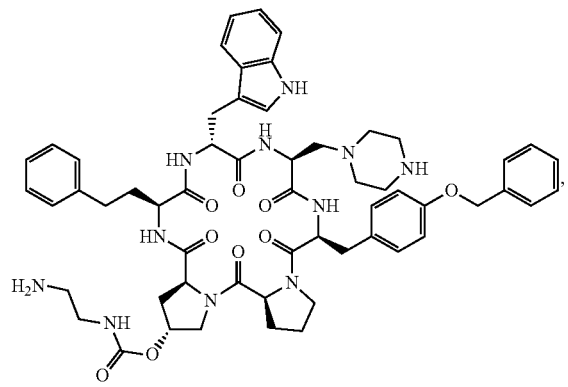,
Example 38
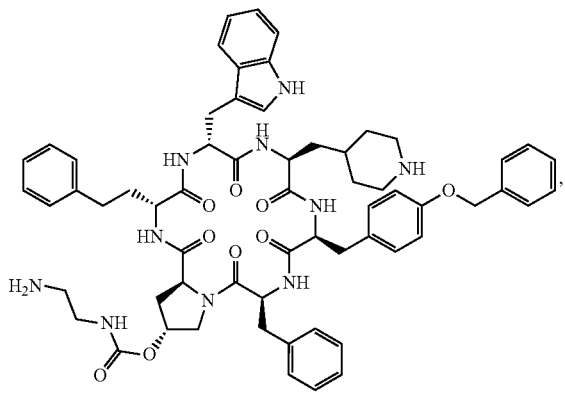,
Example 39
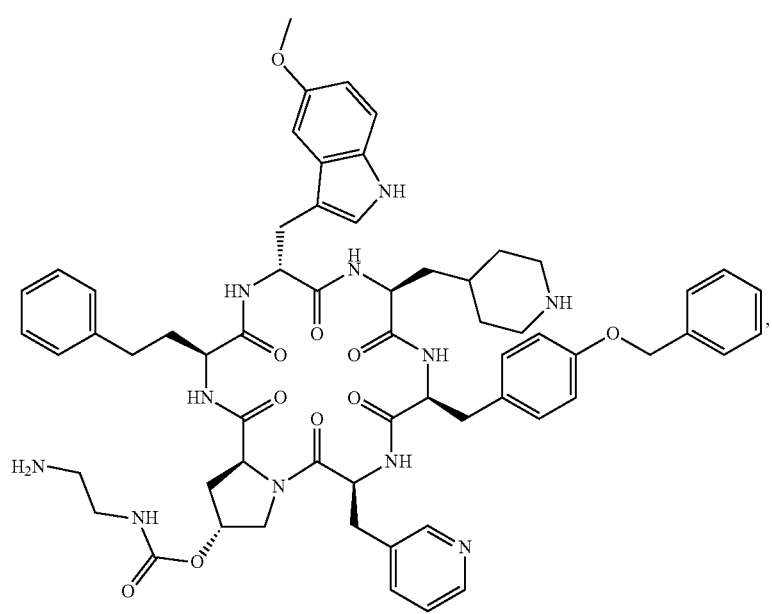, Example 40
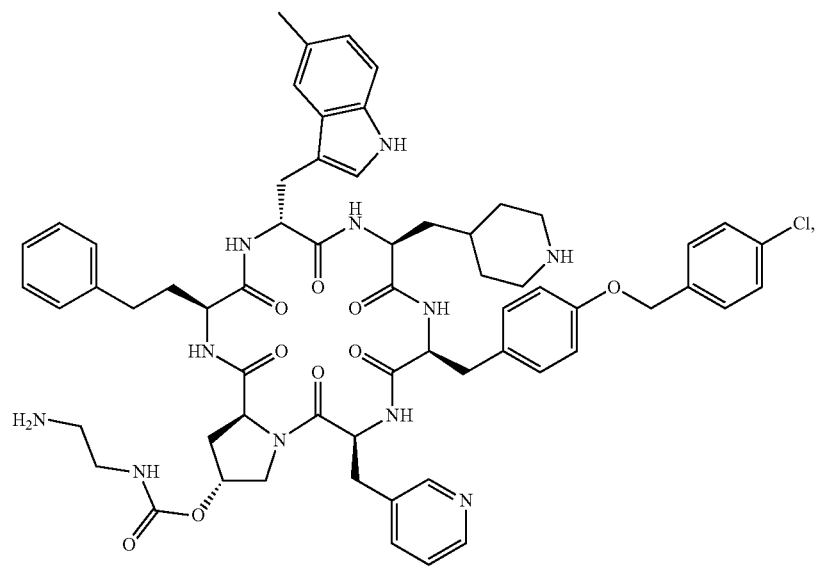
Example 41
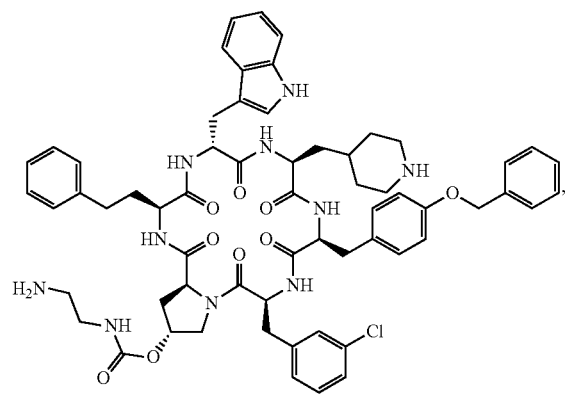
Example 42
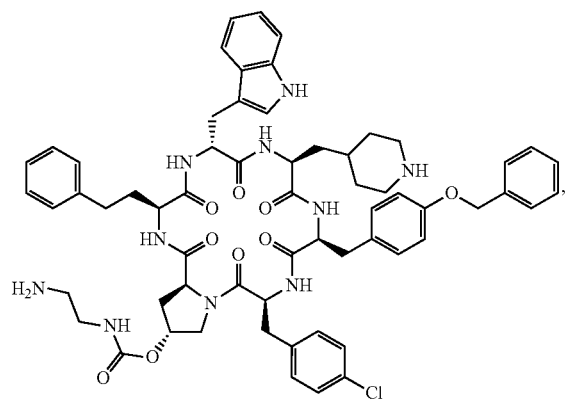
Example 43
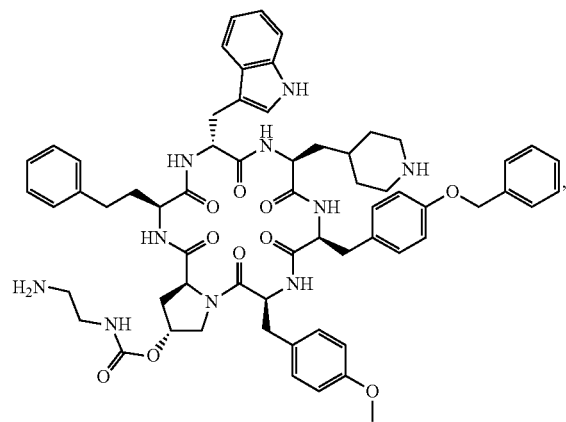
Example 44
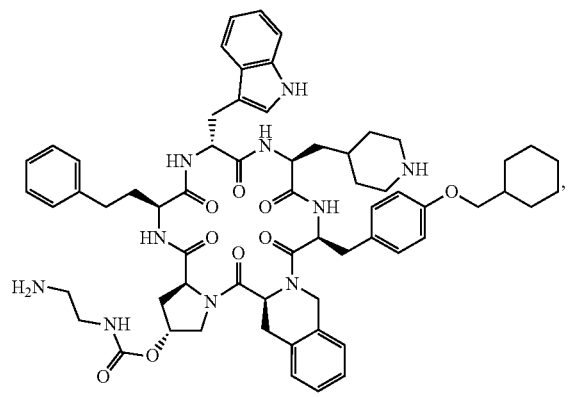

-continued
Example 45
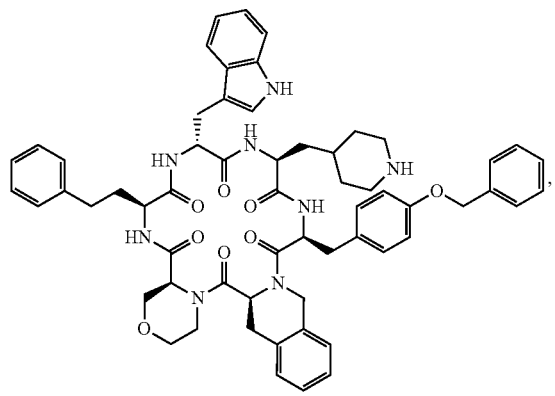
Example 46
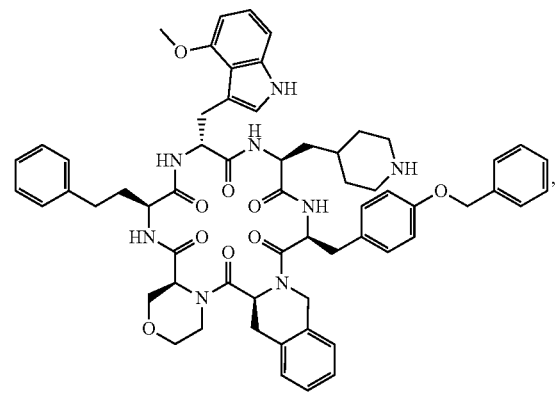
Example 47
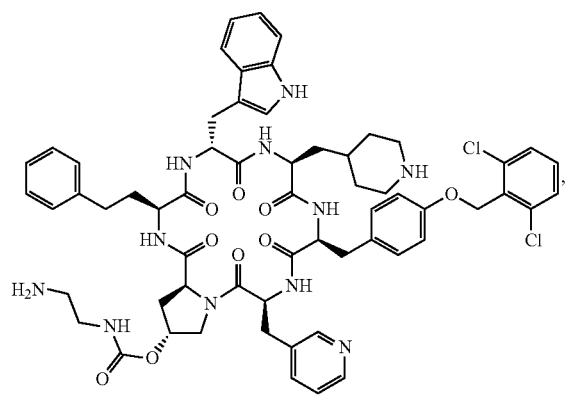
Example 48
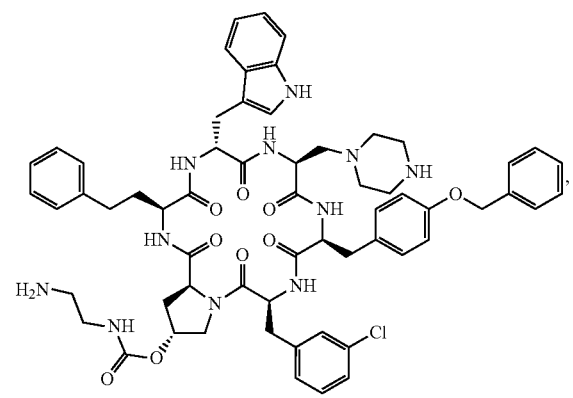
Example 49
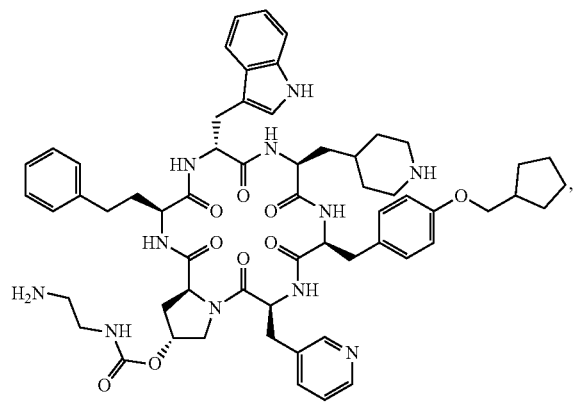
Example 50
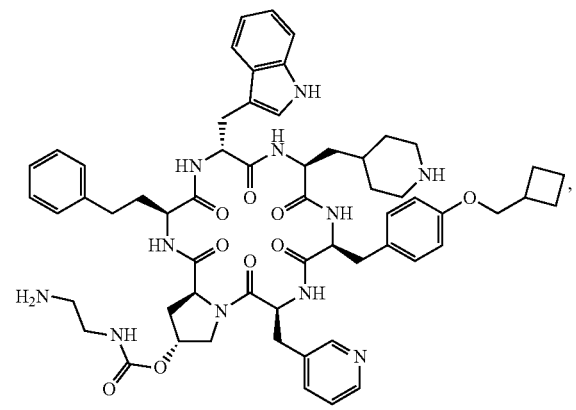

-continued
Example 51
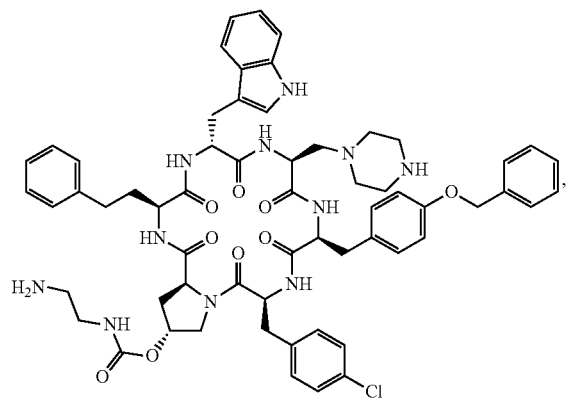
Example 52
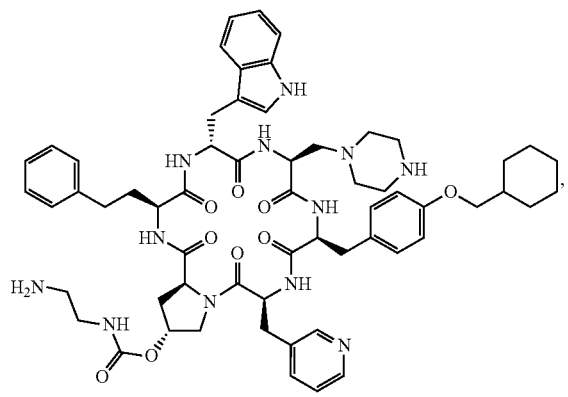
Example 53
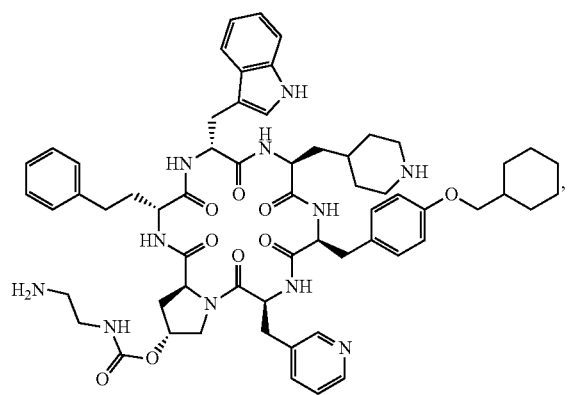
Example 54
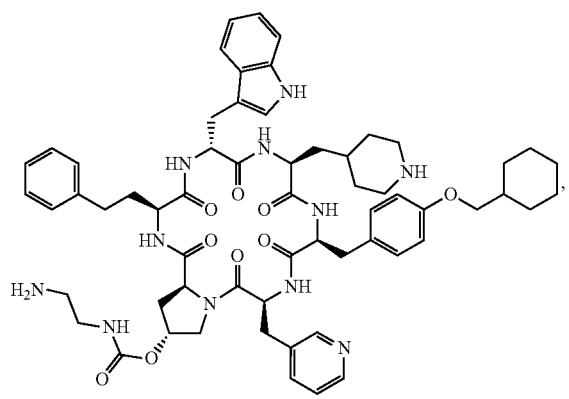
Example 55
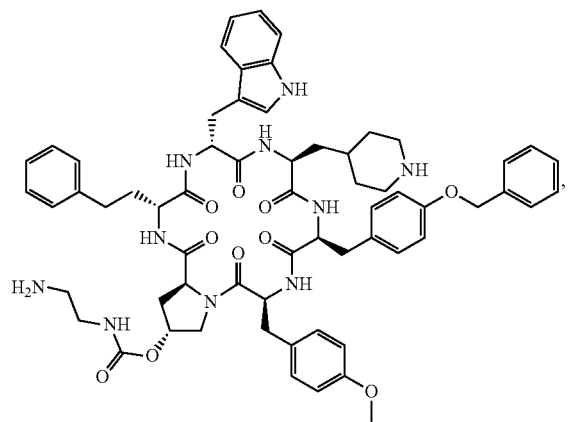
Example 56
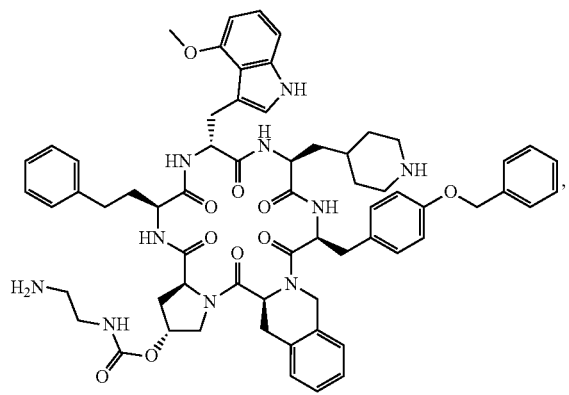

Example 57
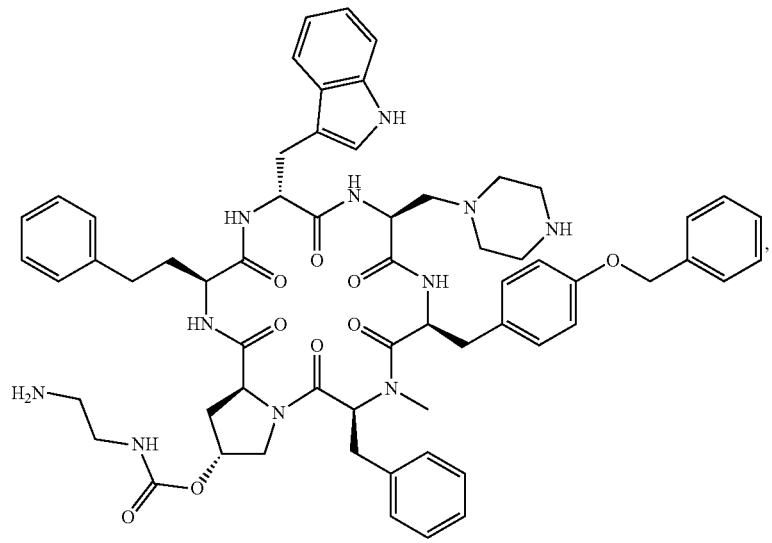
Example 58
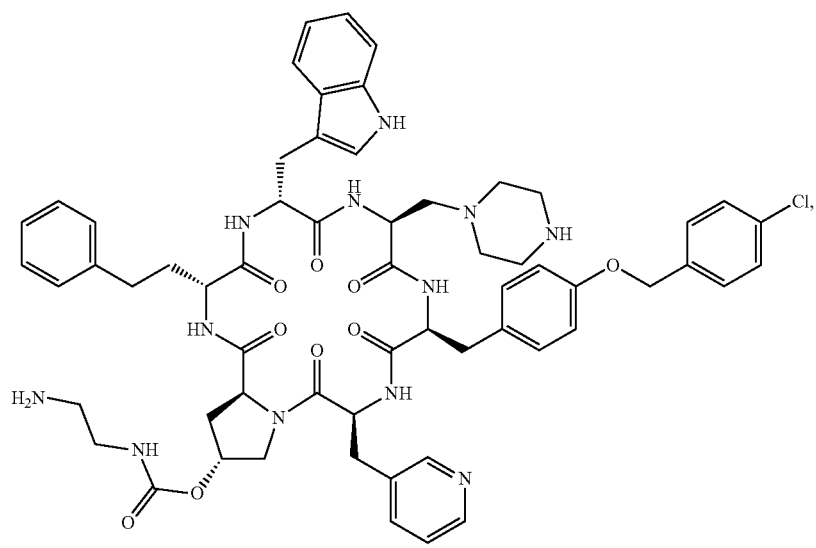
Example 59
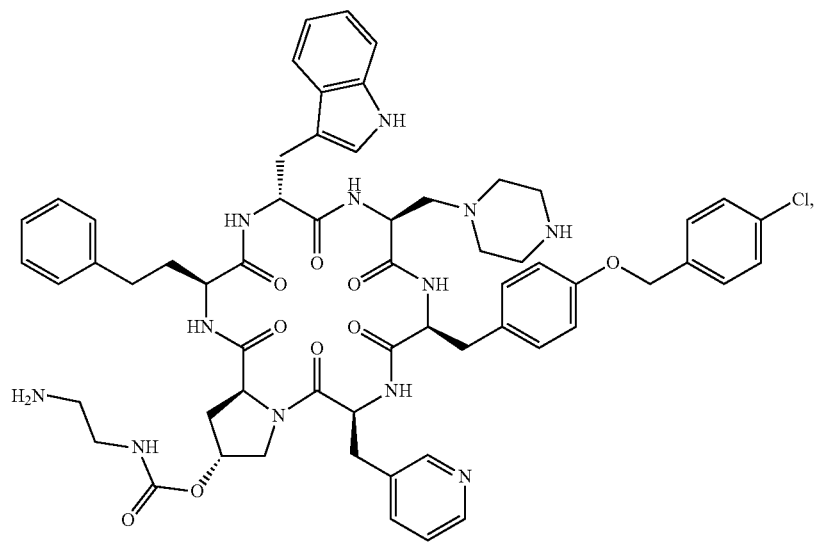

Example 60
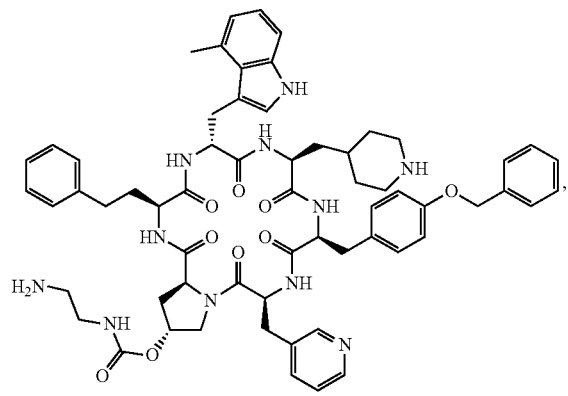
Example 61
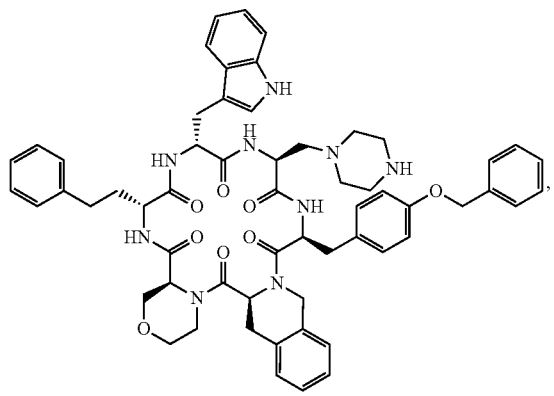
Example 62
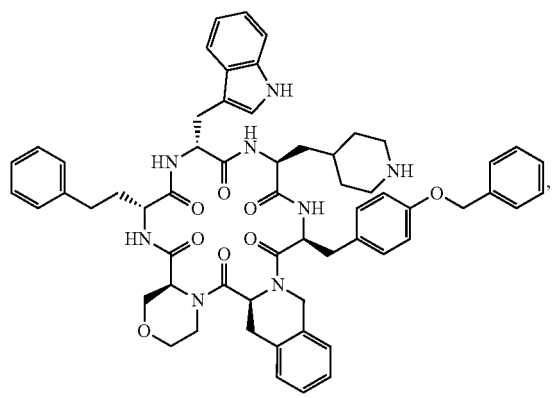
Example 63
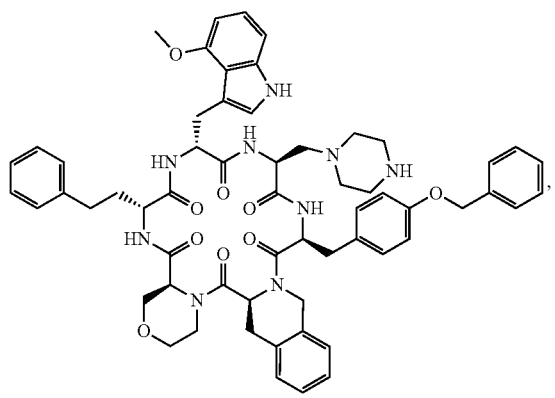
Example 64
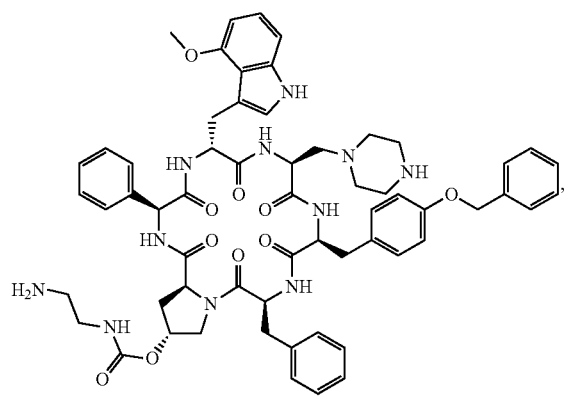
Example 65
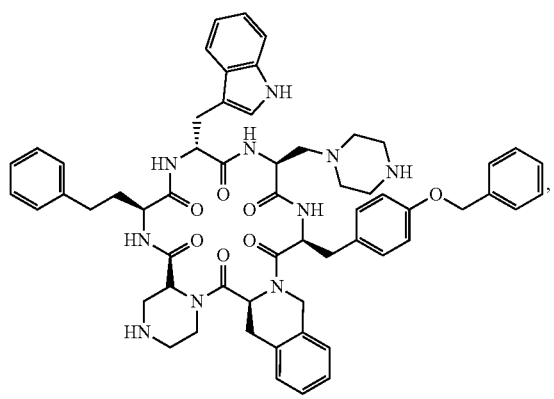

-continued
Example 66
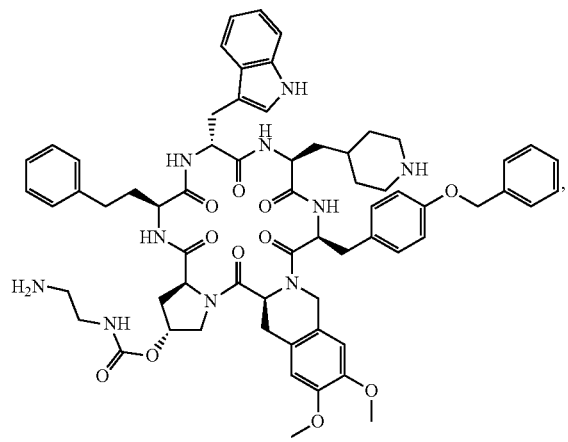
Example 67
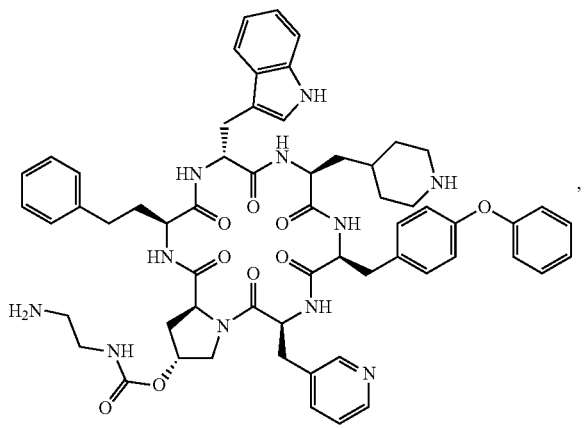
Example 68
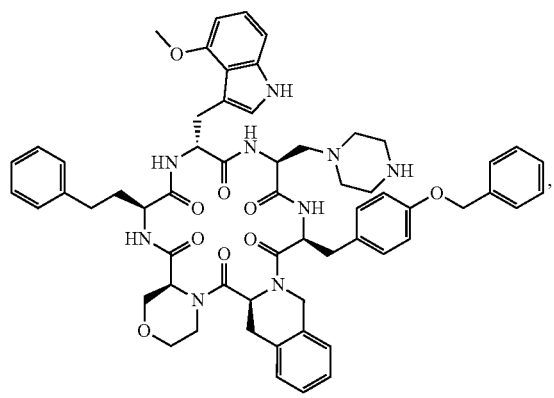
Example 69
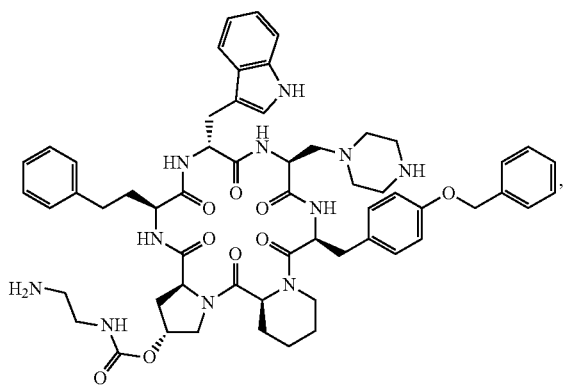
Example 70
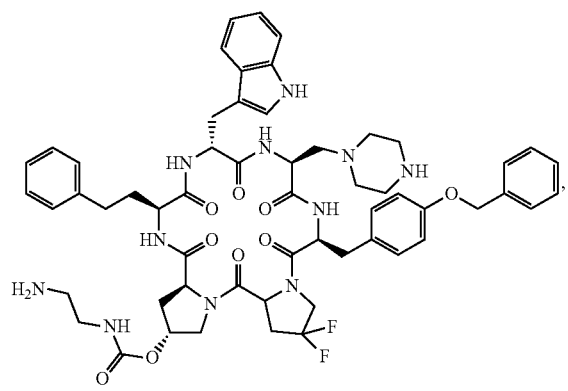
Example 71
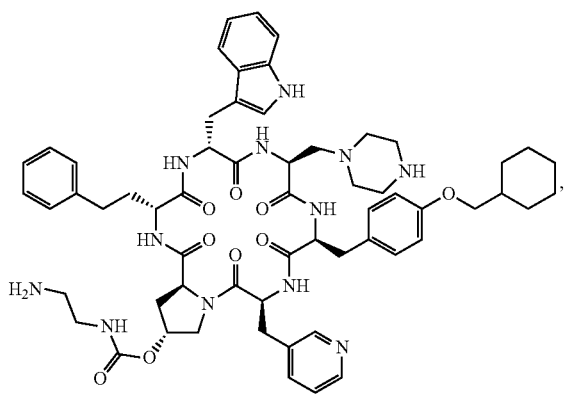

Example 72
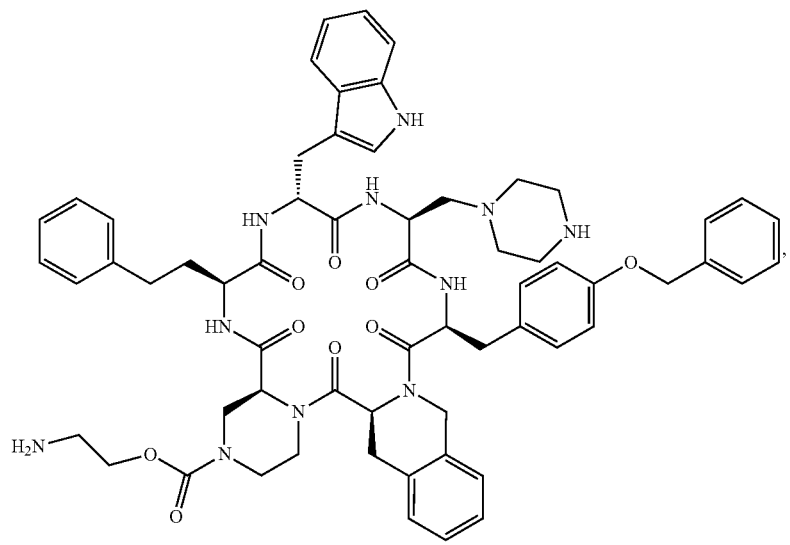
Example 73
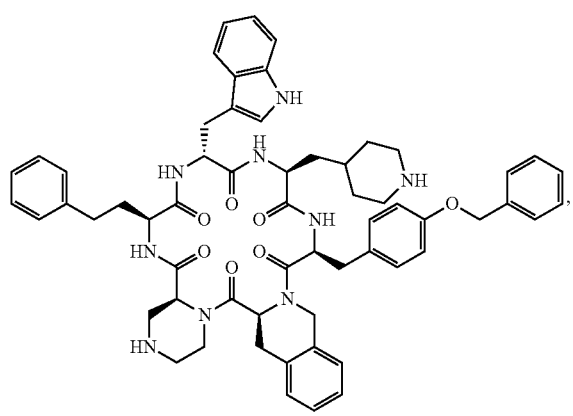
Example 74
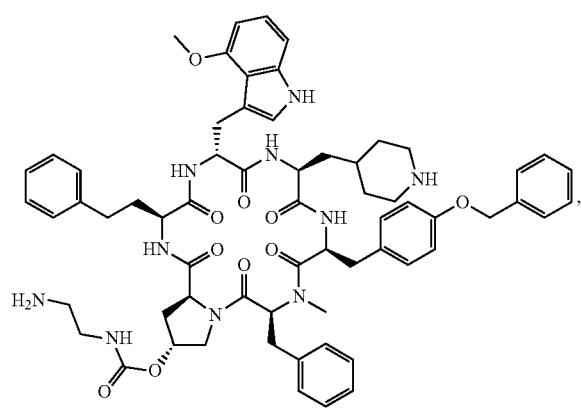
Example 75
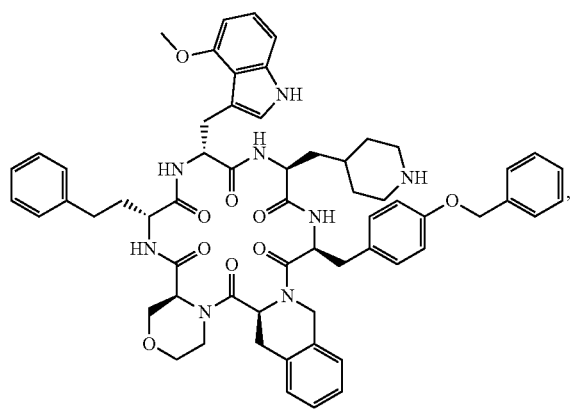
Example 76
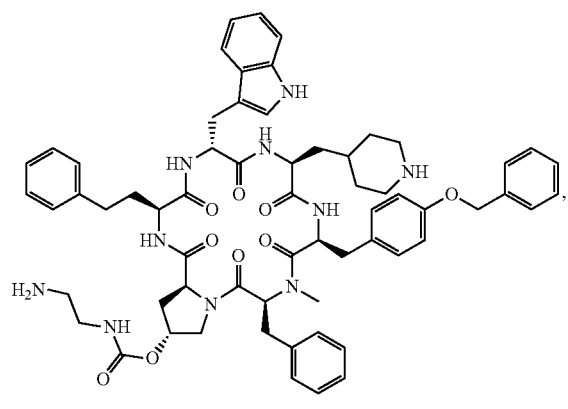

Example 77
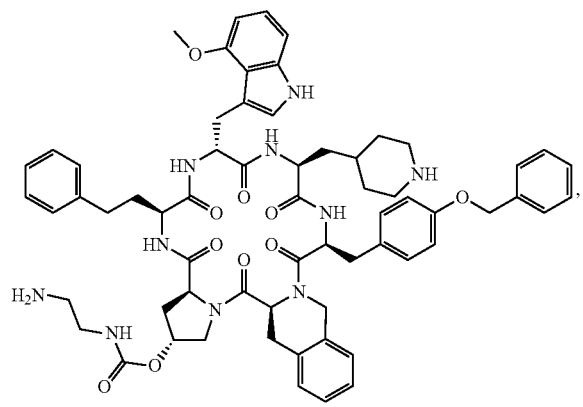
,
Example 78
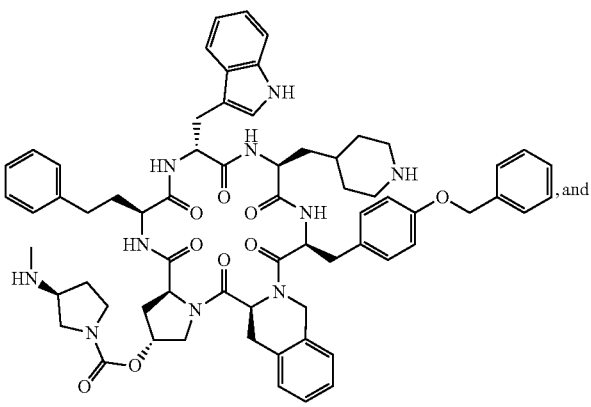
, and
Example 79
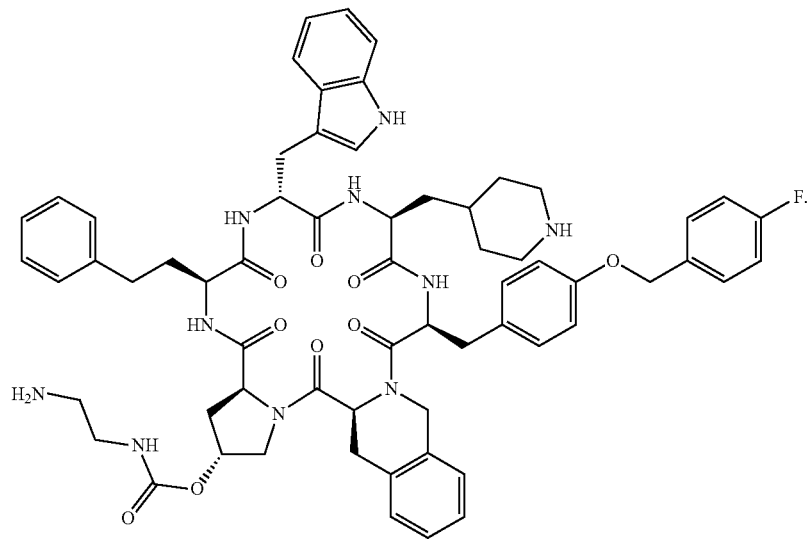
16. The compound according to claim 1 which is selected from the group consisting of:
Example 3
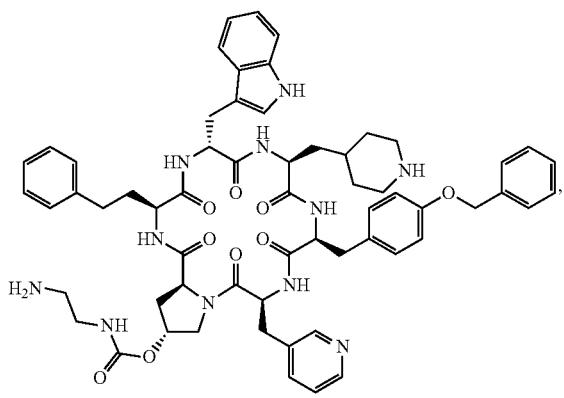
,
Example 14
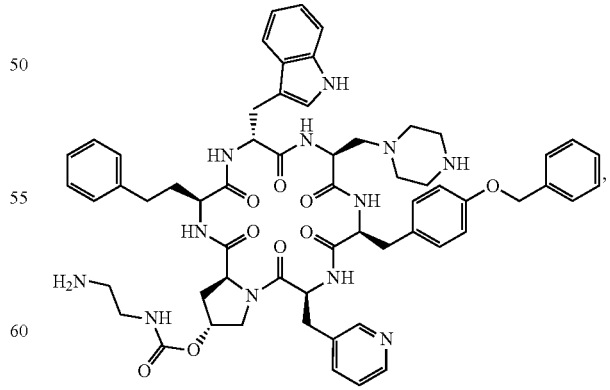
, Example 17

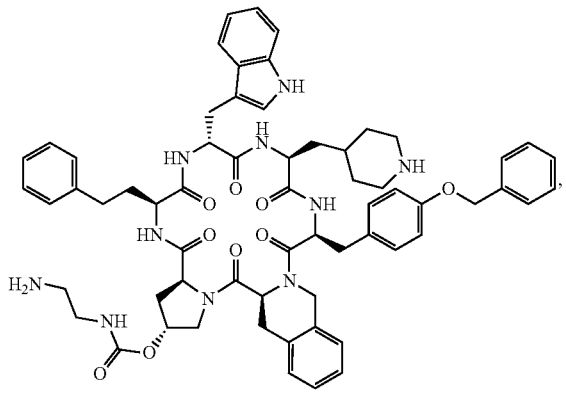

Example 26

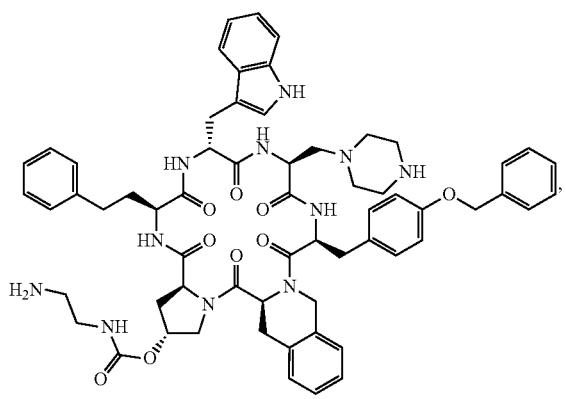

Example 31

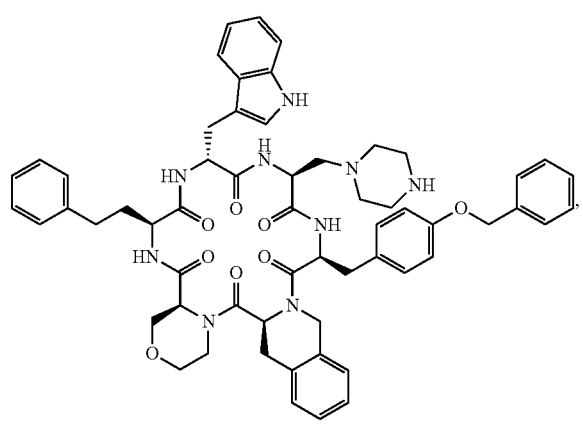

and

Example 45

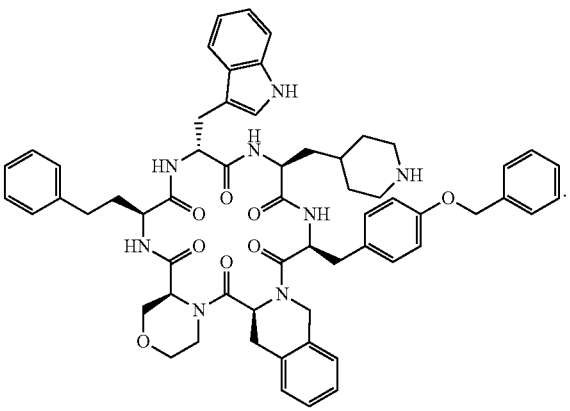

17. The compound according to claim 1 to having $SST_5$ receptor agonist activity.

18. The compound according to claim 2 which exhibits selectivity towards the $SST_5$ receptor compared to the $SST_2$ receptor.

19. A pharmaceutical composition comprising a compound as defined in claim 1 and a pharmaceutically acceptable excipient.

20. A method of treating Cushing's Disease, Cushing's Syndrome, Acromegaly, Neuroendocrine tumours, Thyrotropinomas, Prolactinomas, Non-functioning pituitary adenomas, Nelson's syndrome, Congenital hyperinsulinism, Post-gastric bypass hypoglycaemia, Dumping syndrome, Hyperinsulinemic obesity, Insulinoma, Polycystic kidney disease, Polycystic liver disease, Portal hypertension, Ascites, Pancreatic cancer, Pancreatic fistula, Acute or chronic pancreatitis, Hepatocellular carcinoma, Irritable bowel syndrome/disease or Headache disorders, comprising administering the compound according to claim 1 to a subject in need thereof.

21. A method of treating Carcinoid tumours, migraine, cluster headache, or tension-type headache, comprising administering the compound according to claim 1 to a subject in need thereof.

* * * * *

UNITED STATES PATENT AND TRADEMARK OFFICE
CERTIFICATE OF CORRECTION

PATENT NO. : 11,987,648 B2
APPLICATION NO. : 17/284399
DATED : May 21, 2024
INVENTOR(S) : Giles Albert Brown et al.

Page 1 of 1

It is certified that error appears in the above-identified patent and that said Letters Patent is hereby corrected as shown below:

In the Claims

Claim 15, Column 138, Example 32, should read:

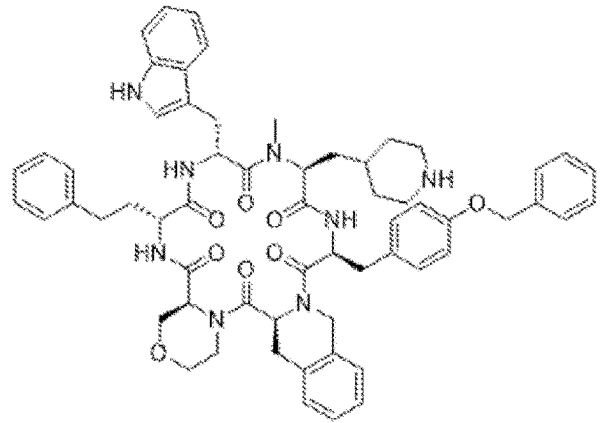

Claim 17, Column 158, Line 26, delete "to" (second occurrence).

Signed and Sealed this
Eighth Day of April, 2025

Coke Morgan Stewart
*Acting Director of the United States Patent and Trademark Office*